United States Patent [19]

Crews, Jr. et al.

[11] Patent Number: 5,654,256
[45] Date of Patent: Aug. 5, 1997

[54] 3-(3-ARYLOXYPHENYL)-1-(SUBSTITUTED METHYL)-S-TRIAZINE-2,4,6-OXO OR THIOTRIONE HERBICIDAL AGENTS

[75] Inventors: Alvin Donald Crews, Jr., Voorhees; Philip Mark Harrington, Cranbury, both of N.J.; Simon David Gill, Fareham, England

[73] Assignee: American Cyanamid Company, Parsippany, N.J.

[21] Appl. No.: 459,439

[22] Filed: Jun. 2, 1995

[51] Int. Cl.$^6$ .......................... C07D 251/34; A01N 43/66
[52] U.S. Cl. .......................... 504/227; 504/230; 544/221; 544/222
[58] Field of Search .................. 544/221, 222; 504/227, 230

[56]         References Cited

U.S. PATENT DOCUMENTS

| 4,093,446 | 6/1978 | Bayer et al. | 71/109 |
| 4,358,308 | 11/1982 | Swithenbank | 71/98 |
| 4,419,122 | 12/1983 | Swithenbank | 71/98 |
| 4,419,123 | 12/1983 | Swithenbank | 71/98 |
| 4,419,124 | 12/1983 | Swithenbank | 71/98 |
| 4,512,797 | 4/1985 | Parg et al. | 71/93 |

FOREIGN PATENT DOCUMENTS

| 27965A2 | 5/1981 | European Pat. Off. |
| 61110A1 | 9/1982 | European Pat. Off. |
| 379915A1 | 8/1990 | European Pat. Off. |

*Primary Examiner*—John M. Ford
*Attorney, Agent, or Firm*—Gregory M. Hill

[57]          ABSTRACT

There is provided a 3-(3-aryloxyphenyl)-1-(substituted methyl)-s-triazine-2,4,6-oxo or thiotrione compound having the structural formula I

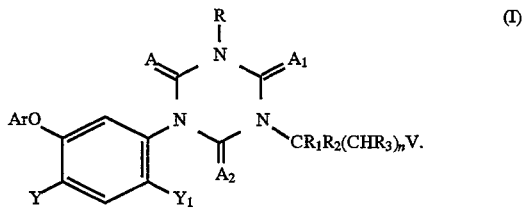

Further provided are a composition and a method comprising that compound for the control of undesirable plant species.

4 Claims, No Drawings

3-(3-ARYLOXYPHENYL)-1-(SUBSTITUTED METHYL)-S-TRIAZINE-2,4,6-OXO OR THIOTRIONE HERBICIDAL AGENTS

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

U.S. Pat. No. 4,512,797 describes certain herbicidal 1,3, 5-triazinone compounds. However, that patent does not disclose the compounds of the present invention and does not disclose any preemergence weed/post-transplant rice applications.

It is therefore an object of the present invention to provide compounds which are highly effective for controlling undesirable plant species.

It is also an object of the present invention to provide methods for controlling undesirable plant species.

It is a feature of the present invention to provide a method for the control of undesirable plant species in the presence of transplanted rice.

These and other objects and features of the present invention will become more apparent from the detailed description thereof set forth below.

SUMMARY OF THE INVENTION

The present invention describes 3-(3-aryloxyphenyl)-1-(substituted methyl)-s-triazine-2,4,6-oxo or thiotrione compounds which are useful as herbicidal agents.

The 3-(3-aryloxyphenyl)-1-(substituted methyl)-s-triazine-2,4,6-oxo or thiotrione compounds of the present invention have the structural formula I

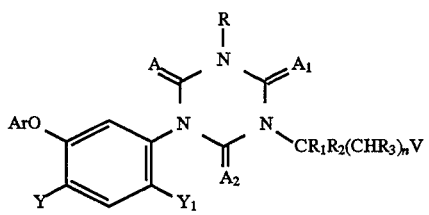

wherein
Ar is

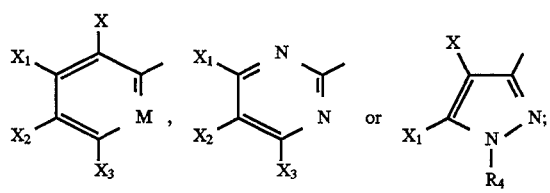

M is $CX_4$ or N;
X, $X_1$, $X_2$, $X_3$, $X_4$ and $Y_1$ are each independently hydrogen, halogen, nitro, cyano, $C_1$–$C_4$alkyl, $C_1$–$C_4$haloalkyl, $C_1$–$C_4$alkoxy, $C_1$–$C_4$haloalkoxy or $S(O)_m R_5$;
m is an integer of 0, 1 or 2;
$R_5$ is $C_1$–$C_4$alkyl or $C_1$–$C_4$haloalkyl;
$R_4$ is $C_1$–$C_4$alkyl;
Y is hydrogen or halogen;
A, $A_1$ and $A_2$ are each independently O or S;
R is hydrogen, $C_1$–$C_4$alkyl, $C_2$–$C_6$alkoxyalkyl, $C_3$–$C_{12}$alkylcarbonylalkyl, $C_3$–$C_{12}$haloalkylcarbonylalkyl, $C_3$–$C_{12}$alkoxycarbonylalkyl, $C_3$–$C_{12}$haloalkoxycarbonylalkyl, $C_3$–$C_6$alkenyl, $C_3$–$C_6$alkynyl, an alkali metal or phenyl optionally substituted with one to three halogen, $C_1$–$C_4$alkyl, $C_1$–$C_4$alkoxy or $C_1$–$C_4$haloalkoxy groups;
$R_1$ is hydrogen, $C_1$–$C_4$alkyl or phenyl optionally substituted with one to three halogen, $C_1$–$C_4$alkyl, $C_1$–$C_4$alkoxy or $C_1$–$C_4$haloalkoxy groups, and when taken together with $R_2$, $R_1R_2$ may represent the structure: —$(CH_2)_p$— where p is an integer of 2, 3, 4 or 5, and when n is 0, $R_1$ may be taken together with $R_{10}$ to form a ring in which $R_1R_{10}$ is represented by the structure: —$(CH_2)_q$— where q is an integer of 2 or 3;
$R_2$ is hydrogen or $C_1$–$C_4$alkyl, and when taken together with $R_1$, $R_2R_1$ may represent the structure: —$(CH_2)_p$— where p is an integer of 2, 3, 4 or 5;
$R_3$ is hydrogen or $C_1$–$C_4$alkyl;
n is an integer of 0, 1 or 2;
V is $C(O)R_6$, $C(W)R_7$, $CH_2OC(O)R_8$ or $CH(OR_9)_2$;
$R_6$ is OH, $OR_{10}$, $SR_{10}$ or $NR_{11}R_{12}$;
W is O, $NOR_{11}$, $NCOR_{11}$ or $NNHCONH_2$;
$R_7$ and $R_8$ are each independently hydrogen or $C_1$–$C_4$alkyl;
$R_9$ is $C_1$–$C_4$alkyl;
$R_{10}$ is $C_1$–$C_6$alkyl optionally substituted with $C_1$–$C_4$alkoxy, $C_1$–$C_4$alkylthio, $C_2$–$C_6$alkoxycarbonylalkyl, halogen, hydroxy, $C_3$–$C_6$cycloalkyl, tetrahydrofuryl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups,
$C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups,
$C_3$–$C_6$alkynyl optionally substituted with $C_1$–$C_4$alkoxy or halogen,
$C_3$–$C_6$cycloalkyl,
N=$C(R_7R_8)$, or
an alkali metal, alkaline earth metal, manganese, copper, zinc, cobalt, silver, nickel, ammonium or organic ammonium cation, and when n is 0, $R_{10}$ may be taken together with $R_1$ to form a ring in which $R_{10}R_1$ is represented by the structure: —$(CH_2)_q$— where q is an integer of 2 or 3; and
$R_{11}$ and $R_{12}$ are each independently hydrogen, $C_1$–$C_6$alkyl, $C_2$–$C_6$alkoxycarbonylalkyl,
benzyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, or
phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups.

This invention also relates to compositions containing those compounds and methods for using those compounds and compositions. Advantageously, it has been found that the compounds of the present invention, and compositions containing them, are useful for the control of undesirable plant species. The compounds of the present invention are especially useful for the selective control of undesirable plant species in the presence of crop plants.

DETAILED DESCRIPTION OF THE INVENTION

The present invention provides a method for controlling undesirable plant species which comprises applying to the foliage of said plants or to the soil or water containing seeds or other propagating organs thereof, a herbicidally effective amount of a formula I, 3-(3-aryloxyphenyl)-1-(substituted methyl)-s-triazine-2,4,6-oxo or thiotrione compound.

The present invention also provides a method for the control of undesirable plant species in transplanted rice which comprises applying to the soil or water containing seeds or other propagating organs of said undesirable plant species, after the rice has been transplanted, a herbicidally effective amount of a formula I, 3-(3-aryloxyphenyl)-1-(substituted methyl)-s-triazine-2,4,6-oxo or thiotrione compound.

The 3-(3-aryloxyphenyl)-1-(substituted methyl)-s-triazine-2,4,6-oxo or thiotrione compounds of the present invention have the structural formula I

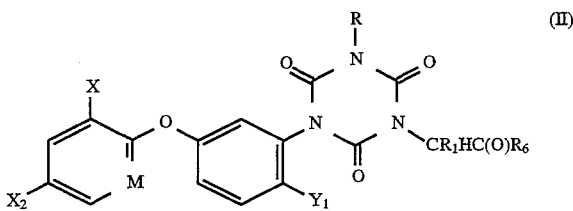

wherein Ar, Y, $Y_1$, A, $A_1$, $A_2$, R, $R_1$, $R_2$, $R_3$, n and V are as described above.

Preferred formula I compounds of this invention are those wherein

Ar is

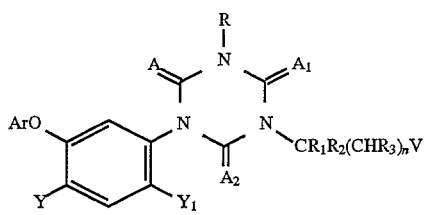

M is $CX_4$ or N;

X is hydrogen, halogen, nitro, cyano, $C_1$–$C_4$alkyl or $C_1$–$C_4$haloalkyl;

$X_1$ is hydrogen, halogen, nitro or $C_1$–$C_4$alkyl;

$X_2$ is hydrogen, halogen, nitro, cyano, $C_1$–$C_4$haloalkyl or $S(O)_mR_5$;

m is an integer of 0 or 1;

$R_4$ and $R_5$ are each independently $C_1$–$C_4$alkyl;

$X_3$ is hydrogen, halogen or $C_1$–$C_4$alkoxy;

$X_4$ is hydrogen or halogen;

Y is hydrogen or F;

$Y_1$ is hydrogen, halogen, nitro or cyano;

A, $A_1$ and $A_2$ are O;

R is hydrogen, $C_1$–$C_4$alkyl, $C_1$–$C_4$alkoxymethyl, ($C_1$–$C_4$alkoxy) carbonylmethyl, allyl or propargyl;

$R_1$ is hydrogen or $C_1$–$C_4$alkyl, and when n is 0, $R_1$ may be taken together with $R_{10}$ to form a ring in which $R_1R_{10}$ is represented by the structure: —$(CH_2)_2$—;

$R_2$ and $R_3$ are hydrogen;

n is an integer of 0, 1 or 2;

V is $C(O)R_6$;

$R_6$ is OH, $OR_{10}$ or $NR_{11}R_{12}$;

$R_{10}$ is $C_1$–$C_6$alkyl optionally substituted with halogen or 2-tetrahydrofuryl, or an alkali metal, ammonium or organic ammonium cation, and when n is 0, $R_{10}$ may be taken together with $R_1$ to form a ring in which $R_{10}R_1$ is represented by the structure: —$(CH_2)_2$—; and $R_{11}$ and $R_{12}$ are each independently hydrogen, $C_1$–$C_6$alkyl or $C_1$–$C_4$alkoxycarbonylmethyl.

More preferred herbicidal agents of the present invention are those having the structural formula II

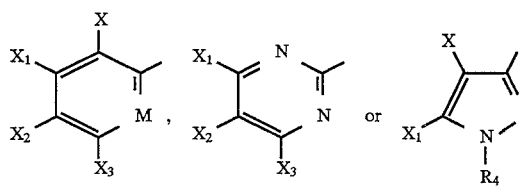

wherein

M is $CX_4$ or N;

X is halogen;

$X_2$ is halogen or $C_1$–$C_4$haloalkyl;

$X_4$ is hydrogen or halogen;

$Y_1$ is halogen, nitro or cyano;

R is hydrogen, $C_1$–$C_4$alkyl, $C_1$–$C_4$alkoxymethyl, ($C_1$–$C_4$alkoxy) carbonylmethyl or allyl;

$R_1$ is hydrogen or $C_1$–$C_4$alkyl;

$R_6$ is OH or $OR_{10}$; and $R_{10}$ is $C_1$–$C_6$alkyl or an alkali metal, ammonium or organic ammonium cation.

Compounds of this invention which are especially useful for the control of undesirable plant species are those having the stuctural formula II wherein M is $CX_4$ or N;

X is Cl;

$X_2$ is Cl or $CF_3$;

$X_4$ is hydrogen or F;

$Y_1$ is F, Cl, Br, nitro or cyano;

R is hydrogen, $C_1$–$C_4$alkyl, ($C_1$–$C_4$alkoxy) carbonylmethyl or allyl;

$R_1$ is hydrogen or $C_1$–$C_4$alkyl;

$R_6$ is $OR_{10}$; and $R_{10}$ is $C_1$–$C_6$alkyl.

3-(3-Aryloxyphenyl)-1-(substituted methyl)-s-triazine-2,4,6-trione compounds of the present invention which are particularly effective herbicidal agents include methyl 3-{2-bromo-5-[(2-chloro-α,α,α,6-tetrafluoro-p-tolyl)oxy]phenyl}tetrahydro-5-methyl-2,4,6-trioxo-s-triazine-1(2H)-acetate;

methyl 3-{5-[(2-chloro-α,α,α,6-tetrafluoro-p-tolyl)-oxy]-2-fluorophenyl}tetrahydro-5-methyl-2,4,6-trioxo-s-triazine-1(2H)-acetate;

methyl 3-{[2-chloro-5-(2-chloro-α,α,α-trifluoro-p-tolyl)oxy]phenyl}tetrahydro-5-methyl-2,4,6-trioxo-s-triazine-1(2H)-acetate;

dimethyl 5-[5-(2,4-dichlorophenoxy)-2-nitrophenyl]-dihydro-2,4,6-trioxo-s-triazine-1,3(2H,4H)-diacetate;

methyl 3-{5-[(2-chloro-α,α,α,6-tetrafluoro-p-tolyl)oxy]-2-nitrophenyl}tetrahydro-5-methyl-2,4,6-trioxo-s-triazine-1(2H)-acetate;

methyl 3-{5-[(2-chloro-α,α,α-trifluoro-p-tolyl)oxy]-2-nitrophenyl}tetrahydro-5-methyl-2,4,6-trioxo-s-triazine-1(2H)-acetate;

methyl 3-{2-bromo-5-[(2-chloro-α,α,α,6-tetrafluoro-p-tolyl)oxy]phenyl}tetrahydro-α,5-dimethyl-2,4,6-trioxo-s-triazine-1(2H)-acetate;

ethyl 3-{5-[(2-chloro-α,α,α-trifluoro-p-tolyl)oxy]-2-nitrophenyl}tetrahydro-2,4,6-trioxo-s-triazine-1(2H)-acetate;

ethyl 3-{5-[(2-chloro-α,α,α,6-tetrafluoro-p-tolyl)oxy]-2-cyanophenyl}tetrahydro-5-methyl-2,4,6-trioxo-s-triazine-1(2H)-acetate;

methyl 3-[5-(2,4-dichlorophenoxy)-2-nitrophenyl]-tetrahydro-5-methyl-2,4,6-trioxo-s-triazine-1(2H)-acetate;

methyl 3-{5-[(2-chloro-α,α,α-trifluoro-p-tolyl)oxy]-2-nitrophenyl}tetrahydro-2,4,6-trioxo-s-triazine-1(2H)-acetate;

ethyl 3-allyl-5-{5-[(2-chloro-α,α,α-trifluoro-p-tolyl)oxy]-2-nitrophenyl}tetrahydro-2,4,6-trioxo-s-triazine-1(2H)-acetate; and tert-butyl 3-{5-[(2-chloro-α,α,α,6-tetrafluoro-p-tolyl)oxy]-2-nitrophenyl}tetrahydro-5-methyl-2,4,6-trioxo-s-triazine-1(2H)-acetate, among others.

Exemplary of halogen hereinabove are flourine, chlorine, bromine and iodine. The terms $C_1$–$C_4$haloalkyl and $C_1$–$C_4$haloalkoxy as used in the specification and claims designates a $C_1$–$C_4$alkyl group or a $C_1$–$C_4$alkoxy group substituted with one or more halogen atoms, respectively. In formula I above, alkali metals include: sodium, potassium and lithium. Alkaline earth metals of formula I include magnesium and calcium. Further, the term organic ammonium is defined as a group consisting of a positively charged nitrogen atom joined to from one to four aliphatic groups, each containing from one to sixteen carbon atoms.

Advantageously, it has now been found that certain compounds of the present invention are especially useful for the selective control of undesirable plant species in the presence of important agronomic crops.

Compounds of formula I wherein A, $A_1$ and $A_2$ are O and V is $CO_2R_{10}$ may be prepared by reacting a 3-aryloxybenzoic acid of formula III with thionyl chloride to form a 3-aryloxybenzoyl chloride compound of formula IV, reacting the formula IV compound with ammonium hydroxide to form a 3-aryloxybenzamide compound of formula V, reacting the formula V compound with sodium hypochlorite and sodium hydroxide to form an intermediate isocyante compound of formula VI, reacting the formula VI compound with an amine of formula VII to form a 1-(3-aryloxyphenyl)-3-substituted methylurea of formula VIII and cyclizing the formula VIII compound with N-(chlorocarbonyl) isocyanate to form the desired formula I compound and optionally alkylating the formula I compound wherein R is hydrogen with an alkylating agent of formula IX and a base. The reaction scheme is shown in Flow Diagram I.

FLOW DIAGRAM I

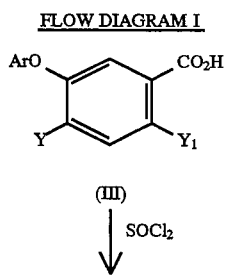

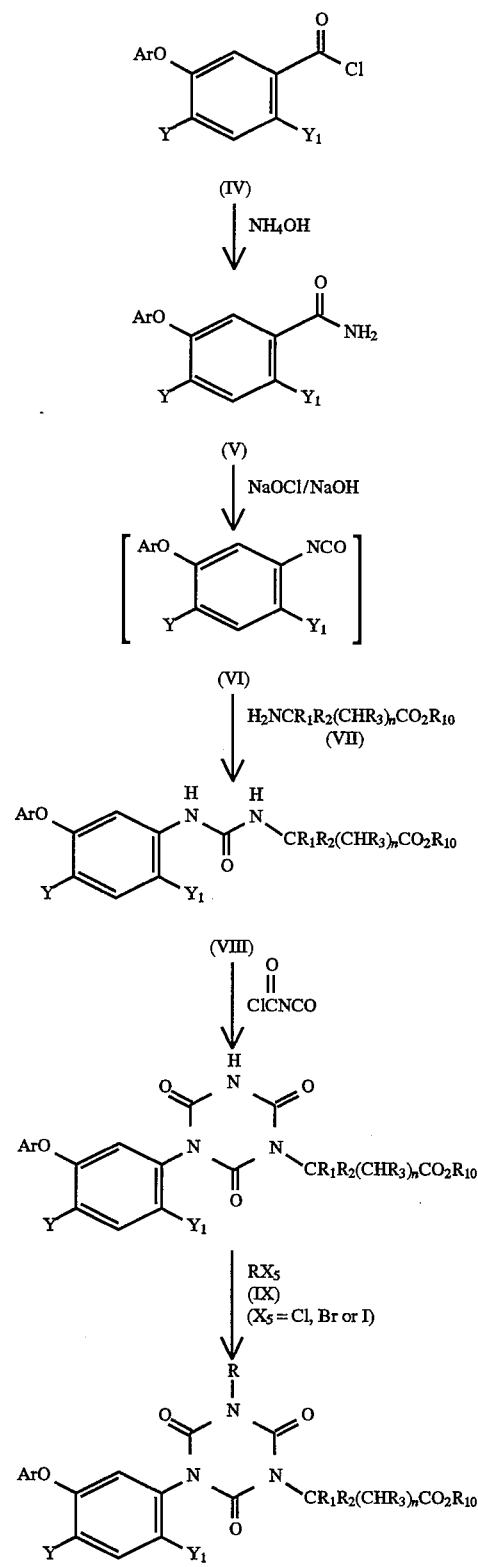

Alternatively, compounds of formula I wherein A, $A_1$, and $A_2$ are O, V is $CO_2R_{10}$ and R is other than hydrogen or an alkali metal may be prepared by reacting a formula VI isocyanate with an amine of formula X to form a urea compound of formula XI, cyclizing the formula XI compound with N-(chlorocarbonyl) isocyanate to form a 1-(3-aryloxyphenyl)-s-triazine-2,4,6-(1H,3H,5H)-trione compound of formula XII and alkylating the formula XII compound with an alkylating agent of formula XIII and a base to form the desired formula I compound. The above reactions are shown in Flow Diagram II.

base. The above reactions are shown below in Flow Diagram III.

FLOW DIAGRAM II

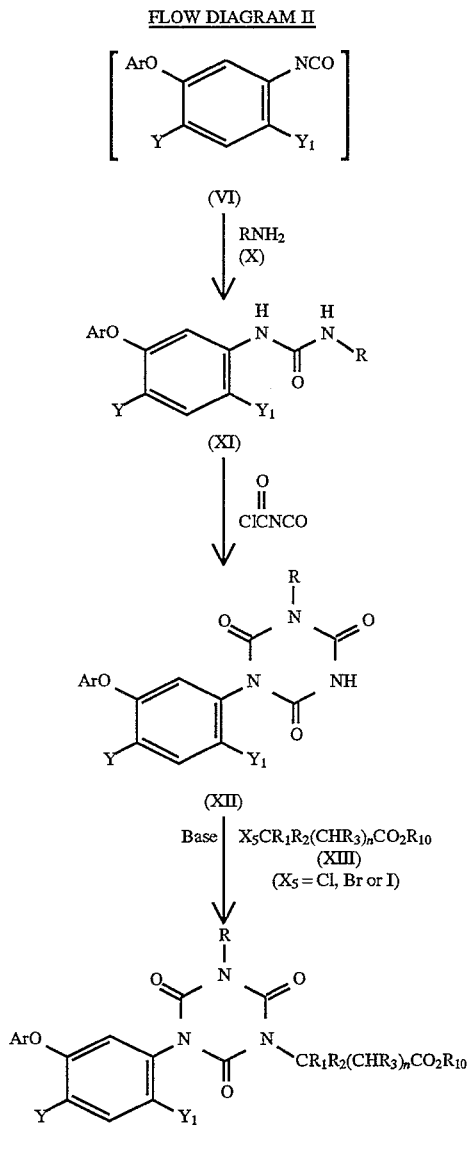

Formula I compounds wherein A, $A_1$ and $A_2$ are O and V is $CO_2R_{10}$ may also be prepared by reacting a 3-fluorobenzoic acid of formula XIV with thionyl chloride to form a 3-fluorobenzoyl chloride compound of formula XV, reacting the formula XV compound with sodium azide to form a 3-fluorobenzoyl azide compound of formula XVI, heating the formula XVI compound to form an intermediate isocyanate compound of formula XVII, reacting the isocyanate compound with an amine of formula VII to form a 1-(3-fluorophenyl)-3-(substituted methyl)urea of formula XVIII, cyclizing the formula XVIII compound with N-(chlorocarbonyl) isocyanate to form a 1-(3-fluorophenyl)-3-(substituted methyl)-s-triazine-2,4,6-trione compound of formula XIX and reacting the formula XIX compound with an alcohol of formula XX and a base to form the desired formula I compound and optionally alkylating the formula I compound with an alkylating agent of formula IX and a

FLOW DIAGRAM III

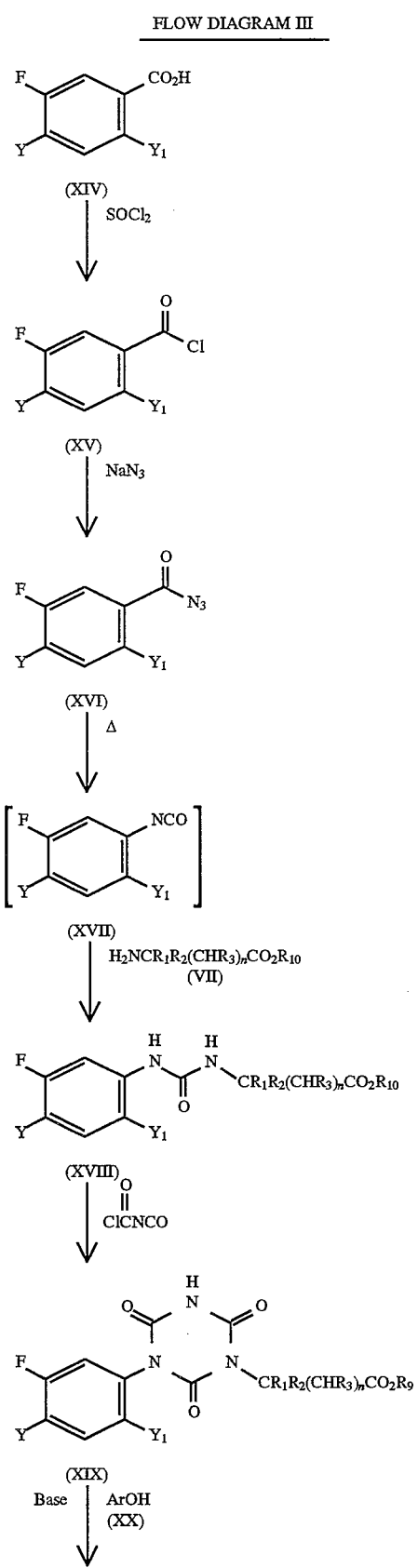

-continued
FLOW DIAGRAM III

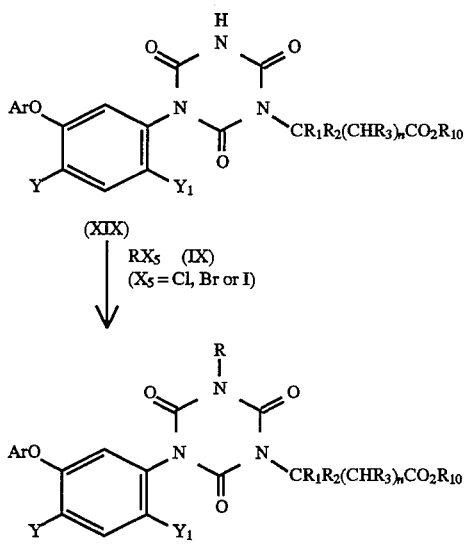

Alternatively, compounds of formula I wherein A, $A_1$ and $A_2$ are O, V is $CO_2R_{10}$ and R is other than hydrogen or an alkali metal may be prepared by cyclizing a urea of formula XXI with N-(chlorocarbonyl) isocyanate to form a 1-(3-methoxyphenyl)-s-triazine-2,4,6-trione compound of formula XXII, reacting the formula XXII compound with a Lewis or protic acid such as boron tribromide to form a 1-(3-hydroxyphenyl)-s-triazine-2,4,6-trione compound of formula XXIII, reacting the formula XXIII compound with a fluoroaryl compound of formula XXIV and a base to form a 1-(3-aryloxyphenyl)-s-triazine-2,4,6-trione compound of formula XXV and alkylating the formula XXV compound with an alkylating agent of formula XIII and a base to form the desired formula I compound. The reaction scheme is shown in Flow Diagram IV.

FLOW DIAGRAM IV

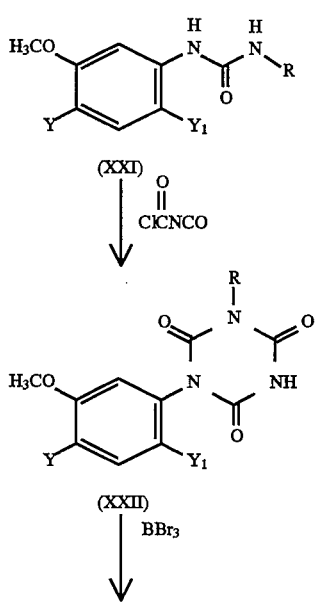

-continued
FLOW DIAGRAM IV

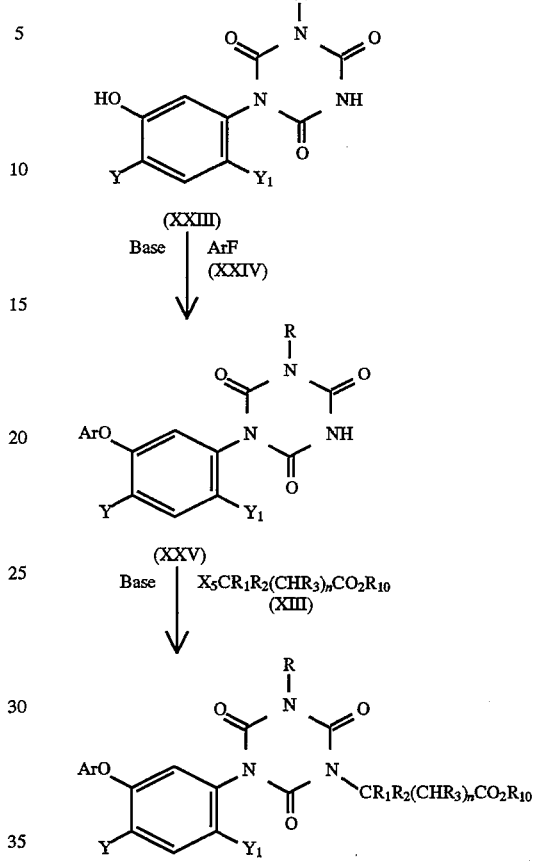

Compounds of formula I wherein A, $A_1$ and $A_2$ are O, V is $CO_2R_{10}$ and R is other than hydrogen or an alkali metal may also be prepared by cyclizing a urea of formula XXVI with N-(chlorocarbonyl) isocyanate to form a 1-(3-methoxyphenyl)-3-(substituted methyl)-s-triazine-2,4,6-trione compound of formula XXVII, reacting the formula XXVII compound with an alkylating agent of formula IX and a base to form a 1-(3-methoxyphenyl)-3-(substituted methyl)-5-substituted-s-triazine-2,4,6-trione compound of formula XXVIII, reacting the formula XXVIII compound with a Lewis or protic acid such as boron tribromide to form a 1-(3-hydroxyphenyl)-3-(substituted methyl)-5-substituted-s-triazine-2,4,6-trione compound of formula XXIX and reacting the formula XXIX compound with a fluoroaryl compound of formula XXIV and a base to form the desired formula I compound. The reactions are shown in Flow Diagram V.

FLOW DIAGRAM V

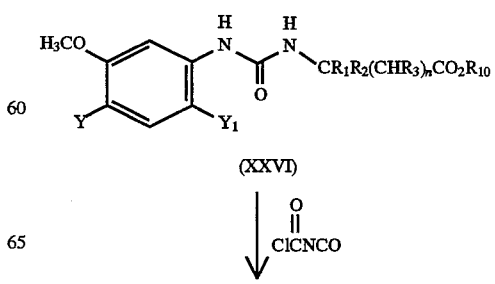

FLOW DIAGRAM V

-continued

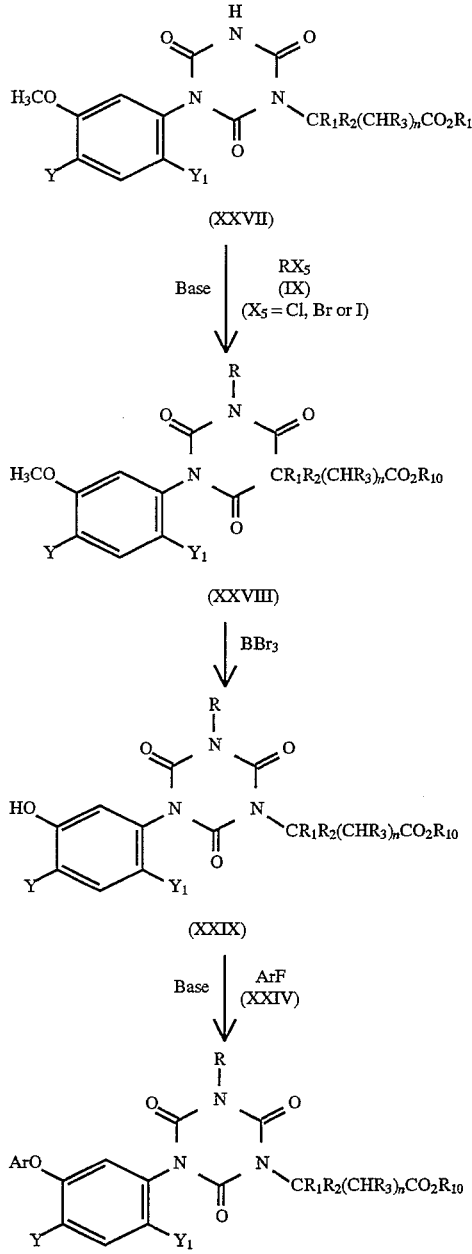

FLOW DIAGRAM VI

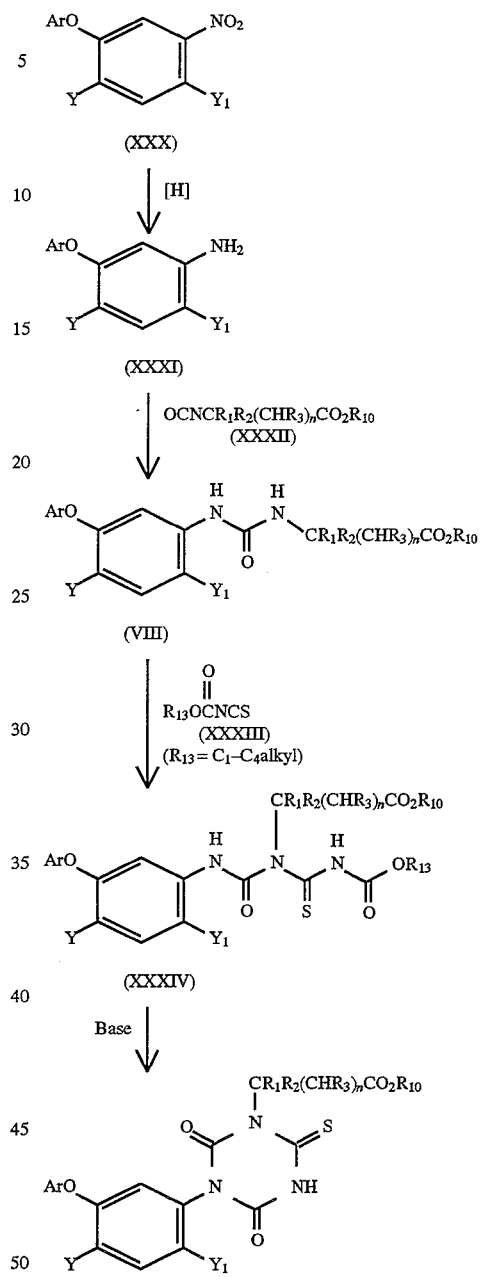

Compounds of formula I wherein A and $A_2$ are O, $A_1$ is S and V is $CO_2R_{10}$ may be prepared by reducing a 3-(aryloxy)nitrobenzene of formula XXX to form a 3-(aryloxy)aminobenzene compound of formula XXXI, reacting the formula XXXI compound with an isocyanate of formula XXXII to form a 1-(3-aryloxyphenyl)-3-(substituted methyl)urea compound of formula VIII, reacting the formula VIII compound with an isothiocyanate of formula XXXIII to form an intermediate compound of formula XXXIV, and cyclizing the formula XXXIV compound with base to form the desired formula I compound and optionally alkylating the formula I compound wherein R is hydrogen with an alkylating agent of formula IX and a base. The reactions are shown in Flow Diagram VI.

Alternatively, compounds of formula I wherein A and $A_2$ are O, $A_1$ is S and V is $CO_2R_{10}$ may be prepared by reacting a formula XXXI compound with an isocyanate of formula XXXV to form a urea of formula XI, reacting the formula XI compound with an isothiocyanate of formula XXXIII to form an intermediate compound of formula XXXVI, cyclizing the formula XXXVI compound with base to form a 1-(3-aryloxyphenyl)-s-triazine-2,6-dioxo-4-thione compound of formula XXXVII, and alkylating the formula XXXVII compound with an alkylating agent of formula XIII and a base to form the desired formula I compound. The reaction scheme is shown below in Flow Diagram VII.

Compounds of formula I wherein A and $A_1$ are O, $A_2$ is S and V is $CO_2R_{10}$ may be prepared by reacting a compound of formula XXXI with an isothiocyanate of formula XXXVIII to form a thiourea of formula XXXIX, and cyclizing the formula XXXIX compound with N-(chlorocarbonyl) isocyanate to form the desired formula I compound and optionally alkylating the formula I compound wherein R is hydrogen with an alkylating agent of formula IX and a base. The reactions are shown in Flow Diagram VIII.

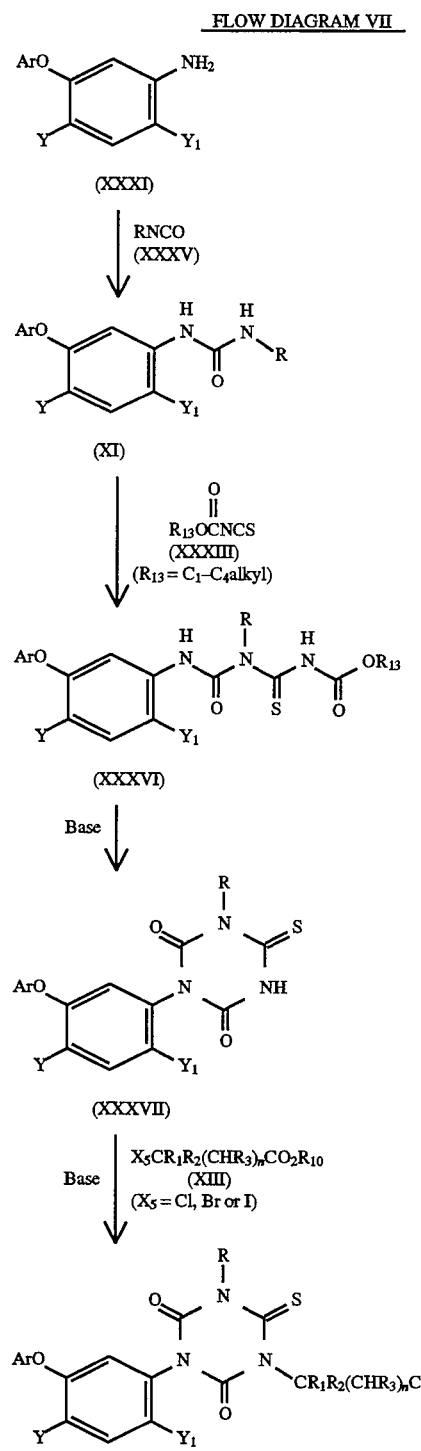

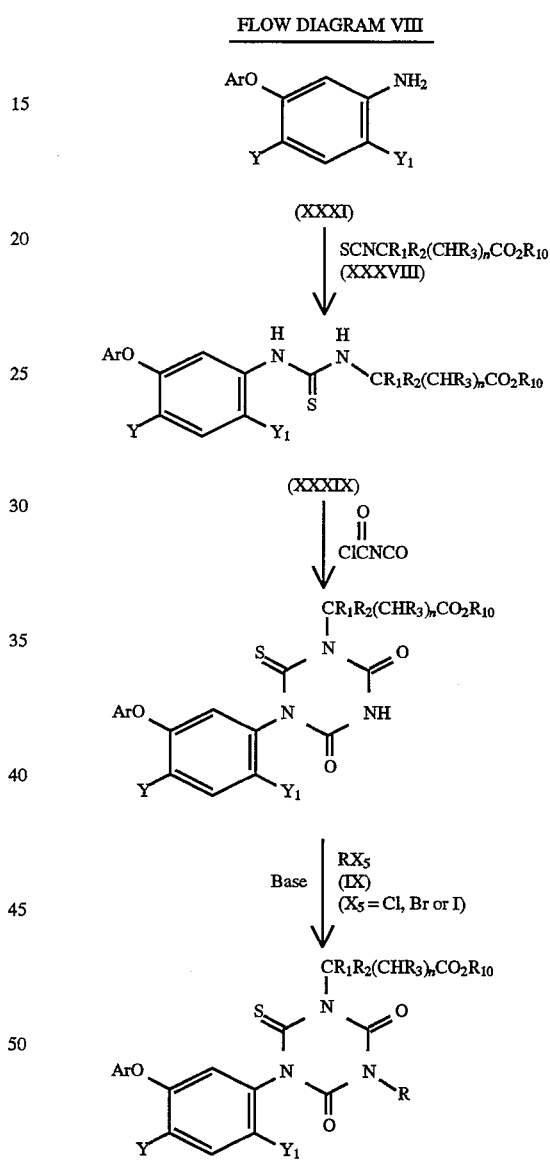

Compounds of formula I wherein A is S, $A_1$ and $A_2$ are O, and V is $CO_2R_{10}$ may be prepared by reacting a compound of formula XXXI with an isothiocyanate of formula XL to form a thiourea of formula XLI, cyclizing the formula XLI compound with N-(chlorocarbonyl) isocyanate to form a 1-(3-aryloxyphenyl)-s-triazine-4,6-dioxo-2-thione compound of formula XLII, and alkylating the formula XLII compound with an alkylating agent of formula XIII and a base to form the desired formula I compound. The reaction scheme is shown in Flow Diagram IX.

FLOW DIAGRAM IX

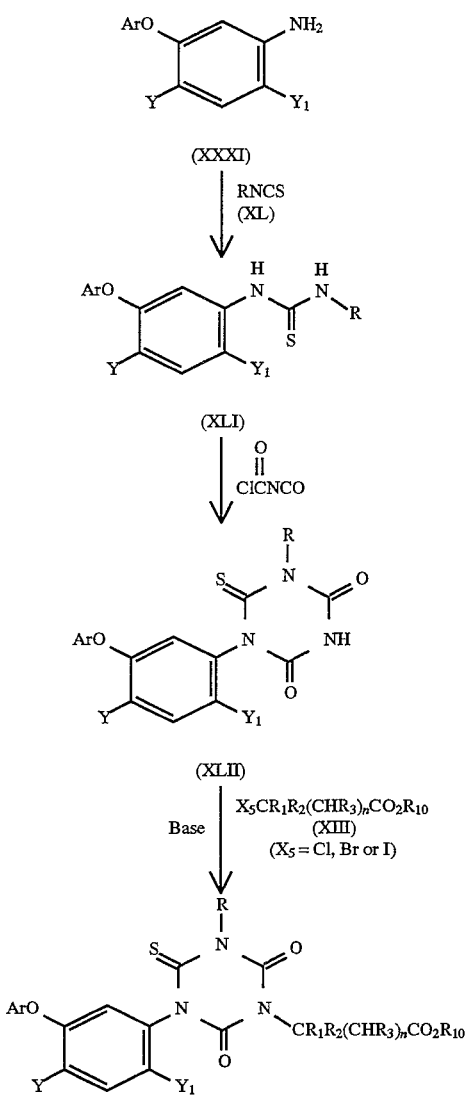

Compounds of formula I wherein $A_1$ and $A_2$ are S, A is O or S and V is $CO_2R_{10}$ may be prepared by reacting a compound of formula XXXIX with an isothiocyanate of formula XL to form an intermediate compound of formula XLIII, and cyclizing the formula XLIII compound with phosgene or thiophosgene to form the desired formula I compound. The reactions are shown below in Flow Diagram X.

FLOW DIAGRAM X

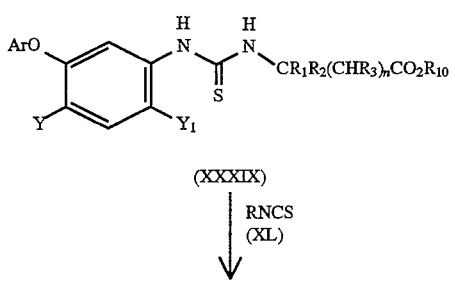

-continued
FLOW DIAGRAM X

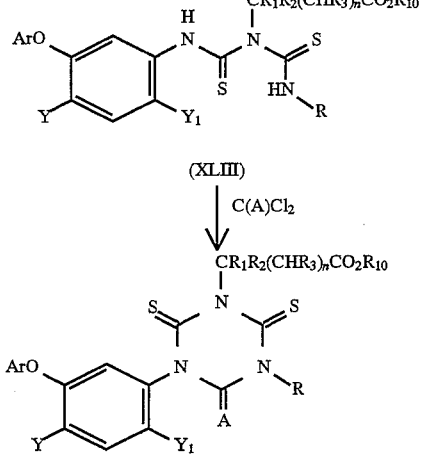

Compounds of formula I wherein A and $A_1$ are S, $A_2$ is O or S and V is $CO_2R_{10}$ may be prepared by reacting a compound of formula XLI with an isothiocyanate of formula XXXVIII to form an intermediate compound of formula XLIV, and cyclizing the formula XLIV compound with phosgene or thiophosgene to form the desired formula I compound. The reaction scheme is shown in Flow Diagram XI.

FLOW DIAGRAM XI

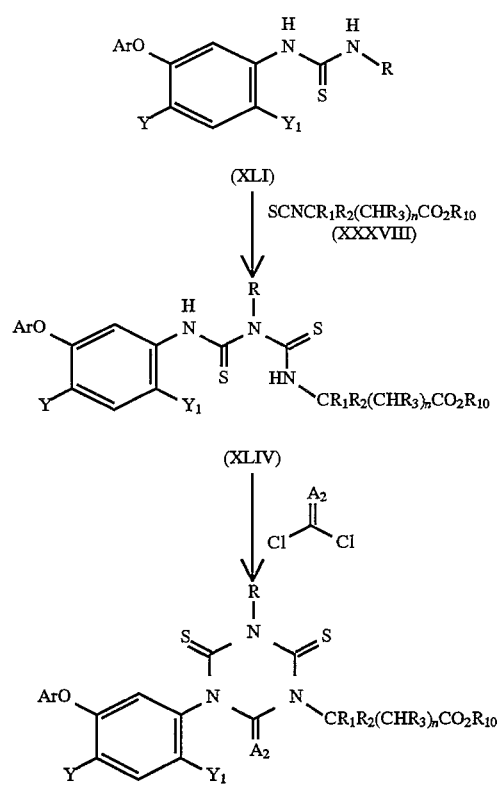

Compounds of formula I wherein A and $A_2$ are S, $A_1$ is O and V is $CO_2R_{10}$ may be prepared by reacting a compound of formula XXXIX with an isocyanate of formula XXXV to form an intermediate compound of formula XLV, and cyclizing the formula XLV compound with thiophosgene to form the desired formula I compound. The reactions are shown in Flow Diagram XII.

FLOW DIAGRAM XII

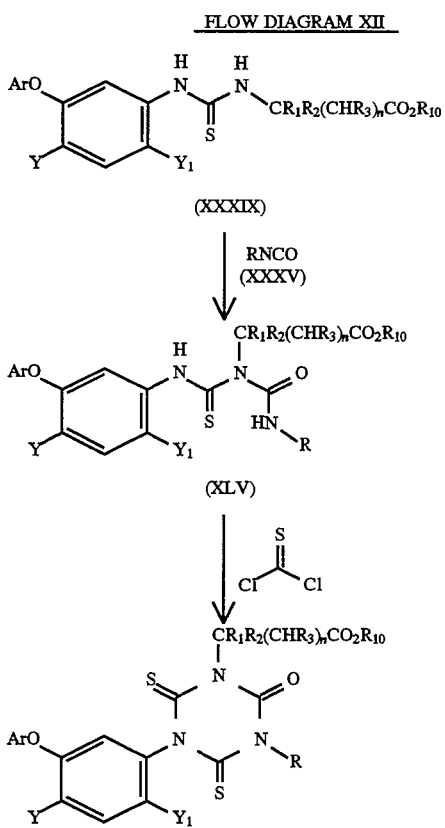

Alternatively, compounds of formula I wherein A and $A_2$ are S, $A_1$ is O and V is $CO_2R_{10}$ may be prepared by reacting a compound of formula XLI with an isocyanate of formula XXXII to form an intermediate compound of formula XLVI, and cyclizing the formula XLVI compound with thiophosgene to form the desired formula I compound. The reaction scheme is shown in Flow Diagram XIII.

FLOW DIAGRAM XIII

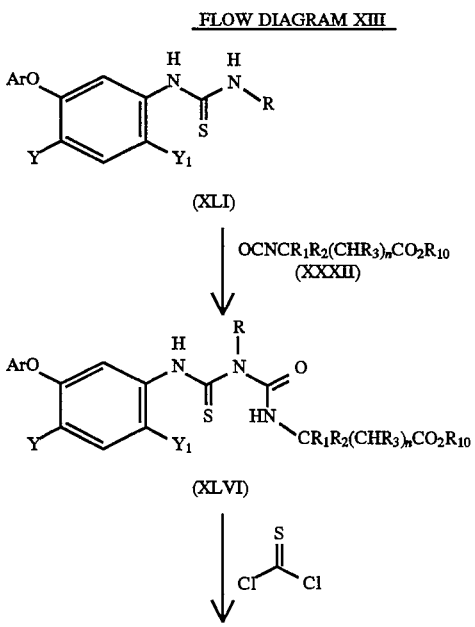

FLOW DIAGRAM XIII -continued

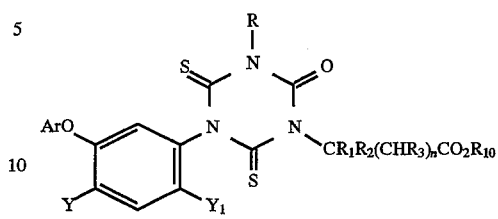

Compounds of formula I wherein $R_6$ is $NR_{11}R_{12}$ may be prepared using standard procedures such as hydrolyzing the appropriate ester of formula XLVII in the presence of trifluoroacetic acid, reacting the resultant acid with thionyl chloride to give the acid chloride of formula XLVIII and reacting the formula XLVIII acid chloride with an amine of formula XLIX optionally in the presence of base to give the desired product. The reactions are shown in Flow Diagram XIV.

FLOW DIAGRAM XIV

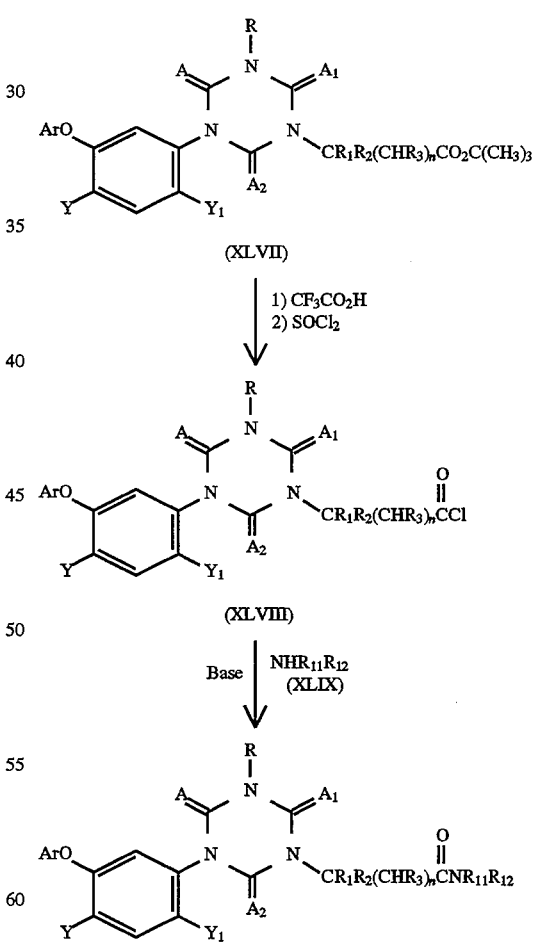

Using the formula XLVIII acid chloride, formula I compounds wherein V is $C(O)R_7$ may be prepared as shown below in Flow Diagram XV.

FLOW DIAGRAM XV

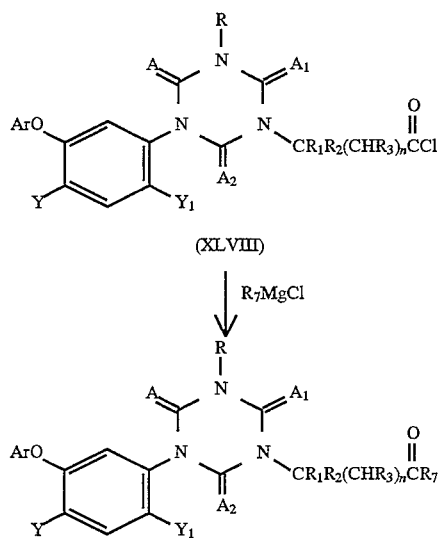

(XLVIII)

Formula I compounds wherein $R_6$ is $SR_{10}$ may be prepared by reacting the formula XLVIII acid chloride with a thiol of formula L. The reaction is shown below in Flow Diagram XVI.

FLOW DIAGRAM XVI

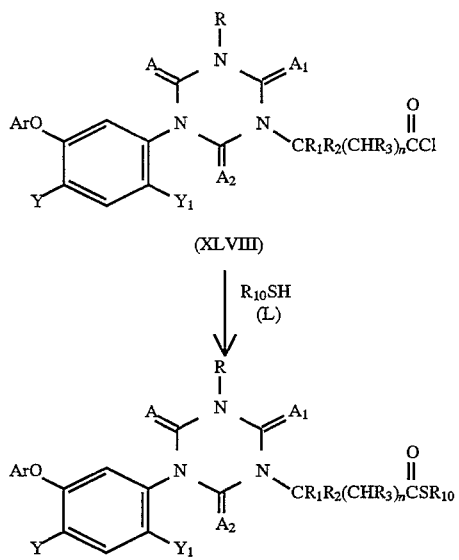

Formula I compounds wherein V is $CH_2OC(O)R_8$ may be prepared by reducing a compound of formula LI to form an alcohol of formula LII, and reacting the formula LII compound with an acid halide of formula LIII in the presence of a base. The reactions are shown below in Flow Diagram XVII.

FLOW DIAGRAM XVII

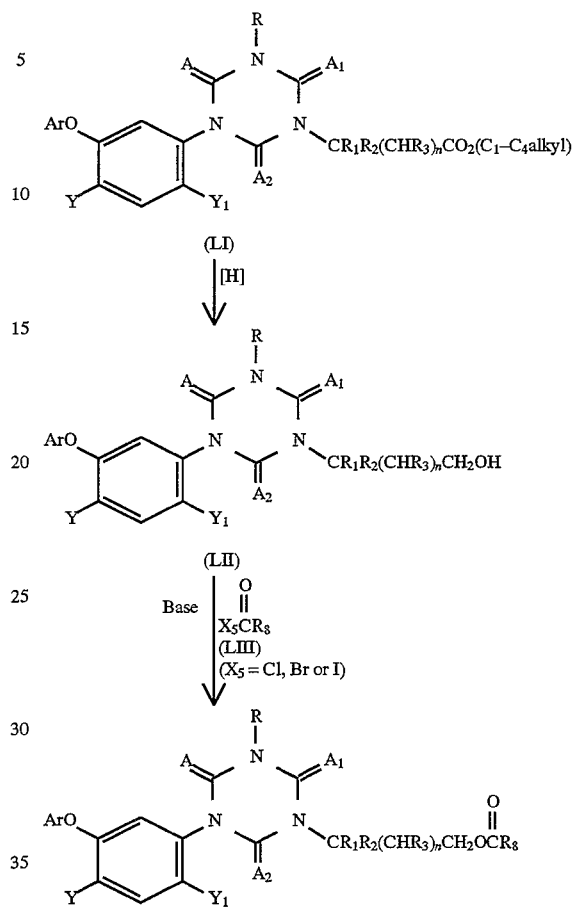

Formula I compounds wherein V is CHO or $CH(OR_9)_2$ may be prepared by reducing the formula LI compound to form an aldehyde of formula LIV, and reacting the formula LIV aldehyde with an alcohol of formula LV in the presence of an acid. The reactions are shown in Flow Diagram XVIII.

FLOW DIAGRAM XVIII

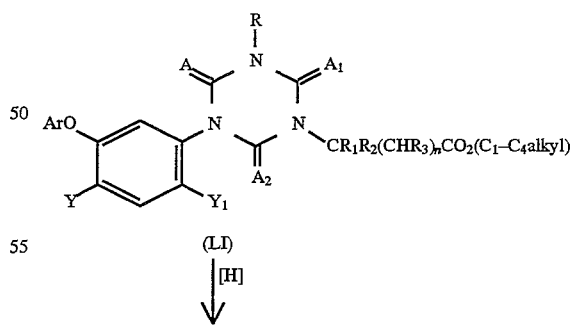

(LI)

FLOW DIAGRAM XVIII -continued

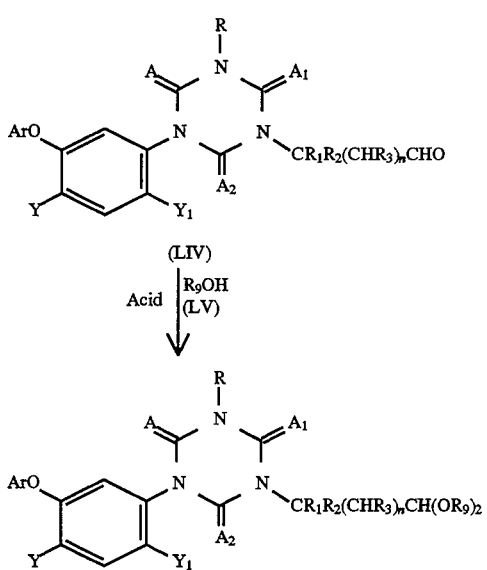

Compounds of formula I wherein V is HC=NOR$_{11}$ may be prepared by reacting the formula LIV aldehyde with an amine of formula LVI. The reaction is shown in Flow Diagram XIX.

FLOW DIAGRAM XIX

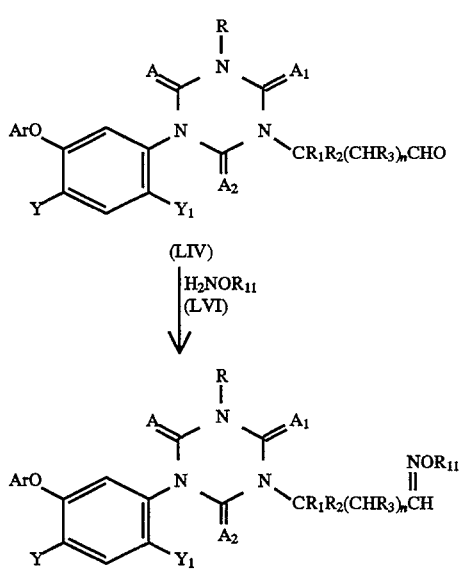

Similarly, compounds of formula I wherein V is HC=NCOR$_{11}$ or HC=NNHCONH$_2$ may be prepared by reacting the formula LIV aldehyde with an amine of formula LVII or a semicarbazide of formula LVIII. The reactions are shown below in Flow Diagram XX.

FLOW DIAGRAM XX

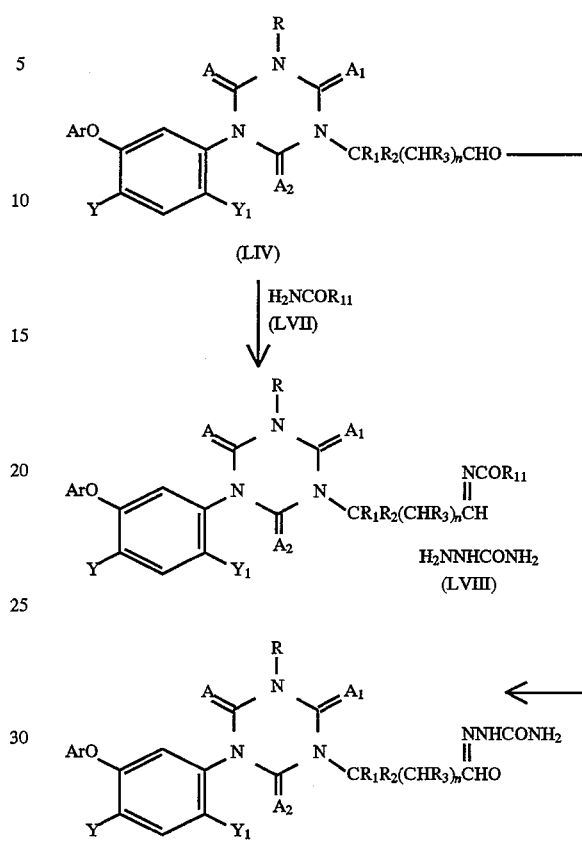

Formula I compounds wherein R$_{10}$ is an alkali metal, alkaline earth metal, manganese, copper, zinc, cobalt, silver, nickel, ammonium or organic ammonium cation, and/or R is an alkali metal, may be prepared from formula I compounds wherein R$_6$ is OH and/or R is hydrogen by conventional processes known to those skilled in the art.

Starting formula XXI and XXVI compounds may be prepared as shown below in Flow Diagram XXI.

FLOW DIAGRAM XXI

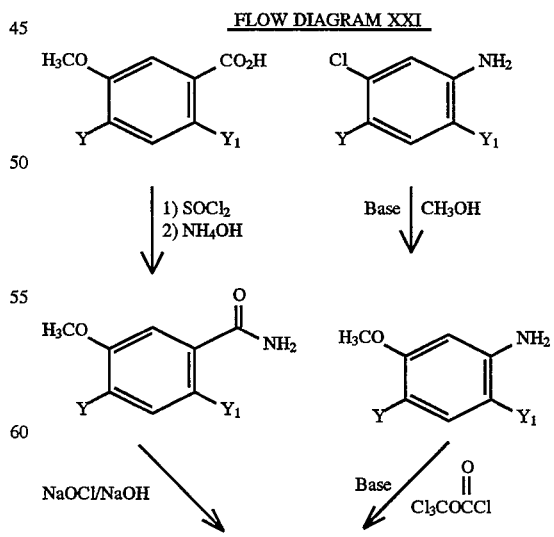

FLOW DIAGRAM XXI -continued
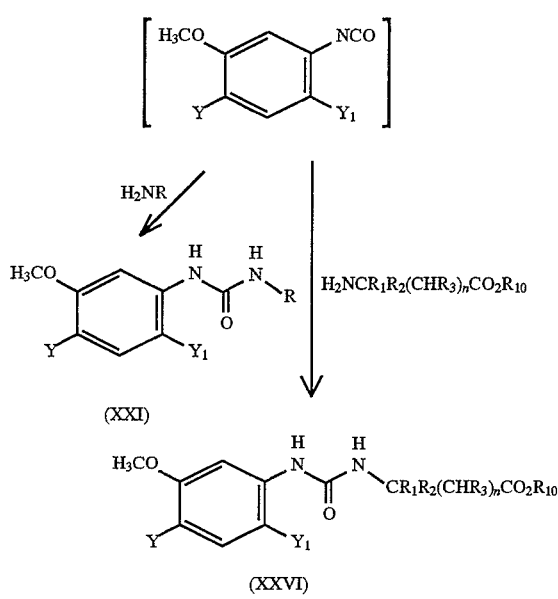
Starting formula XXI compounds wherein Y is hydrogen and $Y_1$ is cyano may be prepared as shown below in Flow Diagram XXII.
FLOW DIAGRAM XXII
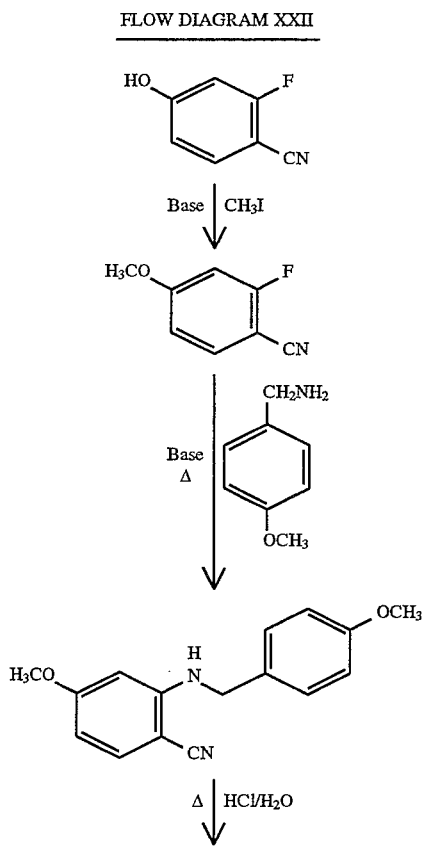
FLOW DIAGRAM XXII -continued
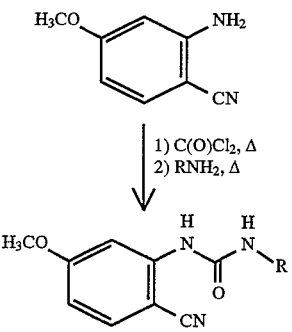
Compounds of formula XXXI, which are described in Flow Diagram VI, may also be prepared as shown in Flow Diagram XXIII.
FLOW DIAGRAM XXIII
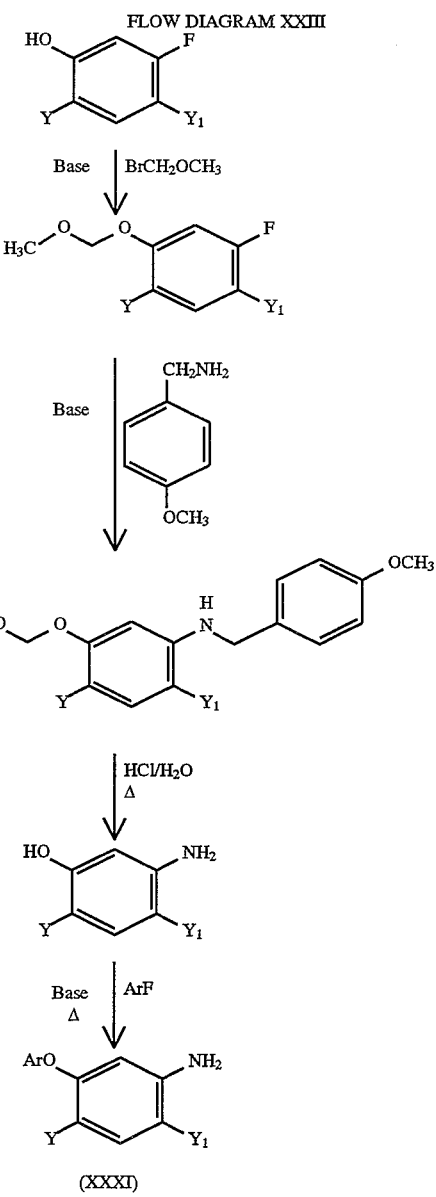

This invention also relates to intermediate compounds which are useful in the preparation of the formula I compounds. The intermediate compounds have the structural formulas LIX, LX and LXI.

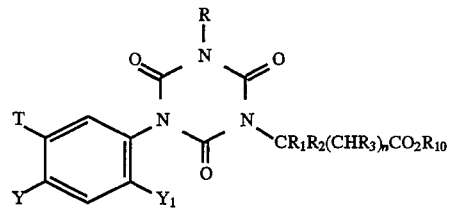
(LIX)

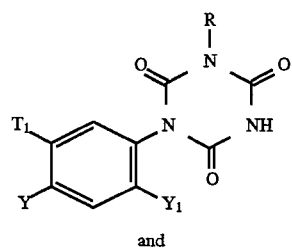
(LX)

and

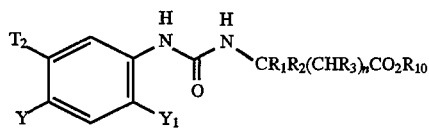
(LXI)

wherein

T is F, OH or OCH$_3$;

T$_1$ is OH or OCH$_3$;

T$_2$ is F, OCH$_3$,

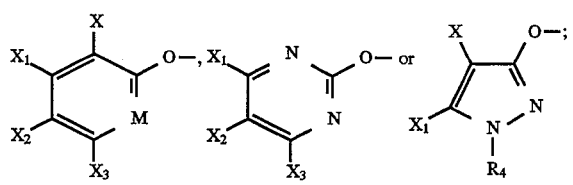

M is CX$_4$ or N;

X, X$_1$, X$_2$, X$_3$, X$_4$ and Y$_1$ are each independently hydrogen, halogen, nitro, cyano or C$_1$–C$_4$haloalkyl;

Y is hydrogen or halogen;

R$_4$ is C$_1$–C$_4$alkyl;

R is hydrogen, C$_1$–C$_4$alkyl, C$_2$–C$_6$alkoxyalkyl, C$_3$–C$_{12}$alkylcarbonylalkyl, C$_3$–C$_{12}$haloalkylcarbonylalkyl, C$_3$–C$_{12}$alkoxycarbonylalkyl, C$_3$–C$_{12}$haloalkoxycarbonyl-alkyl, C$_3$–C$_6$alkenyl or C$_3$–C$_6$alkynyl;

R$_1$, R$_2$ and R$_3$ are each independently hydrogen or C$_1$–C$_4$alkyl;

n is an integer of 0, 1 or 2; and

R$_{10}$ is C$_1$–C$_6$alkyl.

The present invention also relates to intermediate compounds having the structural formula LXI

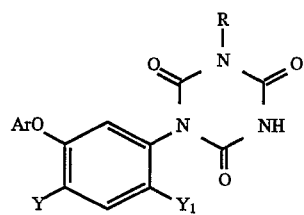
(LXI)

wherein
Ar is

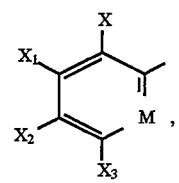

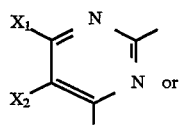 or

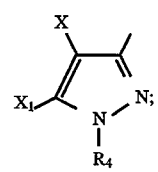

M is CX$_4$ or N;

X, X$_1$, X$_2$, X$_3$, X$_4$ and Y$_1$ are each independently hydrogen, halogen, nitro, cyano or C$_1$–C$_4$haloalkyl;

R$_4$ is C$_1$–C$_4$alkyl; and

R is C$_3$–C$_{12}$alkylcarbonylalkyl, C$_3$–C$_{12}$haloalkylcarbonylalkyl, C$_3$–C$_{12}$alkoxycarbonylalkyl or C$_3$–C$_{12}$haloalkoxycarbonylalkyl.

The formula I compounds of the present invention are effective herbicidal agents useful for the control of a wide variety of undesirable plant species. Those compounds are effective for controlling weeds native to both dry land and wet land areas. The compounds are also useful as aquatic herbicides and are effective in controlling the above-said plants when applied to the foliage thereof or to soil or water containing seeds or other propagating organs thereof such as stolons, tubers or rhizomes, at rates of from about 0.016 to 4.0 kg/ha and preferably from about 0.032 to 2.0 kg/ha.

Advantageously, it has been found that the formula I compounds of the present invention are effective for controlling undesirable plant species including important weeds in transplanted rice culture. The compounds may be applied to the soil or water containing transplanted rice plants and seed or other propagating organs of a variety of weed species.

The formula I compounds of this invention are best suited for use as broad spectrum herbicides, especially when applied postemergence to the locus in which weed control is desired. However, certain compounds of this invention are selective. In fact, some of the compounds of this invention are selective in crops such as soybeans, rice, wheat and corn when applied as preemergence and/or postemergence treatments.

While the formula I compounds of this invention are effective for controlling undesirable plant species when employed alone, they may also be used in combination with other biological chemicals, including other herbicides.

The formula I compounds of this invention may be applied to crops in the form of a solid or liquid herbicidal composition, comprising a herbicidally effective amount of the compound dispersed or dissolved in an agronomically acceptable, inert solid or liquid carrier. The compositions may be applied as preemergence or postemergence treatments.

The formula I compounds may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited by the examples as the full scope of the invention is defined in the claims. The term NMR designates nuclear magnetic resonance spetroscopy.

EXAMPLE 1

Preparation of 5-Fluoro-2-nitrobenzoyl chloride

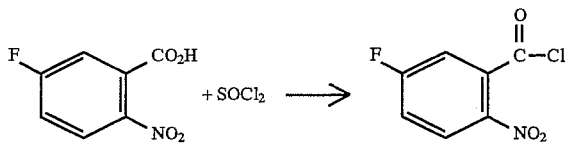

A mixture of 5-fluoro-2-nitrobenzoic acid (47.51 g, 0.257 mol) and thionyl chloride (100 mL, 1.370 mol) is refluxed for several hours and concentrated in vacuo to give the title product which is used in Example 2 without further purification.

Using essentially the same procedure, but using the appropriately substituted benzoic acid, the following compounds are obtained:

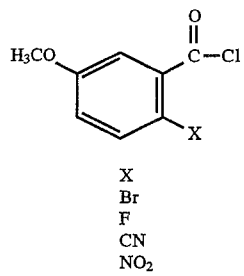

X
Br
F
CN
NO$_2$

EXAMPLE 2

Preparation of 5-Fluoro-2-nitrobenzoyl azide

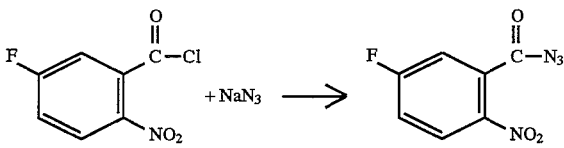

A solution of 5-fluoro-2-nitrobenzoyl chloride (52 g, 0.256 mol) in a toluene (50 mL) and acetone (60 mL) mixture is added dropwise to a solution of sodium azide (19.55 g, 0.301 mol) in water while maintaining the reaction mixture temperature below 30° C. The resultant solid is collected and the filtrate is extracted with ether. The organic extracts are combined, washed with water, dried over anhydrous magnesium sulfate and concentrated by blowing air over the solution to obtain additional solids. The solids are combined, slurried in an acetone/water (1:3) solution, filtered and dried to give the title product as a yellow solid.

EXAMPLE 3

Preparation of N-[(5-Fluoro-2-nitrophenyl) carbamoyl]glycine methyl ester

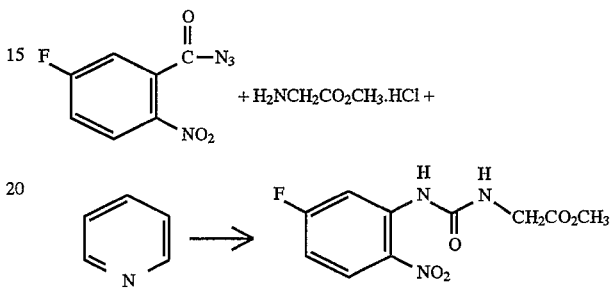

A solution of 5-fluoro-2-nitrobenzoyl azide (5.46 g, 0.026 mol) in toluene is stirred at 65° C. for 90 minutes, cooled, treated with glycine methyl ester hydrochloride (3.63 g, 0.029 mol), stirred for 10 minutes, treated with pyridine (5 mL, 0.062 mol), stirred overnight, diluted with water and extracted with ethyl acetate. The organic extracts are combined, washed sequentially with water, 0.4M hydrochloric acid and brine, dried over anhydrous magnesium sulfate and concentrated in vacuo to obtain a solid. The solid is slurried in an ether/hexanes (6:4) solution, filtered and dried to give a yellow solid. Column chromatography of the yellow solid using silica gel and ethyl acetate in hexanes solutions gives the title product as a yellow solid, mp 133.2°–135.3° C.

EXAMPLE 4

Preparation of N-[(4,5-Difluoro-2-nitrophenyl) carbamoyl]glycine methyl ester

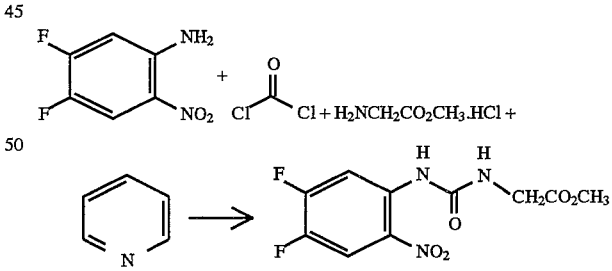

A solution of 4,5-difluoro-2-nitroaniline (1.07 g, 6.15 mmol) in tetrahydrofuran is cooled to 2° C., treated with phosgene (3.8 mL, 1.93M, 7.33 mmol), stirred at ice-bath temperature for 2 hours, treated with glycine methyl ester hydrochloride (1.02 g, 8.12 mmol), treated with pyridine (1 mL, 12.64 mmol), stirred at room temperature for 3 days, diluted with concentrated ammonia solution and water, and extracted with ethyl acetate. The organic extracts are combined, washed sequentially with water and brine, dried over anhydrous magnesium sulfate and concentrated in vacuo to obtain a residue. Column chromatography of the residue using silica gel and an ethyl acetate/hexanes (1:3) solution gives the title product as a solid, mp 118.9°–122.9° C.

EXAMPLE 5

Preparation of Methyl 3-(5-fluoro-2-nitrophenyl) tetrahydro-2,4,6-trioxo-s-triazine-1(2H)-acetate

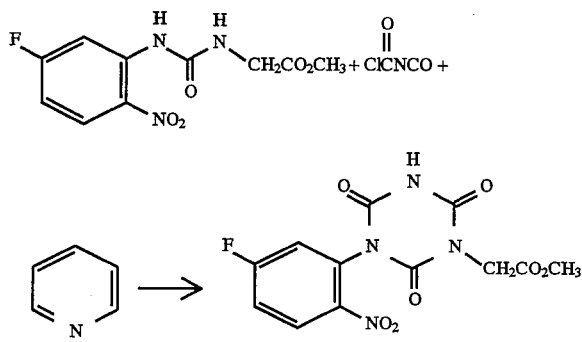

A solution of N-[(5-fluoro-2-nitrophenyl)carbamoyl] glycine methyl ester (20.47 g, 75.46 mmol) in methylene chloride is cooled in an ice-bath, treated with N-(chlorocarbonyl) isocyanate (7 mL, 86.94 mmol), treated dropwise with pyridine (7.5 mL, 92.92 mmol), warmed to and stirred at room temperature for 90 minutes, and filtered. The filtrate is poured into 0.11M hydrochloric acid (450 mL), the phases are separated and the aqueous phase is extracted with methylene chloride. The organic phase and extracts are combined, washed with brine, dried over anhydrous magnesium sulfate and concentrated in vacuo to obtain the title product as a yellow solid.

Using essentially the same procedure, but substituting N-[(4,5-difluoro-2-nitrophenyl)carbamoyl]glycine methyl ester for N-[(5-fluoro-2-nitrophenyl)carbamoyl]glycine methyl ester, methyl 3-(4,5-difluoro-2-nitrophenyl) tetrahydro-2,4,6-trioxo-s-triazine-1(2H)-acetate is obtained as a yellow oil.

EXAMPLE 6

Preparation of Methyl 3-[5-(2,4-dichlorophenoxy)-2-nitrophenyl]tetrahydro-2,4,6-trioxo-s-triazine-1(2H)-acetate

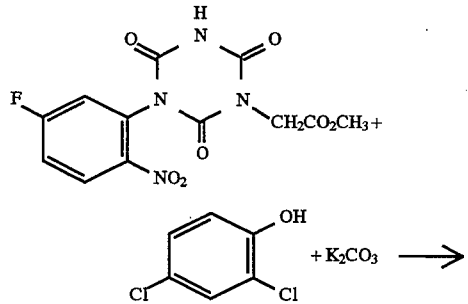

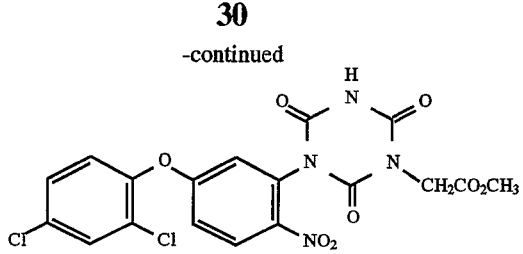

Potassium carbonate (1.14 g, 8.25 mmol) is added to a solution of methyl 3-(5-fluoro-2-nitrophenyl)tetrahydro-2,4,6-trioxo-s-triazine-1(2H)-acetate (0.93 g, 2.74 mmol) and 2,4-dichlorophenol (0.66 g, 4.07 mmol) in N,N-dimethylformamide at 38° C. The reaction mixture is stirred at 38° C. for 3 days, cooled to room temperature and poured into 1M hydrochloric acid. The aqueous mixture is extracted with ethyl acetate. The organic extracts are combined, washed sequentially with water and brine, dried over anhydrous magnesium sulfate and concentrated in vacuo to obtain an orange oil. Column chromatography of the oil using silica gel and 30% to 40% ethyl acetate in hexanes solutions gives the title product as a yellow foam which is identified by NMR spectral analysis.

EXAMPLE 7

Preparation of Methyl 3-[5-(2,4-dichlorophenoxy)-2-nitrophenyl]tetrahydro-5-methyl-2,4,6-trioxo-s-triazine-1(2H)-acetate

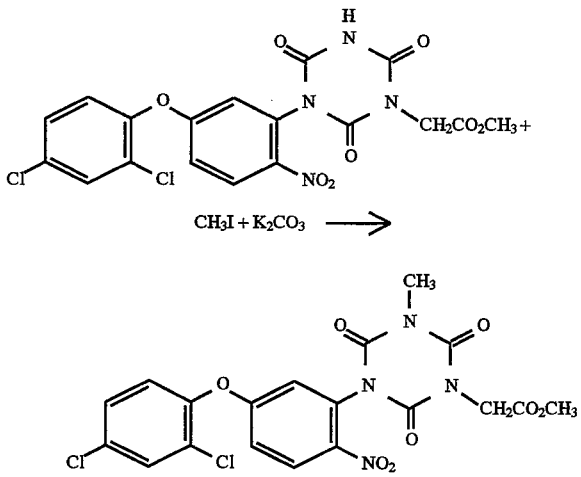

Methyl iodide (0.15 mL, 2.41 mmol) and potassium carbonate (0.19 g, 1.34 mmol) are added to a solution of methyl 3-[5-(2,4-dichlorophenoxy)-2-nitrophenyl] tetrahydro-2,4,6-trioxo-s-triazine-1(2H)-acetate (0.40 g, 0.83 mmol) in N,N-dimethylformamide. The reaction mixture is stirred overnight at room temperature and poured into a saturated ammonium chloride solution. The aqueous mixture is extracted with ethyl acetate. The organic extracts are combined, washed sequentially with water and brine, dried over anhydrous magnesium sulfate and concentrated in vacuo to obtain a yellow oil. Column chromatography of the oil using silica gel and an ethyl acetate/hexanes (1:3) solution gives the title product as a yellow foam which is identified by NMR spectral analysis.

Using essentially the same procedure, the following compounds are obtained:

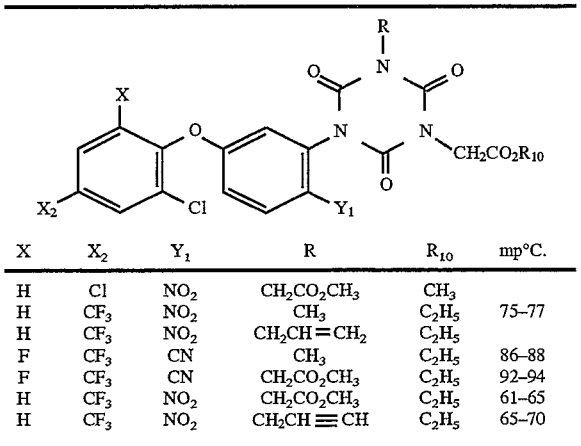

| X | X₂ | Y₁ | R | R₁₀ | mp°C. |
|---|---|---|---|---|---|
| H | Cl | NO₂ | CH₂CO₂CH₃ | CH₃ | |
| H | CF₃ | NO₂ | CH₃ | C₂H₅ | 75–77 |
| H | CF₃ | NO₂ | CH₂CH=CH₂ | C₂H₅ | |
| F | CF₃ | CN | CH₃ | C₂H₅ | 86–88 |
| F | CF₃ | CN | CH₂CO₂CH₃ | C₂H₅ | 92–94 |
| H | CF₃ | NO₂ | CH₂CO₂CH₃ | C₂H₅ | 61–65 |
| H | CF₃ | NO₂ | CH₂CH≡CH | C₂H₅ | 65–70 |

EXAMPLE 8

Preparation of Methyl 3-(5-fluoro-2-nitrophenyl)tetrahydro-5-methyl-2,4,6-trioxo-s-triazine-1(2H)-acetate

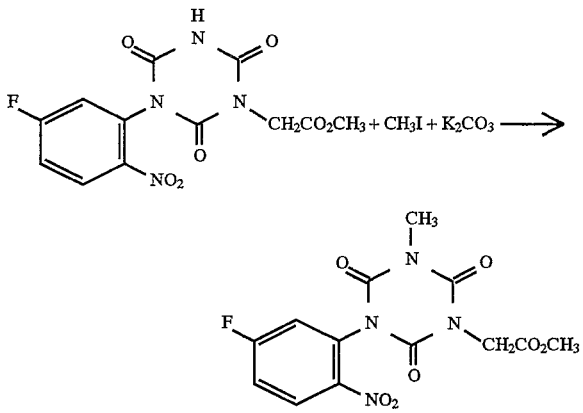

Methyl iodide (5.0 mL, 80.31 mmol) and potassium carbonate (11.12 g, 80.45 mmol) are added to a solution of methyl 3-(5-fluoro-2-nitrophenyl)tetrahydro-2,4,6-trioxo-s-triazine-1(2H)-acetate (25.65 g, 75.40 mmol) in N,N-dimethylformamide. The reaction mixture is stirred at room temperature overnight, concentrated in vacuo and poured into water. The aqueous mixture is extracted with ethyl acetate. The organic extracts are combined, washed sequentially with water, 0.08M sodium metabisulfite solution and brine, dried over anhydrous magnesium sulfate and concentrated in vacuo to obtain a yellow oil. The oil is dissolved in a refluxing ethyl acetate/ether (1:1) solution and the resultant solution is chilled and treated dropwise with hexanes to obtain a solid. The solid is collected, washed with an ether/ethyl acetate/hexanes (1:1:8) solution and dried overnight in vacuo at 50° C. to give the title product as a solid, mp 121.8°–122.3° C.

Using essentially the same procedure, but substituting methyl 3-(4,5-difluoro-2-nitrophenyl)tetrahydro-2,4,6-trioxo-s-triazine-1(2H)-acetate for methyl 3-(5-fluoro-2-nitrophenyl)tetrahydro-2,4,6-trioxo-s-triazine-1(2H)-acetate, methyl 3-(4,5-difluoro-2-nitrophenyl)tetrahydro-5-methyl-2,4,6-trioxo-s-triazine-1(2H)-acetate is obtained.

EXAMPLE 9

Preparation of Methyl 3-{5-[(2,4-dichloro-m-tolyl)oxy]-2-nitrophenyl}tetrahydro-5-methyl-2,4,6-trioxo-s-triazine-1(2H)-acetate

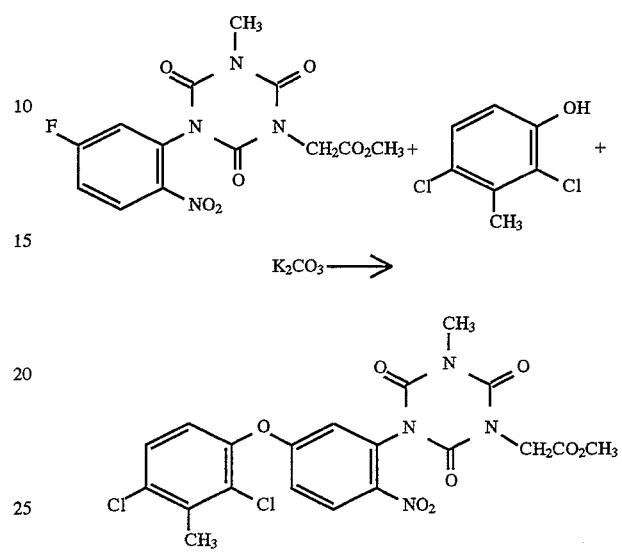

A mixture of methyl 3-(5-fluoro-2-nitrophenyl)tetrahydro-5-methyl-2,4,6-trioxo-s-triazine-1(2H)-acetate (0.51 g, 1.4 mmol), 2,4-dichloro-3-methylphenol (0.33 g, 1.9 mmol) and potassium carbonate (0.28 g, 2.0 mmol) in N,N-dimethylformamide is stirred overnight at room temperature and poured into water. The aqueous mixture is extracted with ethyl acetate. The organic extracts are combined, washed sequentially with water, 1M sodium hydroxide solution, water and brine, dried over anhydrous magnesium sulfate and concentrated in vacuo to obtain a yellow solid. The solid is slurried with an ether/hexanes (1:1) solution, filtered and dried in vacuo to give the title product as a yellow solid, mp 199.9°–202° C.

Using essentially the same procedure, but using the appropriately substituted phenol, the following compounds are obtained:

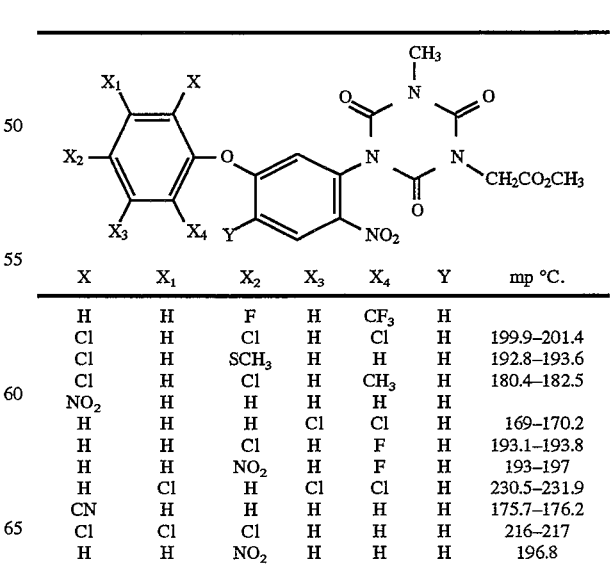

| X | X₁ | X₂ | X₃ | X₄ | Y | mp °C. |
|---|---|---|---|---|---|---|
| H | H | F | H | CF₃ | H | |
| Cl | H | Cl | H | Cl | H | 199.9–201.4 |
| Cl | H | SCH₃ | H | H | H | 192.8–193.6 |
| Cl | H | Cl | H | CH₃ | H | 180.4–182.5 |
| NO₂ | H | H | H | H | H | |
| H | H | H | Cl | Cl | H | 169–170.2 |
| H | H | Cl | H | F | H | 193.1–193.8 |
| H | H | NO₂ | H | F | H | 193–197 |
| H | Cl | H | Cl | Cl | H | 230.5–231.9 |
| CN | H | H | H | H | H | 175.7–176.2 |
| Cl | Cl | Cl | H | H | H | 216–217 |
| H | H | NO₂ | H | H | H | 196.8 |

-continued

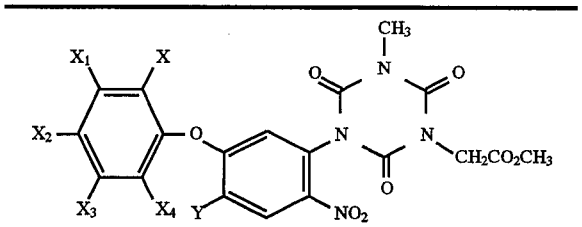

| X | X₁ | X₂ | X₃ | X₄ | Y | mp °C. |
|---|----|----|----|----|---|--------|
| F | F | F | H | H | H | 160.2–166.4 |
| H | OCH₃ | Cl | H | Cl | H | 207.3–207.7 |
| H | F | F | H | F | H | 142.2–144.2 |
| H | Cl | Cl | H | Cl | H |  |
| H | H | CN | H | H | H | 210.7 |
| H | Cl | H | Cl | H | H |  |
| Cl | H | H | H | Cl | H |  |
| H | H | Cl | H | H | H | 191.2–192 |
| Cl | H | H | H | H | H | 161.3–168.4 |
| Cl | H | Cl | H | H | F |  |

EXAMPLE 10

Preparation of Methyl 3-{[2-chloro-4-(methylsulfinyl)phenoxy]-2-nitrophenyl}tetrahydro-5-methyl-2,4,6-trioxo-s-triazine-1(2H)-acetate

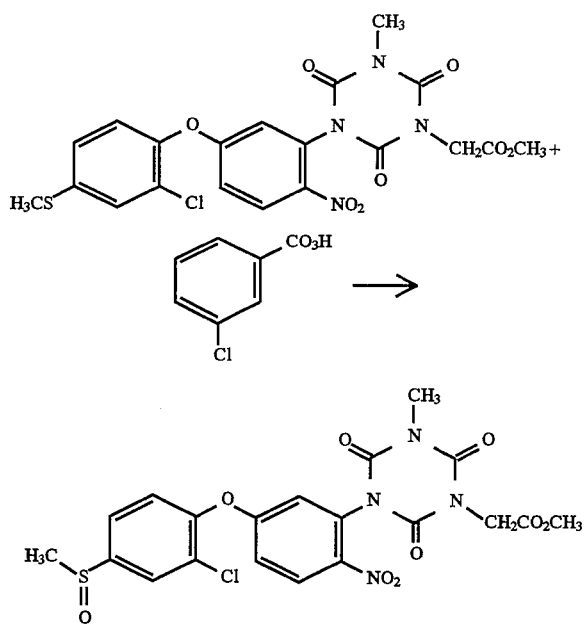

3-Chloroperoxybenzoic acid (0.17 g, 0.77 mmol) is added to a solution of methyl 3-{5-[2-chloro-4-(methylthio) phenoxy]-2-nitrophenyl}tetrahydro-5-methyl-2,4,6-trioxo-s-triazine-1(2H)-acetate (0.29 g, 0.56 mmol) in methylene chloride which is previously cooled in an ice-bath. The reaction mixture is stirred at ice-bath temperature for 90 minutes, quenched with sodium metabisulfite solution (0.2M, 10 mL) and poured into saturated sodium bicarbonate solution. The aqueous mixture is concentrated in vacuo to remove methylene chloride, cooled and extracted with ethyl acetate. The organic extracts are combined, washed sequentially with water and brine, dried over anhydrous magnesium sulfate and concentrated in vacuo to obtain a yellow oil. Column chromatography of the oil using silica gel and a 2% methanol in methylene chloride solution gives the title product as a white foam which is identified by NMR spectral analysis.

EXAMPLE 11

Preparation of Methyl tetrahydro-3-methyl-5-[2-nitro-5-(2-pyridyloxy)phenyl]-2,4,6-trioxo-s-triazine-1(2H)-acetate

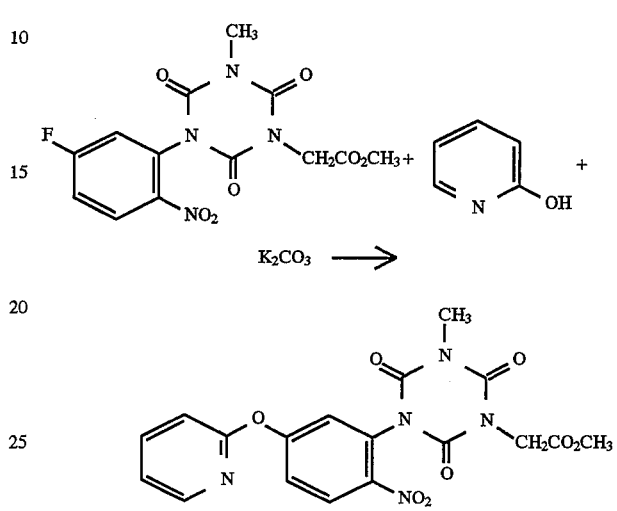

A mixture of methyl 3-(5-fluoro-2-nitrophenyl) tetrahydro-5-methyl-2,4,6-trioxo-s-triazine-1(2H)-acetate (0.55 g, 1.55 mmol), 2-hydroxypyridine (0.25 g, 2.58 mmol) and potassium carbonate (0.37 g, 2.64 mmol) in N,N-dimethylformamide is stirred at room temperature overnight and poured into water. The aqueous mixture is extracted with ethyl acetate. The organic extracts are combined, washed sequentially with water, 0.2M sodium hydroxide solution, water and brine, dried over anhydrous magnesium sulfate and concentrated in vacuo to obtain a yellow foam. Column chromatography of the foam using silica gel and a 2% methanol in methylene chloride solution gives the title product as a yellow oil which is identified by NMR spectral analysis.

EXAMPLE 12

Preparation of 5-Methoxy-2-nitrobenzaldehyde

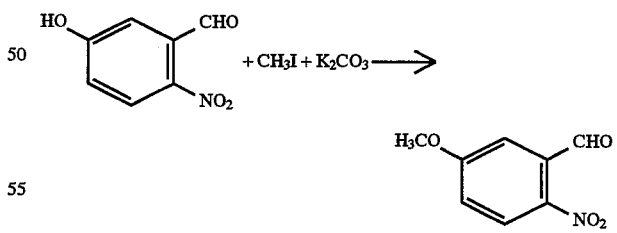

Methyl iodide (23.34 g, 0.165 mol) and potassium carbonate (22.73 g, 0.165 mol) are added to a solution of 5-hydroxy-2-nitrobenzaldehyde (25 g, 0.149 mol) in N,N-dimethylformamide. The reaction mixture is stirred at room temperature for 18 hours and poured into water. The resultant aqueous mixture is extracted with ethyl acetate. The organic extracts are combined, washed with brine, dried over anhydrous sodium sulfate and concentrated in vacuo to give the title product as a brown solid, mp 89°–90° C.

EXAMPLE 13

Preparation of 5-Methoxy-2-nitrobenzoic acid

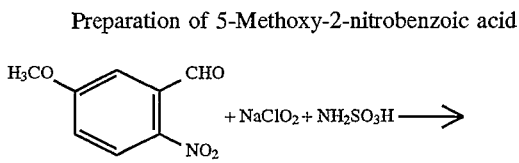

Sulfamic acid (15.73 g, 0.162 mol) is added to a solution of 5-methoxy-2-nitrobezaldehyde (19.6 g, 0.108 mol) in an acetone/water (1:1) mixture. Sodium chlorite (18.31 g, 80% real, 0.162 mol) is then added to the reaction mixture at a rate which maintains the reaction mixture temperature below 40° C. The resultant reaction mixture is stirred at room temperature for 24 hours and poured into water. The aqueous mixture is extracted with ethyl acetate. The organic extracts are combined, washed sequentially with 2N hydrochloric acid and brine, dried over anhydrous magnesium sulfate and concentrated in vacuo to give the title product as a yellow solid.

Using essentially the same procedure, but substituting 2-fluoro-5-methoxybenzaldehyde for 5-methoxy-2-nitrobezaldehyde, 2-fluoro-5-methoxybenzoic acid is obtained as a white solid, mp 144°–146° C.

EXAMPLE 14

Preparation of 5-Methoxy-2-nitrobenzoyl chloride

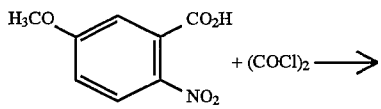

A mixture of 5-methoxy-2-nitrobenzoic acid (15.8 g, 0.08 mol), oxalyl chloride (25 g, 0.197 mol) and N,N-dimethylformamide (2 drops) is stirred at reflux for 4 hours, cooled, stirred at room temperature under nitrogen for several days and concentrated in vacuo to give the title product as a yellow oil which is identified by ¹HNMR spectral analysis.

Using essentially the same procedure, but substituting 2-cyano-5-methoxybenzoic acid for 5-methoxy-2-nitrobenzoic acid, 2-cyano-5-methoxybenzoyl chloride is obtained as a solid, mp 192°–194° C.

EXAMPLE 15

Preparation of 2-Bromo-5-methoxybenzamide

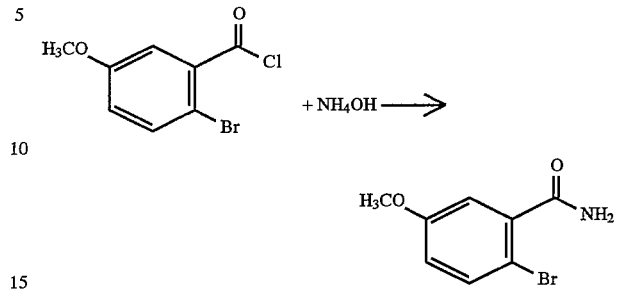

A 30% ammonium hydroxide solution (56 mL) is added dropwise to a solution of 2-bromo-5-methoxybenzoyl chloride in methylene chloride at 0° C. After the addition is complete, the reaction mixture is filtered to obtain a solid which is air-dried and recrystallized from a methanol/water solution to give the title product as a white solid, mp 158°–159° C.

Using essentially the same procedure, but employing the appropriately substituted benzoyl chloride, the following compounds are obtained:

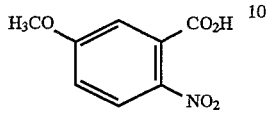

| $Y_1$ | mp°C. |
|---|---|
| $NO_2$ | 145–150 |
| F | 120–124 |
| CN | 214–218 |

EXAMPLE 16

Preparation of 1-(2-Bromo-5-methoxyphenyl)-3-methylurea

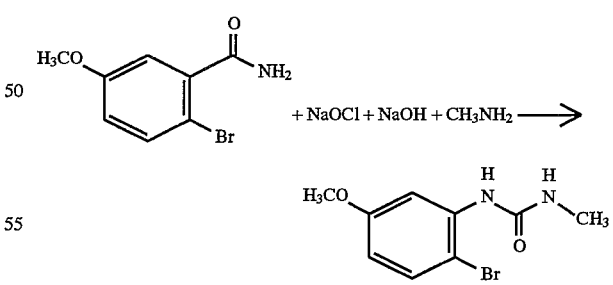

A mixture of 2-bromo-5-methoxybenzamide (16 g, 0.070 mol) in methanol is cooled to 0° C., treated with a mixture of 50% sodium hydroxide solution (7 g) and 5% sodium hypochlorite solution (130 mL), stirred at 0° C. for 10 minutes, treated with 40% methylamine solution (17.81 mL), stirred at 60° C. for 9 hours, cooled and filtered to obtain a solid. The solid is washed with water and air-dried to give the title product as a white solid, mp 164°–166° C.

Using essentially the same procedure, but using the appropriately substituted benzamide, the following compounds are obtained:

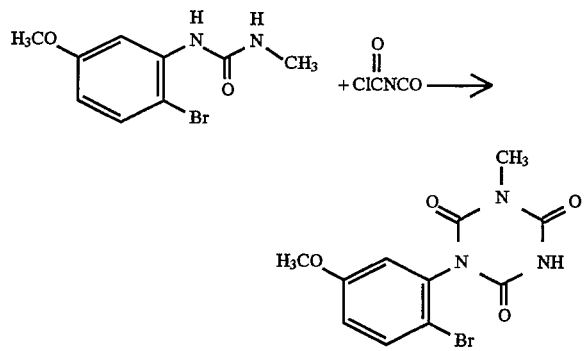

| $Y_1$ | mp°C. |
|---|---|
| $NO_2$ | 209–211 |
| F | 142–145 |

EXAMPLE 17

Preparation of 1-(2-Bromo-5-methoxyphenyl)-3-methyl-s-triazine-2,4,6(1H,3H,5H)-trione

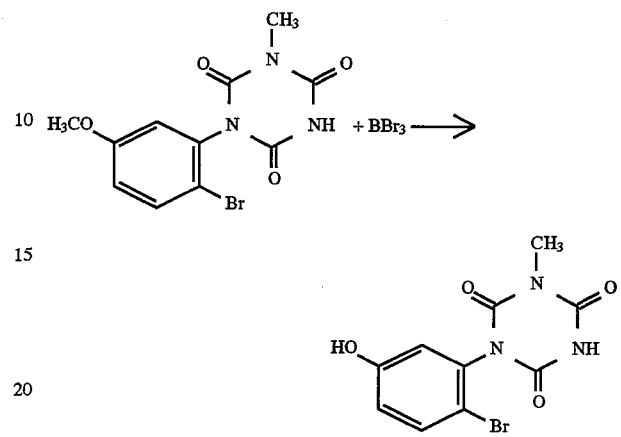

N-(Chlorocarbonyl) isocyanate (6.85 g, 0.065 mol) is added dropwise to a mixture of 1-(2-bromo-5-methoxyphenyl)-3-methylurea (13.4 g, 0.052 mol) in toluene. The reaction mixture is stirred at 60° C. for 2 hours, cooled, stirred overnight at room temperature and filtered to obtain a solid. The solid is washed with ether and air-dried to give the title product as a white solid, mp 185°–187° C.

Using essentially the same procedure, but using the appropriately substituted urea, the following compounds are obtained:

| $Y_1$ | mp°C. |
|---|---|
| $NO_2$ | 185–188 |
| F | 210–212 |

EXAMPLE 18

Preparation of 1-(2-Bromo-5-hydroxyphenyl)-3-methyl-s-triazine-2,4,6(1H,3H,5H)-trione A solution of boron tribromide in methylene chloride (98.75 mL of a 1M solution in methylene chloride) is added to a mixture of 1-(2-bromo-5-methoxyphenyl)-3-methyl-s-triazine-2,4,6(1H,3H,5H)-trione (14.4 g, 0.438 mol) in methylene chloride at 0° C. The reaction mixture is stirred at room temperature for 1 hour and filtered to obtain a solid. The solid is washed with water and air-dried to give the title product as a white solid, mp 265°–270° C.

Using essentially the same procedure, but using the appropriately substituted triazine-2,4,6-trione, the following compounds are obtained:

| $Y_1$ |
|---|
| $NO_2$ |
| F |

EXAMPLE 19

Preparation of 1-{2-Bromo-5-[3-chloro-5-(trifluoromethyl)-2-pyridyloxy]phenyl}-3-methyl-s-triazine-2,4,6(1H,3H,5H)-trione

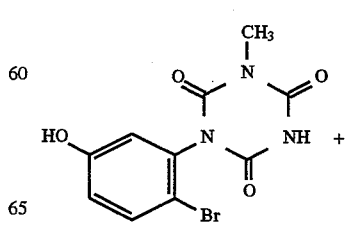

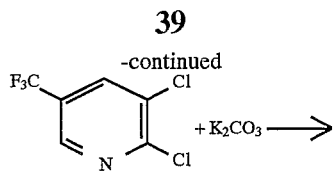

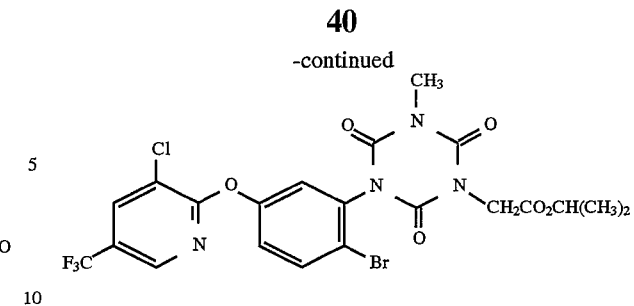

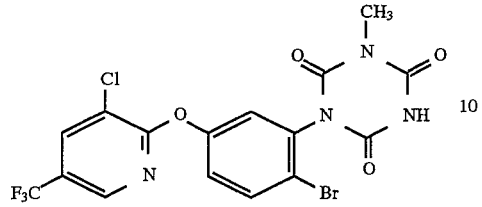

A mixture of 1-(2-bromo-5-hydroxyphenyl)-3-methyl-s-triazine-2,4,6(1H,3H,5H)-trione (5.29 g, 0.0168 mol), 2,3-dichloro-5-trifluoromethylpyridine (5.44 g, 0.025 mol) and potassium carbonate (3.45 g, 0.025 mol) in N,N-dimethylformamide is stirred at 80° C. for 18 hours, cooled to room temperature and poured into water. The aqueous mixture is extracted with ethyl acetate. The organic extracts are combined, washed with brine, dried over anhydrous magnesium sulfate and concentrated in vacuo to obtain a solid. The solid is recrystallized from an ether/hexanes solution to give the title product as a yellow solid, mp 97°–110° C.

Using essentially the same procedure, but using the appropriately substituted fluorobenzene or chloropyridine, the following compounds are obtained:

A mixture of 1-{2-bromo-5-[3-chloro-5-(trifluoromethyl)-2-pyridyloxy]phenyl}-3-methyl-s-triazine-2,4,6-(1H,3H,5H)-trione (0.99 g, 2.01 mmol), isopropyl bromoacetate (0.54 g, 2.98 mmol) and potassium carbonate (0.41 g, 2.97 mmol) in N,N-dimethylformamide is stirred overnight at room temperature and poured into water. The aqueous mixture is filtered to obtain a solid which is air dried to give the title product as a white solid, mp 60°–65° C.

Using essentially the same procedure, but using the appropriately substituted 3-methyl-s-triazine-2,4,6(1H,3H,5H)-trione and the appropriate electrophile, the following compounds are obtained:

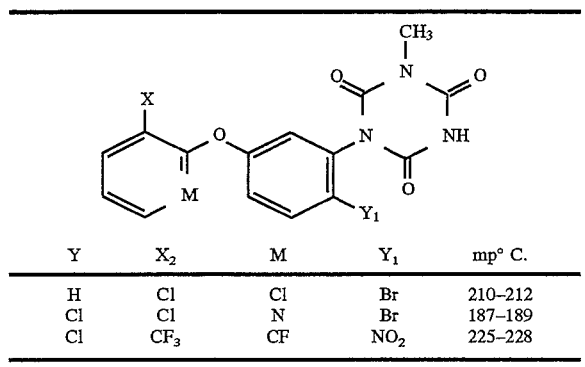

| Y  | $X_2$ | M  | $Y_1$ | mp° C.  |
|----|-------|----|-------|---------|
| H  | Cl    | Cl | Br    | 210–212 |
| Cl | Cl    | N  | Br    | 187–189 |
| Cl | $CF_3$| CF | $NO_2$| 225–228 |

EXAMPLE 20

Preparation of Isopropyl 3-{[2-bromo-5-{[3-chloro-5-(trifluoromethyl)-2-pyridyl]oxy}phenyl}tetrahydro-5-methyl-2,4,6-trioxo-s-triazine-1(2H)-acetate

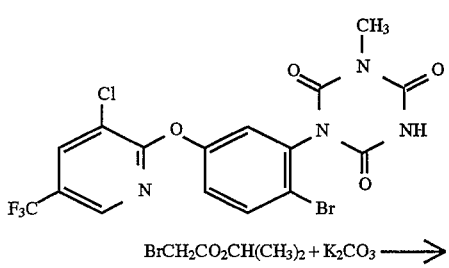

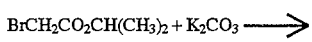

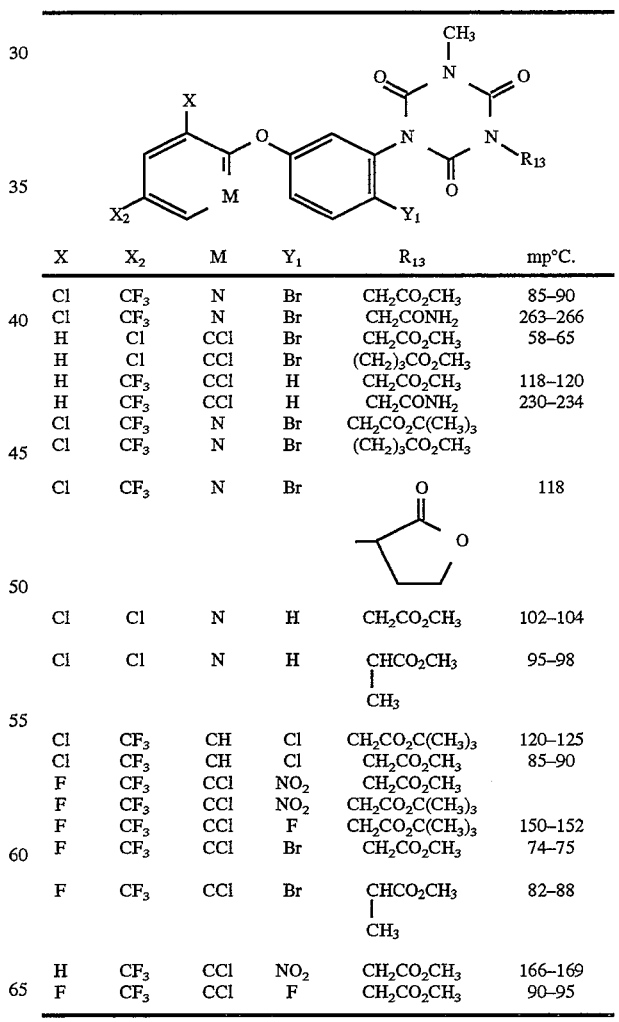

| X  | $X_2$  | M   | $Y_1$  | $R_{13}$           | mp°C.   |
|----|--------|-----|--------|--------------------|---------|
| Cl | $CF_3$ | N   | Br     | $CH_2CO_2CH_3$     | 85–90   |
| Cl | $CF_3$ | N   | Br     | $CH_2CONH_2$       | 263–266 |
| H  | Cl     | CCl | Br     | $CH_2CO_2CH_3$     | 58–65   |
| H  | Cl     | CCl | Br     | $(CH_2)_3CO_2CH_3$ |         |
| H  | $CF_3$ | CCl | H      | $CH_2CO_2CH_3$     | 118–120 |
| H  | $CF_3$ | CCl | H      | $CH_2CONH_2$       | 230–234 |
| Cl | $CF_3$ | N   | Br     | $CH_2CO_2C(CH_3)_3$|         |
| Cl | $CF_3$ | N   | Br     | $(CH_2)_3CO_2CH_3$ |         |
| Cl | $CF_3$ | N   | Br     | (γ-butyrolactone)  | 118     |
| Cl | Cl     | N   | H      | $CH_2CO_2CH_3$     | 102–104 |
| Cl | Cl     | N   | H      | $CHCO_2CH_3$ \| $CH_3$ | 95–98 |
| Cl | $CF_3$ | CH  | Cl     | $CH_2CO_2C(CH_3)_3$| 120–125 |
| Cl | $CF_3$ | CH  | Cl     | $CH_2CO_2CH_3$     | 85–90   |
| F  | $CF_3$ | CCl | $NO_2$ | $CH_2CO_2CH_3$     |         |
| F  | $CF_3$ | CCl | $NO_2$ | $CH_2CO_2C(CH_3)_3$|         |
| F  | $CF_3$ | CCl | F      | $CH_2CO_2C(CH_3)_3$| 150–152 |
| F  | $CF_3$ | CCl | Br     | $CH_2CO_2CH_3$     | 74–75   |
| F  | $CF_3$ | CCl | Br     | $CHCO_2CH_3$ \| $CH_3$ | 82–88 |
| H  | $CF_3$ | CCl | $NO_2$ | $CH_2CO_2CH_3$     | 166–169 |
| F  | $CF_3$ | CCl | F      | $CH_2CO_2CH_3$     | 90–95   |

EXAMPLE 21

Preparation of m-[(2-Chloro-α,α,α-trifluoro-p-tolyl)oxy]aniline

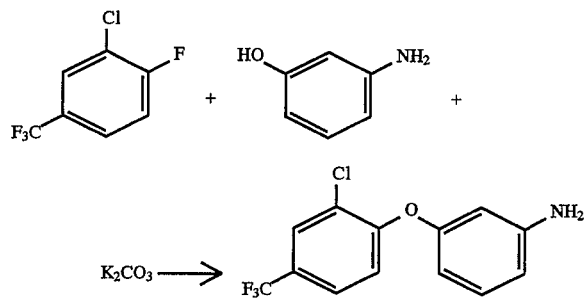

A mixture of 3-aminophenol (10 g, 0.092 mol), 3-chloro-4-fluorobenzotrifluoride (21.83 g, 0.11 mol) and potassium carbonate (15.19 g, 0.11 mol) in dimethyl sulfoxide is stirred at 80° C. for 36 hours and poured into water. The aqueous mixture is extracted with ethyl acetate. The organic extracts are combined, dried over anhydrous magnesium sulfate and concentrated in vacuo to obtain a residue. Column chromatography of the residue using silica gel and an ethyl acetate/hexanes (1:1) solution gives the title product as an amber oil which is identified by $^1$H and $^{13}$CNMR spectral analyses.

Using essentially the same procedure, but substituting 3-amino-4-chlorophenol for 3-aminophenol, 2-chloro-5-[(2-chloro-α,α,α-trifluoro-p-tolyl)oxy]aniline is obtained.

EXAMPLE 22

Preparation of 1-{[(2-Chloro-α,α,α-trifluoro-p-tolyl)oxy]phenyl}-3-methylurea

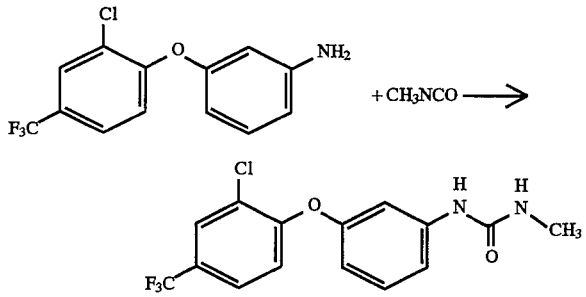

Methyl isocyanate (1.33 g, 0.025 mol) is added to a solution of m-[(2-chloro-α,α,α-trifluoro-p-tolyl)oxy]aniline (5.8 g, 0.02 mol) in toluene. The reaction mixture is stirred at 60° C. for 90 minutes and filtered to obtain the title product as a white solid, mp 165°–169° C.

Using essentially the same procedure, but substituting 2-chloro-5-[(2-chloro-α,α,α-trifluoro-p-tolyl)oxy]aniline for m-[(2-chloro-α,α,α-trifluoro-p-tolyl)oxy]aniline, 1-{2-chloro-5-[(2-chloro-α,α,α-trifluoro-p-tolyl)oxy]phenyl}-3-methylurea is obtained.

EXAMPLE 23

Preparation of 1-{3-[(2-chloro-α,α,α-trifluoro-p-tolyl)oxy]phenyl}-3-methyl-s-triazine-2,4,6(1H,3H,5H)-trione

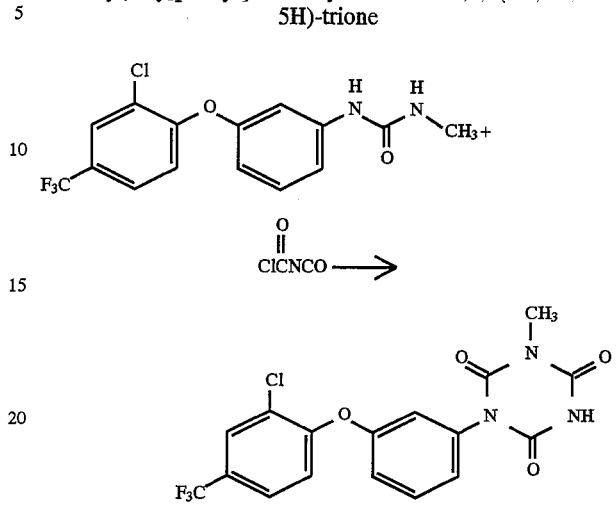

N-(Chlorocarbonyl) isocyante (1.5 g, 0.0143 mol) is added to a mixture of 1-{[(2-chloro-α,α,α-trifluoro-p-tolyl)oxy]phenyl}-3-methylurea (4.1 g, 0.0119 mol) in toluene. The reaction mixture is stirred at 60° C. for 18 hours, cooled to room temperature and concentrated in vacuo to obtain a glass. The glass is dried in a Kugelrohr apparatus to give the title product as a yellow glass which is identified by $^1$H and $^{13}$CNMR spectral analyses.

Using essentially the same procedure, but employing the appropriately substituted 1-phenyl-3-methylurea, the following compounds are obtained:

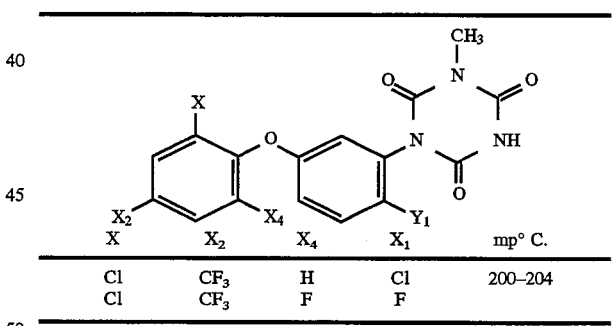

| X | $X_2$ | $X_4$ | $X_1$ | mp° C. |
|---|---|---|---|---|
| Cl | CF$_3$ | H | Cl | 200–204 |
| Cl | CF$_3$ | F | F | |

EXAMPLE 24

Preparation of 3-{2-Bromo-5-{[3-chloro-5-(trifluoromethyl)-2-pyridyl]oxy}phenyl}tetrahydro-5-methyl-2,4,6-trioxo-s-triazine-1(2H)-acetic acid

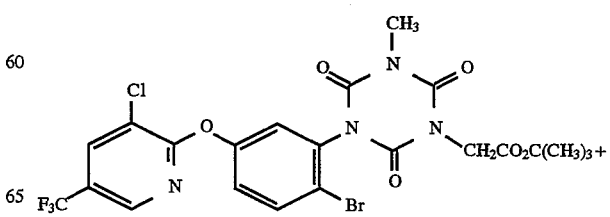

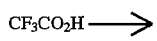

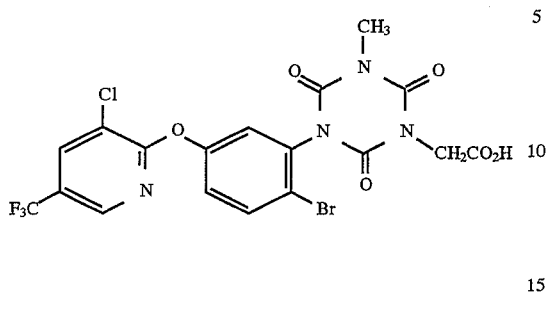

A solution of tert-butyl 3-{2-bromo-5-{[3-chloro-5-(trifluoromethyl)-2-pyridyl]oxy}phenyl}tetrahydro-5-methyl-2,4,6-trioxo-s-triazine-1(2H)-acetate (7.00 g, 0.012 mol) in trifluoroacetic acid (40 mL) is refluxed for 2.5 hours, cooled to room temperature and concentrated in vacuo to give the title product which is identified by $^1$HNMR spectral analysis.

Using essentially the same procedure, but substituting tert-butyl 3-{5-[(2-chloro-α,α,α,6-tetrafluoro-p-tolyl)oxy]-2-nitrophenyl}tetrahydro-5-methyl-2,4,6-trioxo-s-triazine-1(2H)-acetate for tert-butyl 3-{2-bromo-5-{[3-chloro-5-(trifluoromethyl)-2-pyridyl]oxy}phenyl}tetrahydro-5-methyl-2,4,6-trioxo-s-triazine-1(2H)-acetate, 3-{5-[(2-chloro-α,α,α,6-tetrafluoro-p-tolyl)oxy]-2-nitrophenyl}tetrahydro-5-methyl-2,4,6-trioxo-s-triazine-1(2H)-acetic acid is obtained as a yellow glass.

EXAMPLE 25

Preparation of 3-{2-Bromo-5-{[3-chloro-5-(trifluoromethyl)-2-pyridyl]oxy}phenyl}tetrahydro-5-methyl-2,4,6-trioxo-s-triazine-1(2H)-acetyl chloride

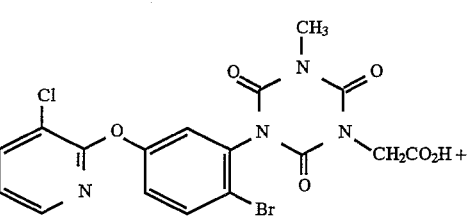

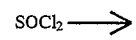

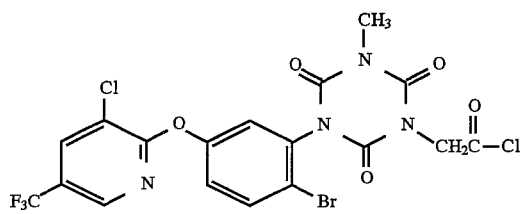

A solution of 3-{2-bromo-5-{[3-chloro-5-(trifluoromethyl)-2-pyridyl]oxy}phenyl}tetrahydro-5-methyl-2,4,6-trioxo-s-triazine-1(2H)-acetic acid (from Example 24) in thionyl chloride is refluxed for 6 hours and concentrated in vacuo to give the title product.

EXAMPLE 26

Preparation of 2-Fluoroethyl 3-{2-bromo-5-{[3-chloro-5-(trifluoromethyl)-2-pyridyl]oxy}phenyl}tetrahydro-5-methyl-2,4,6-trioxo-s-triazine-1(2H)-acetate

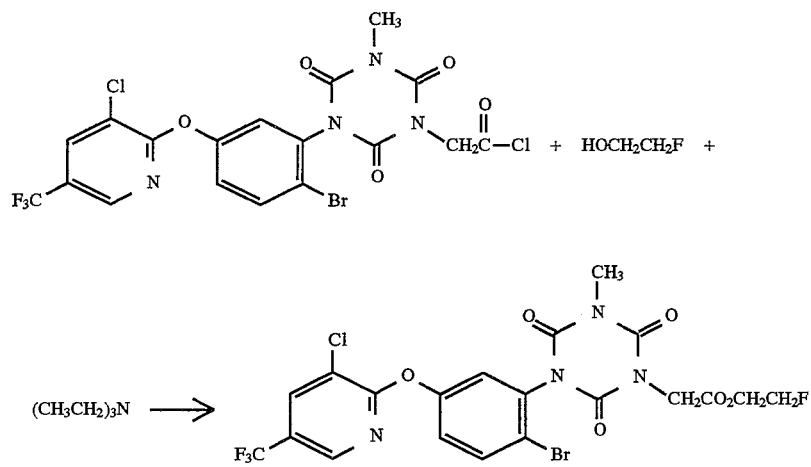

A solution of 3-{2-bromo-5-{[3-chloro-5-(trifluoromethyl)-2-pyridyl]oxy}phenyl}tetrahydro-5-methyl-2,4,6-trioxo-s-triazine-1(2H)-acetyl chloride (0.86 g, 1.6 mmol) in tetrahydrofuran is cooled to 0° C., treated with 2-fluoroethanol (0.206 g, 3.2 mmol) and triethylamine (0.6 mL, 4.3 mmol), stirred at room temperature overnight and diluted with ethyl acetate. The organic mixture is washed sequentially with water, hydrochloric acid, sodium hydrogen carbonate solution and water, dried over anhydrous magnesium sulfate and concentrated in vacuo to obtain a residue. Column chromatography of the residue using silica gel and a 20% ethyl acetate in petroleum ether solution gives the title product as a solid, mp 93°–95° C.

Using essentially the same procedure, but using the appropriate alcohol, the following compounds are obtained:

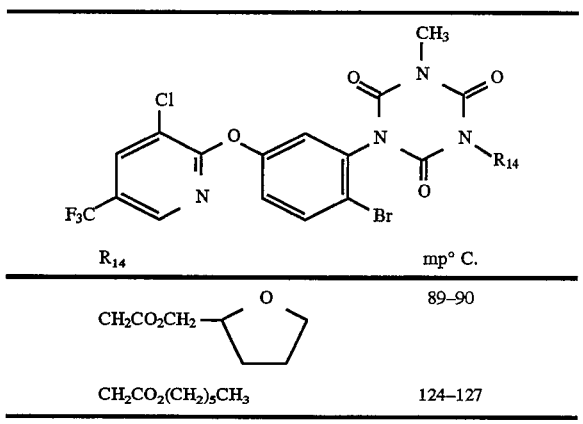

| $R_{14}$ | mp° C. |
|---|---|
| CH$_2$CO$_2$CH$_2$—(tetrahydrofuranyl) | 89–90 |
| CH$_2$CO$_2$(CH$_2$)$_5$CH$_3$ | 124–127 |

EXAMPLE 27

Preparation of N-{{3-{2-Bromo-5-{[3-chloro-5-(trifluoromethyl)-2-pyridyl]oxy}phenyl}-3,4,5,6-tetrahydro-5-methyl-2,4,6-trioxo-s-triazin-1(2H)-yl}acetyl}glycine methyl ester

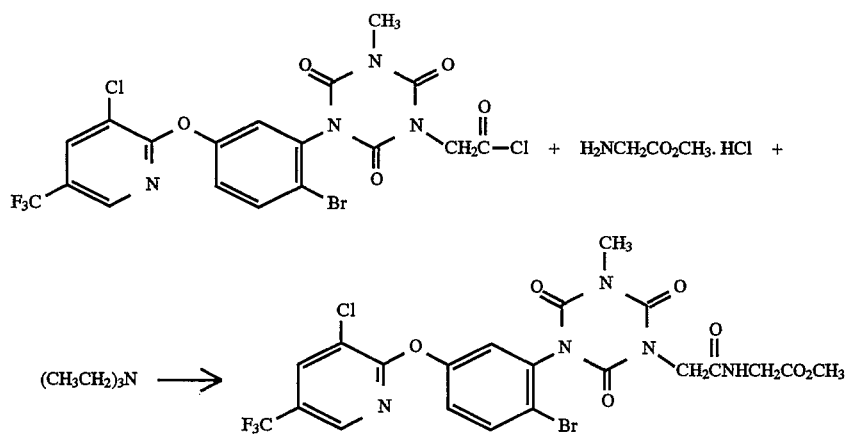

A solution of 3-{2-bromo-5-{[3-chloro-5-(trifluoromethyl)-2-pyridyl]oxy}phenyl}tetrahydro-5-methyl-2,4,6-trioxo-s-triazine-1(2H)-acetyl chloride (0.60 g, 1.1 mmol) in tetrahydrofuran is cooled to 0° C., treated with glycine methyl ester hydrochloride (0.213 g, 1.7 mmol) and triethylamine (0.334 g, 3.3 mmol), stirred at room temperature for 2.5 hours and diluted with ethyl acetate. The organic mixture is washed sequentially with water, hydrochloric acid, water, sodium hydroxide solution, sodium hydrogen carbonate solution and water, dried over anhydrous magnesium sulfate and concentrated in vacuo to obtain a residue. Column chromatography of the residue using silica gel and an ethyl acetate/hexanes (1:5) solution affords a solid which is washed with petroleum ether and dried to give the title product as a white solid which is identified by $^1$H and $^{13}$CNMR spectral analyses.

Using essentially the same procedure, but substituting dimethylamine hydrochloride for glycine methyl ester hydrochloride, 3-{2-bromo-5-{[3-chloro-5-(trifluoromethyl)-2-pyridyl]oxy]phenyl}tetrahydro-N,N,5-trimethyl-2,4,6-trioxo-s-triazine-1(2H)-acetamide is obtained as a white solid.

EXAMPLE 28

Preparation of 2-Bromo-5-hydroxybenzoic acid

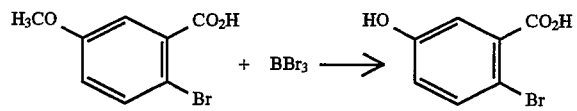

A mixture of 2-bromo-5-methoxybenzoic acid (10 g, 0.043 mol) in methylene chloride is cooled to −60° C., treated with boron tribromide (3.59 g, 0.143 mol), stirred at −60° C. for 1 hour, stirred at room temperature for 1 hour, cooled to −70° C., treated with additional boron tribromide (3.59 g, 0.143 mol), stirred at −70° C. for 1 hour, stirred at room temperature for 1 hour and poured into water. The aqueous mixture is extracted with ethyl acetate. The organic extracts are combined, washed with brine, dried over anhydrous sodium sulfate and concentrated in vacuo to give the title product as a white solid which is identified by $^1$H and $^{13}$CNMR spectral analyses.

EXAMPLE 29

Preparation of 2-Bromo-5-[(2-chloro-α,α,α,6-tetrafluoro-p-tolyl)oxy]benzoic acid

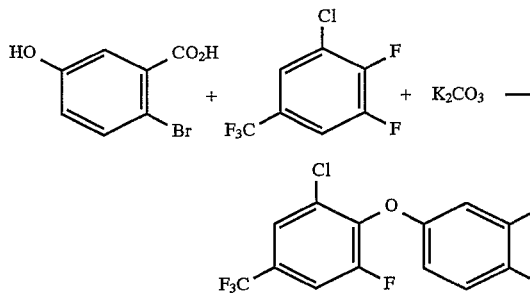

A mixture of 2-bromo-5-hydroxybenzoic acid (6.55 g, 0.030 mol), 5-chloro-α,α,α,3,4-pentafluorotoluene (6.93 g, 0.032 mol) and potassium carbonate (8.29 g, 0.060 mol) in acetonitrile is refluxed for 18 hours, treated with N,N-dimethylformamide (50 mL), refluxed overnight, cooled to room temperature and poured into water. The aqueous mixture is neutralized to pH 7 with 1N hydrochloric acid and extracted with ether. The organic extracts are combined, washed with water, dried over anhydrous sodium sulfate and concentrated in vacuo to obtain an oil. A solution of the oil in ether is washed with water, dried over anhydrous sodium sulfate and concentrated in vacuo to give the title product as a white solid, mp 113°–117° C.

EXAMPLE 30

Preparation of 2-Bromo-5-[(2-chloro-α,α,α,6-tetrafluoro-p-tolyl)oxy]benzoyl chloride

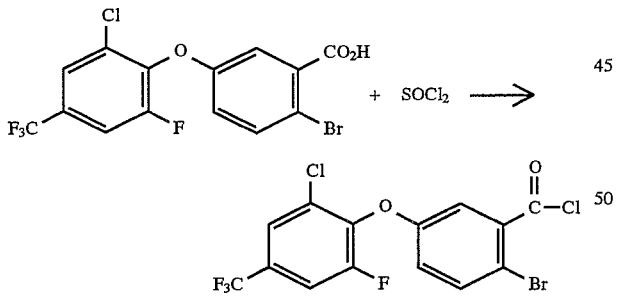

A mixture of 2-bromo-5-[(2-chloro-α,α,α,6-tetrafluoro-p-tolyl)oxy]benzoic acid (15 g, 0.035 mol) in thionyl chloride (75 mL) is heated at 60° C. for 2 hours and concentrated in vacuo to give the title product.

Using essentially the same procedure, but substituting 5-[(2-chloro-α,α,α-trifluoro-p-tolyl)oxy]-2-nitrobenzoic acid for 2-bromo-5-[(2-chloro-α,α,α,6-tetrafluoro-p-tolyl)oxy]benzoic acid, 5-[(2-chloro-α,α,α-trifluoro-p-tolyl)oxy]-2-nitrobenzoyl chloride is obtained.

EXAMPLE 31

Preparation of 2-Bromo-5-[(2-chloro-α,α,α,6-tetrafluoro-p-tolyl)oxy]benzamide

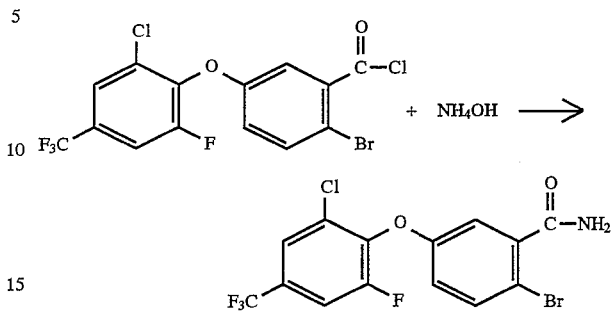

A solution of 2-bromo-5-[(2-chloro-α,α,α,6-tetrafluoro-p-tolyl)oxy]benzoyl chloride (16 g, 0.036 mol) in methylene chloride is cooled to 0° C., treated dropwise with 9.2 mL of a 30% ammonium hydroxide solution (0.071 mol), stirred at 0° C. for 30 minutes, stirred at room temperature overnight and poured into water. The aqueous mixture is extracted with methylene chloride. The organic extracts are combined, washed sequentially with saturated sodium hydrogen carbonate solution and brine, dried over anhydrous magnesium sulfate and concentrated in vacuo to give the title product as a white solid, mp 115°–116° C.

Using essentially the same procedure, but substituting 5-[(2-chloro-α,α,α-trifluoro-p-tolyl)oxy]-2-nitrobenzoyl chloride for 2-bromo-5-[(2-chloro-α,α,α,6-tetrafluoro-p-tolyl)oxy]benzoyl chloride, 5-[(2-chloro-α,α,α-trifluoro-p-tolyl)oxy]-2-nitrobenzamide is obtained.

EXAMPLE 32

Preparation of 1-{2-Bromo-5-[(2-chloro-α,α,α,6-tetrafluoro-p-tolyl)oxy]phenyl}-3-methylurea

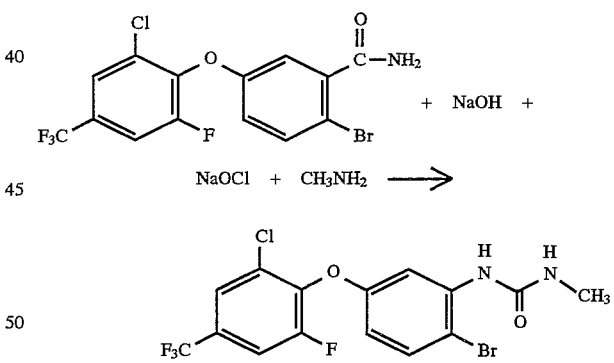

A mixture of 50% sodium hydroxide solution (0.37 g) and sodium hypochlorite solution (3.4 mL, 5% chlorine) is added to a mixture of 2-bromo-5-[(2-chloro-α,α,α,6-tetrafluoro-p-tolyl)oxy]benzamide (2 g, 4.9 mmol) in methanol at 0° C. After the addition, the reaction mixture is treated with water (10 mL), saturated with anhydrous monomethyl amine, stirred at 50° C. for 1 hour, cooled to room temperature and filtered to obtain a solid. The solid is air-dried to give the title product as a white solid which is identified by $^1$H and $^{13}$CNMR spectral analyses.

Using essentially the same procedure, but substituting 5-[(2-chloro-α,α,α-trifluoro-p-tolyl)oxy]-2-nitrobenzamide for 2-bromo-5-[(2-chloro-α,α,α,6-tetrafluoro-p-tolyl)oxy]benzamide, 1-{5-[(2-chloro-α,α,α,-trifluoro-p-tolyl)oxy]-2-nitrophenyl}-3-methylurea is obtained as a yellow solid.

EXAMPLE 33

Preparation of 1-{2-Bromo-5-[(2-chloro-α,α,α,6-tetrafluoro-p-tolyl)oxy]phenyl}-3-methyl-s-triazine-2,4,6(1H,3H,5H)-trione

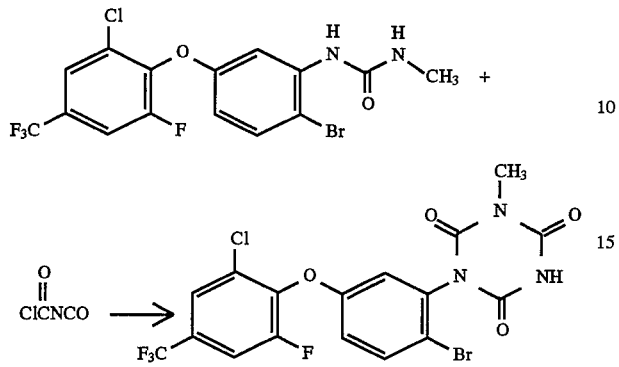

A mixture of 1-{2-bromo-5-[(2-chloro-α,α,α,6-tetrafluoro-p-tolyl)oxy]phenyl}-3-methylurea (4.0 g, 9.1 mmol) in toluene is treated with N-(chlorocarbonyl) isocyanate (1.2 g, 11.4 mmol), stirred at 80° C. for 18 hours, cooled to room temperature and concentrated in vacuo to obtain a solid. A solution of the solid in methylene chloride is washed with brine, dried over anhydrous magnesium sulfate and concentrated in vacuo to give the title product as a white solid, mp 211°-215° C.

Using essentially the same procedure, but substituting 1-{5-[(2-chloro-α,α,α-trifluoro-p-tolyl)oxy]-2-nitrophenyl}-3-methylurea for 1-{2-bromo-5-[(2-chloro-α,α,α,6-tetrafluoro-p-tolyl)oxy]phenyl}-3-methylurea, 1-{5-[(2-chloro-α,α,α-trifluoro-p-tolyl)oxy]-2-nitrophenyl}-3-methyl-s-triazine-2,4,6(1H,3H,5H)-trione is obtained as a white solid.

EXAMPLE 34

Preparation of 5-[(2-chloro-α,α,α-trifluoro-p-tolyl)oxy]-2-nitrophenyl isocyanate

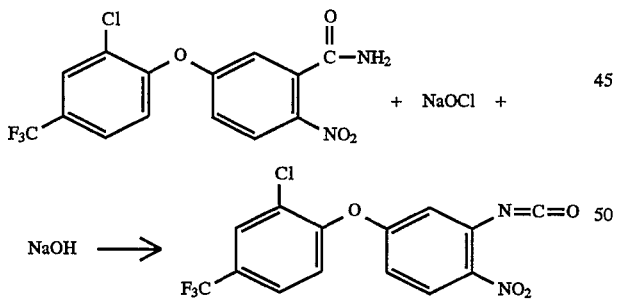

A solution of 5-[(2-chloro-α,α,α-trifluoro-p-tolyl)oxy]-2-nitrobenzamide (108 g, 0.299 mol) in methanol is cooled to 0° C., treated with a solution of 5% sodium hypochlorite solution (487 mL, 0.359 mol) and 50% sodium hydroxide solution (28.7 g, 0.359 mol) in methanol over 20 minutes, and poured into brine. The aqueous mixture is extracted with methylene chloride, adjusted to pH 5 to pH 6 with concentrated hydrochloric acid and extracted with additional methylene chloride. The organic extracts are combined, dried over anhydrous magnesium sulfate and concentrated in vacuo to give the title product as a yellow solid.

Using essentially the same procedure, but substituting 5-[(2-chloro-α,α,α,6-tetrafluoro-p-tolyl)oxy]-2-cyanobenzamide for 5-[(2-chloro-α,α,α-trifluoro-p-tolyl)oxy]-2-nitrobenzamide, 5-[(2-chloro-α,α,α,6-tetrafluoro-p-tolyl)oxy]-2-cyanophenyl isocyanate is obtained

EXAMPLE 35

Preparation of N-{{5-[(2-Chloro-α,α,α-trifluoro-p-tolyl)oxy]-2-ntirophenyl}carbamoyl}glycine ethyl ester

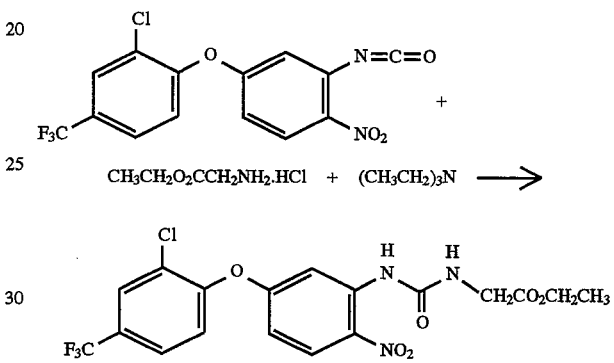

A solution of 5-[(2-chloro-α,α,α-trifluoro-p-tolyl)oxy]-2-nitrophenyl isocyanate (107 g, 0.299 mol) in methylene chloride is cooled to 0° C., treated with a mixture of glycine ethyl ester hydrochloride (50.1 g, 0.359 mol) and triethylamine (166 mL, 1.20 mol) in methylene chloride over 10 minutes, refluxed overnight, cooled to room temperature, washed sequentially with water and brine, dried over anhydrous magnesium sulfate and concentrated in vacuo to obtain a solid. A solution of the solid in methylene chloride is placed on a silica gel plug, eluted with methylene chloride and concentrated in vacuo to give the title product as a yellow solid which is identified by ¹H and ¹³CNMR spectral analyses.

Using essentially the same procedure, but substituting 5-[(2-chloro-α,α,α,6-tetrafluoro-p-tolyl)oxy]-2-cyanophenyl isocyanate for 5-[(2-chloro-α,α,α-trifluoro-p-tolyl)oxy]-2-nitrophenyl isocyanate, N-{{5-[(2-chloro-α,α,α,6-tetrafluoro-p-tolyl)oxy]-2-cyanophenyl}carbamoyl}glycine ethyl ester is obtained.

EXAMPLE 36

Preparation of Ethyl 3-{5-[(2-chloro-α,α,α-trifluoro-p-tolyl)oxy]-2-nitrophenyl}tetrahydro-2,4,6-trioxo-s-triazine-1(2H)-acetate

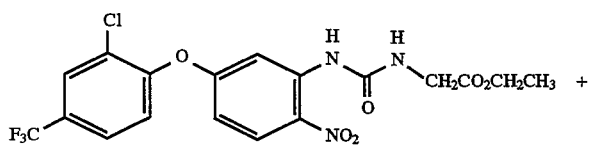

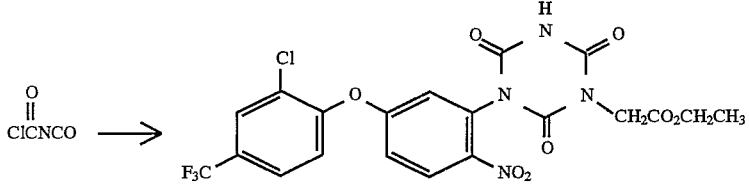

A mixture of N-{{5-[(2-chloro-α,α,α-trifluoro-p-tolyl)oxy]-2-nitrophenyl}carbamoyl}glycine ethyl ester (75.0 g, 0.162 mol) and N-(chlorocarbonyl) isocyanate (35.0 g, 0.332 mol) in toluene is heated at 60° C. overnight, treated with additional N-(chlorocarbonyl) isocyanate (4.25 g), heated at 60° C. for 4 hours, cooled to room temperature and filtered to obtain a solid. The solid is washed with petroleum ether and dried to give the title product as a white solid which is identified by $^1$H and $^{13}$CNMR spectral analyses.

Using essentially the same procedure, but substituting N-{{5-[(2-chloro-α,α,α,6-tetrafluoro-p-tolyl)oxy]-2-cyanophenyl}carbamoyl}glycine ethyl ester for N-{{5-[(2-chloro-α,α,α-trifluoro-p-tolyl)oxy]-2-nitrophenyl}carbamoyl}glycine ethyl ester, ethyl 3-{5-[(2-chloro-α,α,α,6-tetrafluoro-p-tolyl)oxy]-2-cyanophenyl}tetrahydro-2,4,6-trioxo-s-triazine-1(2H)-acetate is obtained as a white solid.

EXAMPLE 37

Preparation of Methyl 3-{5-[(2-chloro-α,α,α-trifluoro-p-tolyl)oxy]-2-nitrophenyl}tetrahydro-2,4,6-trioxo-s-triazine-1(2H)-acetate

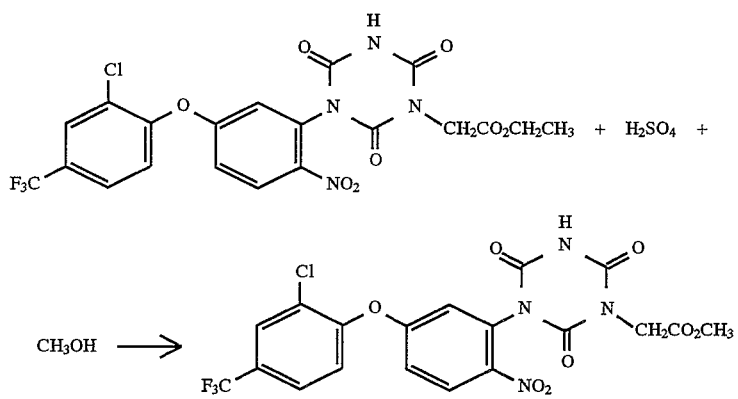

A solution of ethyl 3-{5-[(2-chloro-α,α,α-trifluoro-p-tolyl)oxy]-2-nitrophenyl}tetrahydro-2,4,6-trioxo-s-triazine-1(2H)-acetate (16.0 g, 0.030 mol) and sulfuric acid (1.60 mL, 0.030 mol) in methanol (240 mL, 5.92 mol) is refluxed overnight, treated with sulfuric acid (0.40 mL), refluxed for 90 minutes, treated with sulfuric acid (0.80 mL), refluxed for 90 minutes, treated with sulfuric acid (0.80 mL), refluxed for 1 hour, treated with sulfuric acid (0.80 mL), refluxed for 90 minutes, stirred at room temperature overnight, partially concentrated in vacuo and diluted with ether. The organic mixture is washed sequentially with water and brine, dried over anhydrous magnesium sulfate and concentrated in vacuo to give the title product as a white solid, mp 166°–167° C.

EXAMPLE 38

Preparation of 2-Cyano-5-hydroxybenzamide

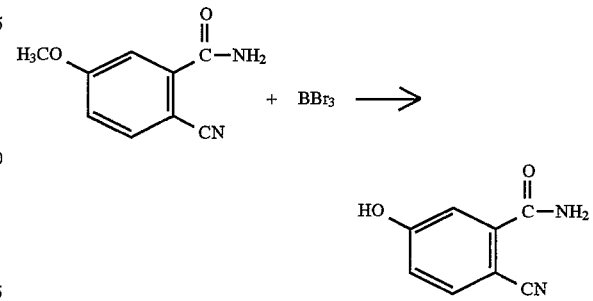

A mixture of 2-cyano-5-methoxybenzamide (5.2 g, 0.027 mol) in methylene chloride is cooled to 0° C., treated dropwise with boron tribromide (54 mL of a 1M solution in methylene chloride), stirred at 0° C. for 30 minutes, stirred at room temperature for 1 hour, refluxed for 4 hours, cooled to 0° C., treated with additional boron tribromide (54 mL of a 1M solution in methylene chloride), refluxed for 17 hours, cooled to room temperature and diluted with water. The aqueous mixture is filtered to obtain a solid which is washed sequentially with water and ether and dried to give the title product as a beige solid, mp 268°–270° C.

EXAMPLE 39

Preparation of 5-[(2-Chloro-α,α,α,6-tetrafluoro-p-tolyl)oxy]-2-cyanobenzamide

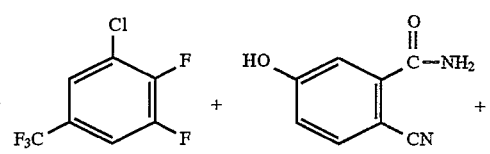

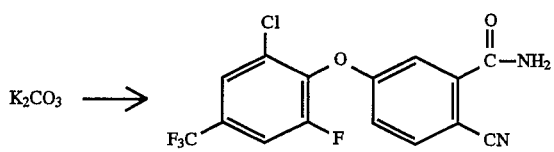

A mixture of 5-chloro-α,α,α,3,4-pentafluorotoluene (2.56 g, 0.0118 mol), 2-cyano-5-hydroxybenzamide (1.60 g, 0.0099 mol) and potassium carbonate (1.64 g, 0.0119 mol) in N,N-dimethylformamide is stirred at 80° C. for 15 hours, cooled to room temperature and poured into an ice-water mixture. The aqueous mixture is filtered to obtain a solid which is washed sequentially with water and hexanes and dried to give the title product as a yellow solid, mp 174°–175° C.

EXAMPLE 40

Postemergence herbicidal evaluation of test compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.125 kg to 0.500 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this postemergence herbicidal evaluation and in the preemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

PLANT SPECIES EMPLOYED IN HERBICIDAL EVALUATIONS

| Header Abb. | Common Name | Scientific Name |
|---|---|---|
| ABUTH | Velvetleaf | ABUTILON THEOPHRASTI, MEDIC. |
| AMBEL | Ragweed, Common | AMBROSIA ARTEMISII-FOLIA, L. |
| CASOB | Sicklepod | CASSIA OBTUSIFOLIA, L. |
| CHEAL | Lambsquarters, Common | CHENOPODIUM ALBUM, L. |
| IPOSS | Morningglory spp. | IPOMOEA SPP. |
| GALAP | Galium | GALIUM APARINE |
| ECHCG | Barnyardgrass | ECHINOCHLOA CRUS-GALLI, (L) BEAU |
| SETVI | Foxtail, Green | SETARIA VIRIDIS, (L) BEAU |
| GLXMAW | Soybean, Williams | GLYCINE MAX(L) MERR. CV. WILLIAMS |
| ORYSAT | Rice, Tebonnet | ORYZA SATIVA, L. TEBONNET |
| TRZAWO | Wheat, Winter, CV. APOLLO | TRITICUM AESTIVUM, CV. APOLLO |
| ZEAMX | Corn, Field | ZEA MAYS L. |

COMPOUNDS EVALUATED AS HERBICIDAL AGENTS

| Compound Number | |
|---|---|
| 1 | Methyl 3-{2-bromo-5-[(2-chloro-α,α,α,6-tetrafluoro-p-tolyl)oxy]phenyl}tetrahydro-α,5-dimethyl-2,4,6-trioxo-s-triazine-1(2H)-acetate |
| 2 | Methyl 3-{2-bromo-5-[(2-chloro-α,α,α,6-tetrafluoro-p-tolyl)oxy]phenyl}tetrahydro-5-methyl-2,4,6-trioxo-s-triazine-1(2H)-acetate |
| 3 | Methyl 3-{5-[(2-chloro-α,α,α-trifluoro-p-tolyl)oxy]-2-nitrophenyl}tetrahydro-5-methyl-2,4,6-trioxo-s-triazine-1(2H)-acetate |
| 4 | Methyl 3-{5-[(2-chloro-α,α,α,6-tetrafluoro-p-tolyl)oxy]-2-fluorophenyl}tetrahydro-5-methyl-2,4,6-trioxo-s-triazine-1(2H)-acetate |
| 5 | Ethyl 3-{5-[(2-chloro-α,α,α-trifluoro-p-tolyl)oxy]-2-nitrophenyl}tetrahydro-2,4,6-trioxo-s-triazine-1(2H)-acetate |
| 6 | 1-Ethyl methyl 5-{5-[(2-chloro-α,α,α-trifluoro-p-tolyl)oxy]-2-nitrophenyl}dihydro-2,4,6-trioxo-s-triazine-1,3(2H,4H)-diacetate |
| 7 | Ethyl 3-{5-[(2-chloro-α,α,α-trifluoro-p-tolyl)oxy]-2-nitrophenyl}tetrahydro-2,4,6-trioxo-5-(2-propynyl)-s-triazine-1(2H)-acetate |
| 8 | Methyl 3-{5-[(2-chloro-α,α,α-trifluoro-p-tolyl)oxy]-2-nitrophenyl}tetrahydro-2,4,6-trioxo-s-triazine-1(2H)-acetate |
| 9 | Ethyl 3-{5-[(2-chloro-α,α,α-trifluoro-p-tolyl)oxy]-2-nitrophenyl}tetrahydro-5-methyl-2,4,6-trioxo-s-triazine-1(2H)-acetate |
| 10 | Ethyl 3-{5-[(2-chloro-α,α,α,6-tetrafluoro-p-tolyl)oxy]-2-cyanophenyl}tetrahydro-2,4,6-trioxo-s-triazine-1(2H)-acetate |
| 11 | Ethyl 3-{5-[(2-chloro-α,α,α,6-tetrafluoro-p-tolyl)oxy]-2-cyanophenyl}tetrahydro-5-methyl-2,4,6-trioxo-s-triazine-1(2H)-acetate |

COMPOUNDS EVALUATED AS HERBICIDAL AGENTS

| Compound Number | |
|---|---|
| 12 | 1-Ethyl methyl 5-{5-[(2-chloro-α,α,α,6-tetrafluoro-p-tolyl)oxy]-2-cyanophenyl}-dihydro-2,4,6-trioxo-s-triazine-1,3(2H,4H)-diacetate |
| 13 | Ethyl 3-allyl-5-{5-[(2-chloro-α,α,α-trifluoro-p-tolyl)oxy]-2-nitrophenyl}tetrahydro-2,4,6-trioxo-s-triazine-1(2H)-acetate |
| 14 | Methyl 3-[5-(2,4-dichlorophenoxy)-2-nitrophenyl]tetrahydro-2,4,6-trioxo-s-triazine-1(2H)-acetate |
| 15 | 3-{5-[(2-Chloro-α,α,α,6-tetrafluoro-p-tolyl)oxy]-2-nitrophenyl}tetrahydro-5-methyl-2,4,6-trioxo-s-triazine-1(2H)-acetic acid |
| 16 | Methyl 3-{5-[(2-chloro-α,α,α,6-tetrafluoro-p-tolyl)oxy]-2-nitrophenyl}tetrahydro-5-methyl-2,4,6-trioxo-s-triazine-1(2H)-acetate |
| 17 | Tert-butyl 3-{5-[(2-chloro-α,α,α,6-tetrafluoro-p-tolyl)oxy]-2-nitrophenyl}tetrahydro-5-methyl-2,4,6-trioxo-s-triazine-1(2H)-acetate |
| 18 | Methyl 3-[5-(2,4-dichlorophenoxy)-2-nitrophenyl]tetrahydro-5-methyl-2,4,6-trioxo-s-trizine-1(2H)-acetate |
| 19 | Dimethyl 5-[5-(2,4-dichlorophenoxy)-2-nitrophenyl]dihydro-2,4,6-trioxo-s-trizine-1,3-(2H,4H)-diacetate |
| 20 | Methyl 3-{5-[(2,4-dichloro-m-tolyl)oxy]-2-nitrophenyl}tetrahydro-5-methyl-2,4,6-trioxo-s-triazine-1(2H)-acetate |
| 21 | Methyl tetrahydro-3-methyl-5-{2-nitro-5-[(α,α,α,4-tetrafluoro-o-tolyl)oxy]phenyl-2,4,6-trioxo-s-triazine-1(2H)-acetate |
| 22 | Methyl 3-[5-(2,3-dichlorophenoxy)-2-nitrophenyl]tetrahydro-5-methyl-2,4,6-trioxo-s-triazine-1(2H)-acetate |
| 23 | Methyl 3-[5-(4-chloro-2-fluorophenoxy)-2-nitrophenyl]tetrahydro-5-methyl-2,4,6-trioxo-s-triazine-1(2H)-acetate |
| 24 | Methyl 3-[5-(2-fluoro-4-nitrophenoxy)-2-nitrophenyl]tetrahydro-5-methyl-2,4,6-trioxo-s-triazine-1(2H)-acetate |
| 25 | Methyl 3-[2-nitro-5-(2,3,5-trichlorophenoxy)phenyl]tetrahydro-5-methyl-2,4,6-trioxo-s-triazine-1(2H)-acetate |
| 26 | Methyl 3-[2-nitro-5-(2,3,4-trichlorophenoxy)phenyl]tetrahydro-5-methyl-2,4,6-trioxo-s-triazine-1(2H)-acetate |
| 27 | Methyl tetrahydro-3-methyl-5-[2-nitro-5-(2,3,4-trifluorophenoxy)phenyl]-2,4,6-trioxo-s-triazine-1(2H)-acetate |
| 28 | Methyl 3-{2-[(2-chloro-α,α,α,-trifluoro-p-tolyl)oxy]phenyl}tetrahydro-5-methyl-2,4,6-trioxo-s-triazine-1(2H)-acetate |
| 29 | Methyl 3-[5-(2,4-dichloro-5-methoxyphenoxy)-2-nitrophenyl]tetrahydro-5-methyl-2,4,6-trioxo-s-triazine-1(2H)-acetate |
| 30 | Methyl tetrahydro-3-methyl-5-[2-nitro-5-(2,4,5-trifluorophenoxy)phenyl]-2,4,6-trioxo-s-triazine-1(2H)-acetate |
| 31 | Methyl tetrahydro-3-methyl-5-[2-nitro-5-(2,4,5-trichlorophenoxy)phenyl]-2,4,6-trioxo-s-triazine-1(2H)-acetate |
| 32 | Methyl 3-[5-(p-cyanophenoxy)-2-nitrophenyl]tetrahydro-5-methyl-2,4,6-trioxo-s-triazine-1(2H)-acetate |
| 33 | Methyl tetrahydro-3-methyl-5-[2-nitro-5-(2,4,6-trichlorophenoxy)phenyl]-2,4,6-trioxo-s-triazine-1(2H)-acetate |
| 34 | Methyl 3-{5-[2-chloro-4-(methylthio)-phenoxy]-2-nitrophenyl}tetrahydro-5-methyl-2,4,6-trioxo-s-triazine-1(2H)-acetate |
| 35 | Methyl 3-[5-(3,5-dichlorophenoxy)-2-nitrophenyl]tetrahydro-5-methyl-2,4,6-trioxo-s-triazine-1(2H)-acetate |
| 36 | Methyl 3-{[2-chloro-4-(methylsulfinyl)-phenoxy]-2-nitrophenyl}tetrahydro-5-methyl-2,4,6-trioxo-s-triazine-1(2H)-acetate |
| 37 | Methyl 3-[5-(2,6-dichlorophenoxy)-2-nitrophenyl]tetrahydro-5-methyl-2,4,6-trioxo-s-triazine-1(2H)-acetate |
| 38 | Methyl tetrahydro-3-methyl-5-[2-nitro-5-(2-pyridyloxy)phenyl]-2,4,6-trioxo-s-triazine-1(2H)-acetate |
| 39 | Methyl 3-{[2-chloro-5-(2-chloro-α,α,α-trifluoro-p-tolyl)oxy]phenyl}tetrahydro-5-methyl-2,4,6-trioxo-s-triazine-1(2H)-acetate |
| 40 | Tert-butyl 3-{[2-chloro-5-(2-chloro-α,α,α-trifluoro-p-tolyl)oxy]phenyl}tetrahydro-5-methyl-2,4,6-trioxo-s-triazine-1(2H)-acetate |
| 41 | Tert-butyl 3-{[5-(2-chloro-α,α,α,6-tetrafluoro-p-tolyl)oxy]-2-fluorophenyl}tetrahydro-5-methyl-2,4,6-trioxo-s-triazine-1(2H)-acetate |
| 42 | 3-{[2-Bromo-5-{[3-chloro-5-(trifluoromethyl)-2-pyridyl]oxy}phenyl}tetrahydro-5-methyl-2,4,6-trioxo-s-triazine-1(2H)-acetamide |
| 43 | Methyl 3-[2-bromo-5-(2,4-dichlorophenoxy)-phenyl]tetrahydro-5-methyl-2,4,6-trioxo-s-triazine-1(2H)-acetate |
| 44 | Isopropyl 3-{[2-bromo-5-{[3-chloro-5-(trifluoromethyl)-2-pyridyl]oxy}phenyl}-tetrahydro-5-methyl-2,4,6-trioxo-s-triazine-1(2H)-acetate |
| 45 | Methyl 3-{[2-bromo-5-{[3-chloro-5-(trifluoromethyl)-2-pyridyl]oxy}phenyl}tetrahydro-5-methyl-2,4,6-trioxo-s-triazine-1(2H)-acetate |
| 46 | 3-{5-[(2-Chloro-α,α,α-trifluoro-p-tolyl)-oxy]phenyl}tetrahydro-5-methyl-2,4,6-trioxo-s-triazine-1(2H)-acetamide |

TABLE I

Postemergence Herbicidal Evaluations Of Test Compounds

| Compound Number | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| 1 | 0.500 | 9.0 | 6.0 | — | 9.0 | 9.0 | — | 2.0 | 4.0 | 5.0 | — | — | 3.0 |
|  | 0.250 | 9.0 | 5.0 | — | 9.0 | 9.0 | — | 2.0 | 2.0 | 6.0 | — | — | 2.0 |
|  | 0.125 | 9.0 | 3.0 | — | 9.0 | 8.0 | — | 1.0 | 0.0 | 4.0 | — | — | 1.0 |
| 2 | 0.500 | 9.0 | 8.0 | 9.0 | 8.5 | 9.0 | 9.0 | 9.0 | 9.0 | 8.3 | 7.5 | 8.5 | 8.3 |
|  | 0.250 | 9.0 | 7.5 | 9.0 | 8.5 | 9.0 | 9.0 | 9.0 | 9.0 | 8.0 | 7.0 | 8.0 | 8.3 |
|  | 0.125 | 9.0 | 7.3 | 9.0 | 8.7 | 8.7 | 9.0 | 6.7 | 9.0 | 7.2 | 6.3 | 7.5 | 8.4 |
| 3 | 0.500 | 8.6 | 9.0 | 8.8 | 8.2 | 8.8 | 9.0 | 8.8 | 8.6 | 7.3 | 7.1 | 8.1 | 7.5 |
|  | 0.250 | 9.0 | 9.0 | 8.5 | 7.5 | 9.0 | 8.7 | 8.6 | 8.5 | 6.5 | 6.7 | 7.8 | 7.2 |
|  | 0.125 | 9.0 | 8.8 | 9.0 | 7.4 | 8.8 | 8.8 | 7.3 | 7.6 | 6.2 | 5.8 | 7.4 | 6.1 |
| 4 | 0.500 | 9.0 | 8.8 | 8.8 | 9.0 | 9.0 | 9.0 | 9.0 | 9.0 | 7.8 | 7.0 | 8.6 | 8.8 |
|  | 0.250 | 9.0 | 8.8 | 9.0 | 9.0 | 9.0 | 8.8 | 8.9 | 9.0 | 7.1 | 6.3 | 8.2 | 8.8 |
|  | 0.125 | 9.0 | 8.3 | 9.0 | 8.8 | 9.0 | 8.7 | 8.0 | 9.0 | 6.2 | 5.6 | 8.0 | 8.8 |
| 5 | 0.500 | 9.0 | 9.0 | 8.5 | 8.0 | 9.0 | 9.0 | 6.0 | 6.5 | 5.8 | 4.8 | 6.0 | 6.0 |
|  | 0.250 | 9.0 | 9.0 | 8.0 | 8.0 | 9.0 | 9.0 | 5.5 | 4.0 | 5.5 | 4.8 | 5.5 | 4.5 |
|  | 0.125 | 9.0 | 8.5 | 6.5 | 8.0 | 9.0 | 7.5 | 4.0 | 4.5 | 4.8 | 4.0 | 5.0 | 4.5 |
| 6 | 0.500 | 9.0 | 9.0 | 6.5 | 4.5 | 8.0 | 8.0 | 4.5 | 2.0 | 4.5 | 4.3 | 5.3 | 4.5 |
|  | 0.250 | 9.0 | 8.5 | 8.0 | 3.0 | 8.0 | 7.0 | 4.5 | 2.0 | 4.8 | 4.3 | 5.0 | 4.5 |
|  | 0.125 | 9.0 | 8.0 | 7.0 | 1.5 | 7.0 | 6.0 | 3.5 | 0.5 | 4.0 | 3.8 | 4.3 | 4.0 |
| 7 | 0.500 | 7.0 | 7.0 | 7.0 | 4.0 | 9.0 | 4.0 | 6.0 | 3.0 | 4.5 | 5.5 | 5.5 | 5.0 |
|  | 0.250 | 9.0 | 8.0 | 7.0 | 3.0 | 8.0 | 6.0 | 6.0 | 0.0 | 4.0 | 5.0 | 5.0 | 4.5 |
|  | 0.125 | 7.0 | 6.0 | 6.0 | 3.0 | 9.0 | 3.0 | 8.0 | 0.0 | 4.5 | 5.0 | 4.5 | 4.5 |
| 8 | 0.500 | 9.0 | 9.0 | 9.0 | 9.0 | 9.0 | 9.0 | 7.0 | 6.0 | 5.5 | 6.0 | 6.0 | 6.5 |
|  | 0.250 | 9.0 | 9.0 | 9.0 | 9.0 | 9.0 | 9.0 | 3.0 | 3.0 | 5.0 | 5.5 | 5.5 | 6.0 |
|  | 0.125 | 9.0 | 9.0 | 7.0 | 9.0 | 9.0 | 8.0 | 0.0 | 0.0 | 5.0 | 5.0 | 4.5 | 5.0 |
| 9 | 0.500 | 9.0 | 9.0 | 9.0 | 9.0 | 9.0 | 9.0 | 6.0 | 9.0 | 5.5 | 6.5 | 8.5 | 6.5 |
|  | 0.250 | 9.0 | 9.0 | 9.0 | 9.0 | 9.0 | 8.0 | 5.0 | 7.0 | 4.5 | 4.5 | 7.5 | 5.0 |
|  | 0.125 | 9.0 | 9.0 | 9.0 | 9.0 | 9.0 | 8.0 | 4.0 | 8.0 | 4.5 | 4.5 | 7.5 | 4.5 |
| 10 | 0.500 | 9.0 | 9.0 | 7.0 | 9.0 | 9.0 | 7.0 | 3.0 | 3.0 | 6.5 | 4.5 | 5.5 | 4.5 |
|  | 0.250 | 9.0 | 8.0 | 8.0 | 9.0 | 8.0 | 7.0 | 2.0 | 0.0 | 5.0 | 4.0 | 3.0 | 3.5 |
|  | 0.125 | 9.0 | 9.0 | 5.0 | 9.0 | 9.0 | 5.0 | 2.0 | 2.0 | 4.5 | 3.5 | 3.0 | 3.5 |
| 11 | 0.500 | 9.0 | 9.0 | 9.0 | 9.0 | 9.0 | 8.0 | 8.0 | 9.0 | 6.0 | 5.0 | 7.0 | 9.0 |
|  | 0.250 | 9.0 | 9.0 | 9.0 | 9.0 | 9.0 | 8.0 | 7.0 | 9.0 | 5.0 | 5.0 | 7.5 | 9.0 |
|  | 0.125 | 9.0 | 9.0 | 9.0 | 9.0 | 9.0 | 5.0 | 3.0 | 9.0 | 4.5 | 4.5 | 6.0 | 8.0 |
| 12 | 0.500 | 9.0 | 8.0 | 9.0 | 9.0 | 9.0 | 7.0 | 3.0 | 7.0 | 4.0 | 5.0 | 5.0 | 4.5 |
|  | 0.250 | 7.0 | 6.0 | 8.0 | 9.0 | 6.0 | 7.0 | 3.0 | 2.0 | 5.5 | 4.0 | 4.5 | 4.5 |
|  | 0.125 | 8.0 | 6.0 | 7.0 | 9.0 | 9.0 | 5.0 | 4.0 | 0.0 | 4.0 | 3.5 | 4.5 | 4.0 |
| 13 | 0.500 | 9.0 | 9.0 | 7.0 | 9.0 | 6.0 | 9.0 | 3.0 | 2.0 | 5.5 | 3.5 | 5.5 | 5.0 |
|  | 0.250 | 9.0 | 9.0 | 9.0 | 7.0 | 6.0 | 8.0 | 3.0 | 0.0 | 5.5 | 4.0 | 5.0 | 4.0 |
|  | 0.125 | 8.0 | 8.0 | 6.0 | 5.0 | 5.0 | 6.0 | 0.0 | 0.0 | 4.5 | 3.0 | 4.5 | 4.0 |
| 14 | 0.500 | 9.0 | 9.0 | 9.0 | 9.0 | 8.0 | 7.0 | 4.0 | 4.0 | 5.5 | 5.5 | 6.5 | 6.0 |
|  | 0.250 | 9.0 | 9.0 | 9.0 | 9.0 | 7.0 | 5.0 | 3.0 | 3.0 | 5.5 | 6.0 | 5.5 | 5.5 |
|  | 0.125 | 8.0 | 8.0 | 8.0 | 8.0 | 7.0 | 4.0 | 3.0 | 3.0 | 5.0 | 5.5 | 5.5 | 5.0 |
| 15 | 0.500 | 9.0 | 9.0 | 9.0 | 5.0 | 9.0 | 9.0 | 8.0 | 4.0 | 5.7 | 8.5 | 9.0 | 7.0 |
|  | 0.250 | 9.0 | 9.0 | 9.0 | 4.0 | 9.0 | 8.5 | 9.0 | 2.5 | 5.7 | 8.5 | 9.0 | 6.7 |
|  | 0.125 | 9.0 | 9.0 | 9.0 | 0.0 | 8.0 | 8.0 | 6.0 | 1.0 | 4.7 | 6.0 | 8.3 | 4.3 |
| 16 | 0.500 | 9.0 | 9.0 | 9.0 | 9.0 | 9.0 | 9.0 | 8.7 | 3.7 | 6.2 | 7.8 | 8.4 | 6.4 |
|  | 0.250 | 9.0 | 9.0 | 9.0 | 7.5 | 9.0 | 9.0 | 7.0 | 3.0 | 6.4 | 7.3 | 8.4 | 5.0 |
|  | 0.125 | 9.0 | 9.0 | 9.0 | 6.5 | 9.0 | 9.0 | 3.7 | 1.3 | 5.6 | 5.8 | 8.4 | 4.2 |
| 17 | 0.500 | 9.0 | 9.0 | 8.0 | 5.0 | 8.0 | 9.0 | 2.5 | 2.0 | 4.0 | 3.0 | 3.7 | 3.3 |
|  | 0.250 | 9.0 | 9.0 | 9.0 | 4.0 | 9.0 | 8.0 | 2.0 | 1.0 | 3.3 | 4.0 | 3.7 | 3.0 |
|  | 0.125 | 9.0 | 8.5 | 6.5 | 2.0 | 9.0 | 7.5 | 0.5 | 0.5 | 3.3 | 3.5 | 3.0 | 2.7 |
| 18 | 0.500 | 9.0 | 8.0 | 9.0 | 9.0 | 9.0 | 9.0 | 9.0 | 9.0 | 5.0 | 5.0 | 7.5 | 8.0 |
|  | 0.250 | 9.0 | 7.0 | 9.0 | 9.0 | 9.0 | 9.0 | 8.0 | 9.0 | 5.0 | 5.0 | 8.0 | 8.0 |
|  | 0.125 | 9.0 | 8.0 | 9.0 | 9.0 | 9.0 | 9.0 | 6.0 | 8.0 | 5.5 | 3.5 | 7.5 | 7.0 |
| 19 | 0.500 | 9.0 | 9.0 | 9.0 | 9.0 | 8.0 | 9.0 | 4.0 | 5.0 | 5.5 | 4.0 | 5.5 | 4.0 |
|  | 0.250 | 9.0 | 9.0 | 9.0 | 9.0 | 9.0 | 9.0 | 3.0 | 5.0 | 4.5 | 5.0 | 5.0 | 3.5 |
|  | 0.125 | 9.0 | 6.0 | 9.0 | 7.0 | 8.0 | 9.0 | 3.0 | 3.0 | 4.0 | 4.0 | 4.5 | 3.5 |
| 20 | 0.500 | 9.0 | 7.0 | 9.0 | 7.0 | 9.0 | 6.0 | 3.0 | 5.0 | 5.5 | 4.5 | 5.0 | 5.5 |
|  | 0.250 | 9.0 | 8.0 | 8.0 | 9.0 | 9.0 | 3.0 | 2.0 | 3.0 | 5.5 | 3.5 | 5.0 | 5.0 |
|  | 0.125 | 9.0 | 5.0 | 8.0 | 8.0 | 9.0 | 6.0 | 0.0 | 2.0 | 4.5 | 4.0 | 4.0 | 4.5 |
| 21 | 0.500 | 9.0 | 4.0 | 4.0 | 9.0 | 6.0 | 4.5 | 9.0 | 9.0 | 4.0 | 4.5 | 8.0 | 8.5 |
|  | 0.250 | 9.0 | 3.0 | 5.0 | 5.0 | 9.0 | 6.0 | 8.0 | 9.0 | 4.0 | 4.5 | 7.5 | 8.0 |
|  | 0.125 | 7.0 | 2.0 | 4.0 | 4.0 | 8.0 | 3.0 | 6.0 | 7.0 | 4.0 | 3.5 | 7.0 | 7.5 |
| 22 | 0.500 | 8.0 | 3.0 | 3.5 | 5.0 | 4.0 | 3.0 | 5.0 | 4.0 | 4.0 | 3.5 | 5.0 | 3.5 |
|  | 0.250 | 8.0 | 3.0 | 6.0 | 4.0 | 7.0 | 6.0 | 2.0 | 2.0 | 4.0 | 4.0 | 5.0 | 3.5 |
|  | 0.125 | 7.0 | 0.0 | 3.0 | 2.0 | 4.0 | 6.0 | 0.0 | 0.0 | 3.0 | 3.5 | 4.0 | 3.0 |
| 23 | 0.500 | 9.0 | 8.0 | 4.0 | 8.0 | 9.0 | 4.5 | 9.0 | 8.0 | 6.0 | 5.0 | 8.5 | 6.0 |
|  | 0.250 | 9.0 | 6.0 | 9.0 | 6.0 | 9.0 | 6.0 | 6.0 | 5.0 | 4.5 | 4.5 | 7.5 | 5.5 |
|  | 0.125 | 8.0 | 5.0 | 6.0 | 6.0 | 8.0 | 9.0 | 5.0 | 3.0 | 4.5 | 4.0 | 7.5 | 4.5 |
| 24 | 0.500 | 3.0 | 4.0 | 1.5 | 2.0 | 4.0 | 2.0 | 0.0 | 0.0 | 1.5 | 1.5 | 2.0 | 2.0 |
|  | 0.250 | 2.0 | 4.0 | 2.0 | 0.0 | 4.0 | 2.0 | 0.0 | 0.0 | 1.5 | 1.5 | 2.0 | 1.5 |
|  | 0.125 | 0.0 | 1.0 | 0.0 | 0.0 | 2.0 | 2.0 | 0.0 | 0.0 | 0.5 | 1.0 | 1.0 | 1.5 |
| 25 | 0.500 | 0.0 | 0.0 | 0.0 | 0.0 | 0.0 | 0.0 | 0.0 | 0.0 | 0.0 | 1.0 | 0.5 | 1.0 |

TABLE I-continued

Postemergence Herbicidal Evaluations Of Test Compounds

| Compound Number | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
|    | 0.250 | 0.0 | 0.0 | 0.0 | 0.0 | 0.0 | 0.0 | 0.0 | 0.0 | 0.0 | 0.5 | 0.5 | 1.0 |
|    | 0.125 | 0.0 | 0.0 | 0.0 | 0.0 | 0.0 | 0.0 | 0.0 | 0.0 | 0.0 | 0.0 | 0.0 | 0.0 |
| 26 | 0.500 | 9.0 | 7.0 | 9.0 | 9.0 | 9.0 | 7.0 | 4.0 | 3.0 | 5.0 | 5.0 | 5.0 | 5.5 |
|    | 0.250 | 8.0 | 7.0 | 3.5 | 8.0 | 7.0 | 4.0 | 2.0 | 0.0 | 5.0 | 4.5 | 5.0 | 4.0 |
|    | 0.125 | 6.0 | 6.0 | 7.0 | 6.0 | 8.0 | 5.0 | 0.0 | 0.0 | 4.0 | 3.5 | 4.0 | 3.5 |
| 27 | 0.500 | 9.0 | 5.0 | 3.0 | 6.0 | 7.0 | 4.5 | 9.0 | 4.0 | 3.5 | 4.5 | 5.5 | 4.5 |
|    | 0.250 | 8.0 | 5.0 | 5.0 | 5.0 | 6.0 | 6.0 | 5.0 | 2.0 | 3.0 | 4.0 | 5.0 | 4.0 |
|    | 0.125 | 7.0 | 2.0 | 2.0 | 3.0 | 4.0 | 6.0 | 2.0 | 0.0 | 2.5 | 3.5 | 3.5 | 3.5 |
| 28 | 0.500 | 9.0 | 7.0 | 6.5 | 9.0 | 9.0 | 4.5 | 2.0 | 4.0 | 5.0 | 3.0 | 2.0 | 4.5 |
|    | 0.250 | 7.0 | 6.0 | 6.0 | 8.0 | 8.0 | 5.0 | 0.0 | 2.0 | 4.5 | 2.5 | 2.0 | 4.0 |
|    | 0.125 | 6.0 | 4.0 | 5.0 | 6.0 | 6.0 | 4.0 | 0.0 | 1.0 | 3.5 | 2.0 | 2.0 | 2.5 |
| 29 | 0.500 | 7.0 | 8.0 | 5.5 | 9.0 | 6.0 | 2.0 | 1.0 | 2.0 | 4.5 | 2.5 | 3.0 | 4.5 |
|    | 0.250 | 7.0 | 7.0 | 8.0 | 7.0 | 5.0 | 3.0 | 0.0 | 1.0 | 4.5 | 2.0 | 3.0 | 3.5 |
|    | 0.125 | 5.0 | 6.0 | 7.0 | 6.0 | 5.0 | 0.0 | 0.0 | 0.0 | 3.5 | 1.5 | 2.0 | 3.5 |
| 30 | 0.500 | 5.0 | 6.0 | 4.5 | 5.0 | 5.0 | 5.0 | 1.0 | 1.0 | 4.0 | 3.0 | 4.5 | 4.5 |
|    | 0.250 | 5.0 | 5.0 | 4.0 | 5.0 | 4.0 | 6.0 | 1.0 | 2.0 | 4.0 | 3.0 | 4.0 | 3.0 |
|    | 0.125 | 3.0 | 4.0 | 5.0 | 4.0 | 4.0 | 3.0 | 0.0 | 0.0 | 4.5 | 3.0 | 3.5 | 3.0 |
| 31 | 0.500 | 7.0 | 8.0 | 5.5 | 7.0 | 6.0 | 2.5 | 0.0 | 0.0 | 4.5 | 4.0 | 5.5 | 4.0 |
|    | 0.250 | 7.0 | 7.0 | 8.0 | 7.0 | 6.0 | 4.0 | 2.0 | 2.0 | 4.0 | 4.0 | 5.0 | 4.0 |
|    | 0.125 | 5.0 | 7.0 | 9.0 | 7.0 | 5.0 | 4.0 | 0.0 | 1.0 | 3.5 | 3.0 | 3.5 | 3.5 |
| 32 | 0.500 | 0.0 | 0.0 | 0.0 | 2.0 | 0.0 | 0.0 | 0.0 | 0.0 | 3.0 | 1.5 | 1.5 | 2.0 |
|    | 0.250 | 0.0 | 0.0 | 0.0 | 0.0 | 0.0 | 0.0 | 0.0 | 0.0 | 2.5 | 1.0 | 1.5 | 1.5 |
|    | 0.125 | 0.0 | 0.0 | 0.0 | 0.0 | 0.0 | 0.0 | 0.0 | 0.0 | 2.0 | 1.0 | 1.0 | 1.5 |
| 33 | 0.500 | 9.0 | 9.0 | 9.0 | 9.0 | 9.0 | 9.0 | 4.0 | 5.0 | 6.0 | 6.5 | 7.0 | 5.0 |
|    | 0.250 | 9.0 | 8.0 | 9.0 | 9.0 | 8.0 | 9.0 | 3.0 | 4.0 | 5.5 | 5.5 | 6.5 | 5.0 |
|    | 0.125 | 8.0 | 8.0 | 7.5 | 8.0 | 7.0 | 5.5 | 2.0 | 2.0 | 4.5 | 5.5 | 6.0 | 4.5 |
| 34 | 0.500 | 5.0 | 2.0 | 3.0 | 4.0 | 4.0 | 3.0 | 0.0 | 0.0 | 3.5 | 2.5 | 2.0 | 4.0 |
|    | 0.250 | 3.0 | 2.0 | 2.0 | 2.0 | 5.0 | 0.0 | 0.0 | 0.0 | 2.5 | 2.0 | 2.0 | 3.5 |
|    | 0.125 | 2.0 | 2.0 | 0.0 | 3.0 | 3.0 | 0.0 | 0.0 | 0.0 | 2.0 | 1.5 | 2.0 | 3.5 |
| 35 | 0.500 | 0.0 | 0.0 | 0.0 | 0.0 | 2.0 | 0.0 | 0.0 | 0.0 | 0.5 | 0.5 | 0.0 | 1.0 |
|    | 0.250 | 0.0 | 0.0 | 0.0 | 0.0 | 1.0 | 0.0 | 0.0 | 0.0 | 1.0 | 0.5 | 0.0 | 1.0 |
|    | 0.125 | 0.0 | 0.0 | 0.0 | 0.0 | 1.0 | 0.0 | 0.0 | 0.0 | 0.5 | 0.0 | 0.0 | 1.0 |
| 36 | 0.500 | 8.0 | 8.0 | 5.0 | 8.0 | 8.0 | 4.0 | 4.0 | 3.0 | 5.0 | 3.5 | 3.0 | 4.0 |
|    | 0.250 | 7.0 | 7.0 | 5.0 | 8.0 | 6.0 | 8.0 | 2.0 | 2.0 | 5.0 | 3.0 | 3.0 | 3.5 |
|    | 0.125 | 7.0 | 6.0 | 6.0 | 8.0 | 9.0 | 6.0 | 0.0 | 0.0 | 5.0 | 3.0 | 2.5 | 4.0 |
| 37 | 0.500 | 8.0 | 6.0 | 2.5 | 6.0 | 5.0 | 3.0 | 4.0 | 3.0 | 5.0 | 3.5 | 5.5 | 4.0 |
|    | 0.250 | 6.0 | 4.0 | 5.0 | 5.0 | 3.0 | 5.0 | 2.0 | 2.0 | 4.5 | 2.0 | 4.0 | 2.0 |
|    | 0.125 | 5.0 | 4.0 | 2.0 | 3.0 | 6.0 | 6.0 | 2.0 | 0.0 | 3.5 | 1.5 | 3.5 | 1.5 |
| 38 | 0.500 | 0.0 | 0.0 | 0.0 | 0.0 | 0.0 | 0.0 | 0.0 | 0.0 | 0.5 | 0.0 | 0.0 | 0.0 |
| 39 | 0.500 | 9.0 | 9.0 | 9.0 | 9.0 | 9.0 | 9.0 | 8.0 | 9.0 | 7.0 | 4.5 | 5.5 | 8.5 |
|    | 0.250 | 9.0 | 9.0 | 9.0 | 9.0 | 9.0 | 9.0 | 7.5 | 8.0 | 6.3 | 4.8 | 6.0 | 8.0 |
|    | 0.125 | 9.0 | 8.5 | 9.0 | 9.0 | 9.0 | 8.0 | 4.5 | 4.5 | 5.5 | 4.3 | 4.8 | 6.5 |
| 40 | 0.500 | 9.0 | 7.5 | 9.0 | 9.0 | 9.0 | 7.0 | 1.0 | 3.5 | 5.3 | 4.8 | 4.5 | 4.8 |
|    | 0.250 | 6.5 | 7.0 | 7.5 | 7.0 | 7.5 | 7.0 | 2.5 | 2.0 | 4.0 | 3.3 | 2.3 | 4.0 |
|    | 0.125 | 7.0 | 4.5 | 5.5 | 5.0 | 7.5 | 5.5 | 0.0 | 1.0 | 3.8 | 1.8 | 2.3 | 3.3 |
| 41 | 0.500 | 6.0 | 4.0 | 3.0 | 4.0 | 5.0 | 4.0 | 3.0 | 4.0 | 4.0 | 3.0 | 3.5 | 3.5 |
|    | 0.250 | 6.5 | 6.0 | 5.5 | 6.0 | 6.0 | 3.0 | 2.5 | 3.0 | 4.0 | 3.5 | 3.3 | 4.8 |
|    | 0.125 | 6.0 | 4.0 | 3.0 | 5.0 | 5.0 | 2.5 | 0.0 | 0.0 | 3.5 | 2.5 | 2.3 | 3.3 |
| 42 | 0.500 | 7.0 | 4.5 | 3.7 | 6.5 | 6.5 | 2.0 | 1.5 | 1.0 | 4.3 | 3.0 | 2.0 | 3.0 |
|    | 0.250 | 4.0 | 3.0 | 4.0 | 6.5 | 4.0 | 3.0 | 1.0 | 1.0 | 4.3 | 2.3 | 1.3 | 2.8 |
|    | 0.125 | 2.0 | 2.0 | 2.5 | 3.5 | 3.0 | 2.0 | 0.5 | 1.0 | 3.5 | 1.8 | 1.3 | 2.3 |
| 43 | 0.500 | 9.0 | 6.5 | 9.0 | 9.0 | 7.0 | 5.0 | 7.5 | 8.0 | 6.0 | 5.0 | 7.0 | 8.3 |
|    | 0.250 | 8.5 | 6.5 | 8.0 | 8.5 | 9.0 | 4.0 | 4.5 | 4.5 | 5.0 | 4.8 | 5.3 | 6.5 |
|    | 0.125 | 5.5 | 5.5 | 7.5 | 8.5 | 6.5 | 3.5 | 3.0 | 2.5 | 4.5 | 4.0 | 4.8 | 4.8 |
| 44 | 0.500 | 9.0 | 9.0 | 9.0 | 9.0 | 9.0 | 5.0 | 9.0 | 9.0 | 5.5 | 6.0 | 9.0 | 9.0 |
|    | 0.250 | 9.0 | 9.0 | 9.0 | 9.0 | 9.0 | 2.0 | 9.0 | 9.0 | 5.5 | 5.5 | 9.0 | 9.0 |
|    | 0.125 | 2.0 | 5.0 | 9.0 | 9.0 | 9.0 | 0.0 | 3.0 | 9.0 | 5.0 | 4.5 | 7.5 | 6.5 |
| 45 | 0.500 | 9.0 | 9.0 | 9.0 | 9.0 | 9.0 | 9.0 | 9.0 | 9.0 | 7.5 | 6.5 | 9.0 | 9.0 |
|    | 0.250 | 9.0 | 9.0 | 9.0 | 9.0 | 9.0 | 3.0 | 9.0 | 9.0 | 7.5 | 5.5 | 9.0 | 9.0 |
|    | 0.125 | 9.0 | 9.0 | 9.0 | 9.0 | 9.0 | 7.0 | 7.0 | 9.0 | 7.0 | 5.0 | 9.0 | 9.0 |
| 46 | 0.500 | 3.0 | 0.0 | 0.0 | 2.0 | 4.0 | 1.0 | 0.0 | 0.0 | 4.5 | 2.5 | 1.0 | 1.0 |
|    | 0.250 | 2.0 | 0.0 | 0.0 | 7.0 | 3.0 | 3.0 | 0.0 | 0.0 | 3.5 | 2.5 | 1.0 | 1.0 |
|    | 0.125 | 0.0 | 0.0 | 0.0 | 4.0 | 3.0 | 0.0 | 0.0 | 0.0 | 2.0 | 1.5 | 0.5 | 0.5 |

EXAMPLE 41

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.125 to 0.50 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 40.

The data obtained are reported in Table II below. The compounds evaluated are reported by compound number given in Example 40.

TABLE II

| | | Preemergence Herbicidal Evaluations Of Test Compounds | | | | | | | | | | |
|---|---|---|---|---|---|---|---|---|---|---|---|---|
| Compound Number | Rate (kg/ha) | ABUTH | AMBEL | CASOB | CHEAL | IPOSS | GALAP | ECHCG | SETVI | GLXMAW | ORYSAT | TRZAWO | ZEAMX |
| 1 | 0.500 | 9.0 | 0.0 | — | 9.0 | 6.0 | — | 3.0 | 9.0 | 3.0 | — | 1.0 | 4.0 |
| | 0.250 | 6.0 | 0.0 | — | 9.0 | 4.0 | — | 2.0 | 5.0 | 2.0 | — | 1.0 | 4.0 |
| | 0.125 | 0.0 | 0.0 | — | 9.0 | 0.0 | — | 2.0 | 2.0 | 2.0 | — | 0.0 | 0.0 |
| 2 | 0.500 | 9.0 | 8.5 | 9.0 | 9.0 | 9.0 | 9.0 | 8.5 | 9.0 | 8.5 | 8.0 | 5.0 | 6.5 |
| | 0.250 | 9.0 | 7.0 | 9.0 | 9.0 | 9.0 | 9.0 | 5.5 | 9.0 | 6.5 | 8.0 | 5.0 | 5.5 |
| | 0.125 | 6.0 | 3.7 | 9.0 | 9.0 | 8.0 | 9.0 | 5.0 | 8.3 | 3.7 | 4.5 | 4.0 | 4.0 |
| 3 | 0.500 | 6.8 | 7.5 | 6.0 | 9.0 | 9.0 | 9.0 | 7.0 | 9.0 | 3.8 | 7.5 | 3.0 | 2.8 |
| | 0.250 | 4.6 | 8.6 | 7.6 | 9.0 | 5.7 | 8.4 | 4.8 | 7.6 | 3.6 | 6.7 | 2.6 | 3.2 |
| | 0.125 | 3.3 | 6.3 | 6.0 | 9.0 | 4.8 | 7.3 | 3.0 | 6.5 | 2.3 | 5.6 | 2.3 | 1.8 |
| 4 | 0.500 | 9.0 | 7.3 | 7.3 | 9.0 | 8.0 | 9.0 | 6.8 | 9.0 | 5.3 | 5.8 | 2.0 | 5.0 |
| | 0.250 | 8.0 | 5.8 | 6.8 | 9.0 | 7.0 | 9.0 | 4.4 | 8.5 | 2.0 | 3.4 | 1.5 | 2.3 |
| | 0.125 | 5.8 | 2.8 | 2.8 | 9.0 | 4.6 | 7.3 | 3.8 | 7.3 | 0.8 | 2.6 | 0.5 | 1.8 |
| 5 | 0.500 | 9.0 | 6.0 | 9.0 | 9.0 | 9.0 | 9.0 | 8.0 | 9.0 | 2.0 | 6.0 | 4.0 | 4.0 |
| | 0.250 | 9.0 | 5.0 | 9.0 | 9.0 | 9.0 | 9.0 | 5.0 | 8.0 | 4.0 | 5.0 | 4.0 | 5.0 |
| | 0.125 | 9.0 | 3.0 | 5.0 | 9.0 | 9.0 | 9.0 | 5.0 | 4.0 | 2.0 | 5.0 | 3.0 | 5.0 |
| 6 | 0.500 | 9.0 | 4.0 | 7.0 | 9.0 | 9.0 | 9.0 | 7.0 | 9.0 | 3.0 | 5.0 | 3.0 | 2.0 |
| | 0.250 | 7.0 | 3.0 | 4.0 | 9.0 | 9.0 | 9.0 | 6.0 | 6.0 | 3.0 | 7.0 | 3.0 | 5.0 |
| | 0.125 | 9.0 | 0.0 | 5.0 | 9.0 | 7.0 | 9.0 | 4.0 | 4.0 | 4.0 | 5.0 | 2.0 | 2.0 |
| 7 | 0.500 | 7.0 | 2.0 | 8.0 | 9.0 | 7.0 | 9.0 | 3.0 | 7.0 | 2.0 | 7.0 | 3.0 | 4.0 |
| | 0.250 | 4.0 | 0.0 | 6.0 | 8.0 | 7.0 | 8.0 | 2.0 | 6.0 | 4.0 | 6.0 | 3.0 | 5.0 |
| | 0.125 | 3.0 | 0.0 | 3.0 | 3.0 | 6.0 | 4.0 | 3.0 | 3.0 | 0.0 | 5.0 | 2.0 | 5.0 |
| 8 | 0.500 | 9.0 | 9.0 | 3.0 | 9.0 | 9.0 | — | 0.0 | 9.0 | 2.0 | 2.0 | 3.0 | 2.0 |
| | 0.250 | 9.0 | 8.0 | 0.0 | 9.0 | 5.0 | — | 0.0 | 5.0 | 0.0 | 2.0 | 3.0 | 0.0 |
| | 0.125 | 9.0 | 7.0 | 0.0 | 9.0 | 4.0 | — | 0.0 | 0.0 | 0.0 | 3.0 | 3.0 | 0.0 |
| 9 | 0.500 | 4.0 | 9.0 | 3.0 | 9.0 | 9.0 | — | 4.0 | 9.0 | 2.0 | 5.0 | 3.0 | 2.0 |
| | 0.250 | 0.0 | 8.0 | 0.0 | 9.0 | 3.0 | — | 0.0 | 8.0 | 0.0 | 5.0 | 2.0 | 0.0 |
| | 0.125 | 0.0 | 7.0 | 2.0 | 9.0 | 0.0 | — | 0.0 | 4.0 | 0.0 | 4.0 | 2.0 | 0.0 |
| 10 | 0.500 | 0.0 | 0.0 | 0.0 | 9.0 | 2.0 | — | 0.0 | 0.0 | 0.0 | 2.0 | 0.0 | 0.0 |
| | 0.250 | 0.0 | 0.0 | 0.0 | 9.0 | 0.0 | — | 0.0 | 0.0 | 0.0 | 2.0 | 0.0 | 0.0 |
| | 0.125 | 0.0 | 0.0 | 0.0 | 9.0 | 0.0 | — | 0.0 | 0.0 | 0.0 | 2.0 | 0.0 | 0.0 |
| 11 | 0.500 | 6.0 | 7.0 | 0.0 | 9.0 | 4.0 | — | 0.0 | 8.0 | 0.0 | 4.0 | 2.0 | 0.0 |
| | 0.250 | 0.0 | 9.0 | 0.0 | 9.0 | 0.0 | — | 0.0 | 0.0 | 0.0 | 3.0 | 0.0 | 0.0 |
| | 0.125 | 0.0 | 8.0 | 0.0 | 9.0 | 0.0 | — | 0.0 | 0.0 | 0.0 | 2.0 | 0.0 | 0.0 |
| 12 | 0.500 | 0.0 | 0.0 | 9.0 | 0.0 | 0.0 | — | 0.0 | 0.0 | 0.0 | 0.0 | 0.0 | 0.0 |
| | 0.250 | 0.0 | 0.0 | 9.0 | 0.0 | 0.0 | — | 0.0 | 0.0 | 0.0 | 0.0 | 0.0 | 0.0 |
| | 0.125 | 0.0 | 0.0 | 4.0 | 0.0 | 0.0 | — | 0.0 | 0.0 | 0.0 | 0.0 | 0.0 | 0.0 |
| 13 | 0.500 | 8.0 | 9.0 | 8.0 | 9.0 | 7.0 | 9.0 | 3.0 | 4.0 | 2.0 | 4.0 | 3.0 | 2.0 |
| | 0.250 | 8.0 | 7.0 | 7.0 | 8.0 | 7.0 | 7.0 | 2.0 | 2.0 | 0.0 | 3.0 | 2.0 | 1.0 |
| | 0.125 | 6.0 | 7.0 | 6.0 | 9.0 | 5.0 | 8.0 | 0.0 | 0.0 | 0.0 | 2.0 | 2.0 | 0.0 |
| 14 | 0.500 | 9.0 | 4.0 | 0.0 | 9.0 | 0.0 | 3.0 | 0.0 | 0.0 | 0.0 | 1.0 | 0.0 | 0.0 |
| | 0.250 | 8.0 | 4.0 | 0.0 | 9.0 | 0.0 | 0.0 | 0.0 | 0.0 | 0.0 | 1.0 | 0.0 | 0.0 |
| | 0.125 | 6.0 | 0.0 | 0.0 | 9.0 | 0.0 | 0.0 | 0.0 | 0.0 | 0.0 | 1.0 | 1.0 | 0.0 |
| 15 | 0.500 | 7.0 | 9.0 | 3.0 | 9.0 | 9.0 | 9.0 | 8.0 | 6.0 | 3.0 | 8.0 | 5.0 | 5.0 |
| | 0.250 | 5.0 | 9.0 | 2.0 | 9.0 | 6.0 | 8.0 | 7.0 | 4.0 | 3.0 | 7.0 | 5.0 | 3.0 |
| | 0.125 | 3.0 | 8.0 | 4.0 | 9.0 | 4.0 | 9.0 | 3.0 | 2.0 | 2.0 | 6.0 | 4.0 | 3.0 |
| 16 | 0.500 | 6.0 | 9.0 | 5.0 | 9.0 | 7.0 | 9.0 | 6.0 | 6.0 | 4.0 | 7.0 | 6.0 | 3.0 |
| | 0.250 | 3.0 | 9.0 | 3.0 | 9.0 | 4.0 | 9.0 | 3.0 | 2.0 | 1.0 | 6.0 | 5.0 | 2.0 |
| | 0.125 | 0.0 | 8.0 | 2.0 | 9.0 | 0.0 | 9.0 | 0.0 | 0.0 | 0.0 | 5.0 | 5.0 | 1.0 |
| 17 | 0.500 | 6.0 | 7.0 | 4.0 | 9.0 | 4.0 | 9.0 | 0.0 | 3.0 | 1.0 | 3.0 | 4.0 | 0.0 |
| | 0.250 | 3.0 | 9.0 | 2.0 | 9.0 | 0.0 | 9.0 | 0.0 | 0.0 | 0.0 | 2.0 | 2.0 | 0.0 |
| | 0.125 | 2.0 | 3.0 | 2.0 | 9.0 | 0.0 | 9.0 | 0.0 | 0.0 | 0.0 | 2.0 | 1.0 | 0.0 |
| 21 | 0.500 | — | — | 7.0 | — | — | 9.0 | — | — | — | — | — | — |
| 22 | 0.500 | — | — | 3.0 | — | — | 0.0 | — | — | — | — | — | — |
| 24 | 0.500 | — | — | 0.0 | — | — | 0.0 | — | — | — | — | — | — |
| 27 | 0.500 | — | — | 0.0 | — | — | 8.0 | — | — | — | — | — | — |
| 28 | 0.500 | 4.0 | 7.0 | 3.0 | 7.0 | 6.0 | 6.0 | 3.0 | 3.0 | — | 4.0 | 1.0 | 1.0 |
| | 0.250 | 3.0 | 5.0 | 2.0 | 6.0 | 3.0 | 4.0 | 2.0 | 2.0 | 1.0 | 2.0 | 0.0 | 0.0 |
| | 0.125 | 0.0 | 5.0 | 0.0 | 3.0 | 2.0 | 3.0 | 0.0 | 0.0 | 0.0 | 1.0 | 0.0 | 0.0 |
| 29 | 0.500 | 2.0 | 2.0 | 4.0 | 7.0 | 4.0 | 5.0 | 0.0 | 0.0 | 0.0 | 6.0 | 2.0 | 1.0 |
| | 0.250 | 0.0 | 4.0 | 2.0 | 5.0 | 4.0 | 3.0 | 0.0 | 0.0 | 0.0 | 5.0 | 1.0 | 1.0 |
| | 0.125 | 0.0 | 3.0 | 4.0 | 5.0 | 0.0 | 0.0 | 0.0 | 1.0 | 0.0 | 3.0 | 0.0 | 0.0 |
| 30 | 0.500 | 3.0 | 9.0 | 5.0 | 9.0 | 5.0 | 6.0 | 5.0 | 7.0 | 1.0 | 6.0 | 0.0 | 1.0 |
| | 0.250 | 2.0 | 5.0 | 3.0 | 7.0 | 4.0 | — | 2.0 | 4.0 | 0.0 | 6.0 | 3.0 | 0.0 |
| | 0.125 | 0.0 | 2.0 | 0.0 | 4.0 | 2.0 | 5.0 | 0.0 | 0.0 | 0.0 | 5.0 | 1.0 | 0.0 |
| 31 | 0.500 | 4.0 | 6.0 | 4.0 | 9.0 | 7.0 | 9.0 | 8.0 | 9.0 | 2.0 | 3.0 | 2.0 | 2.0 |
| | 0.250 | 4.0 | — | — | 9.0 | 8.0 | 3.0 | 7.0 | 7.0 | 2.0 | 3.0 | 2.0 | 2.0 |

TABLE II-continued

Preemergence Herbicidal Evaluations Of Test Compounds

| Compound Number | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
|    | 0.125 | 3.0 | 5.0 | 3.0 | 9.0 | 5.0 | 3.0 | 6.0 | 5.0 | 1.0 | 3.0 | 1.0 | 1.0 |
| 32 | 0.500 | 2.0 | 4.0 | 2.0 | 3.0 | 3.0 | 6.0 | 2.0 | 2.0 | 0.0 | 2.0 | 1.0 | 0.0 |
|    | 0.250 | 0.0 | 3.0 | 0.0 | 0.0 | 0.0 | 6.0 | 0.0 | 5.0 | 0.0 | 2.0 | 0.0 | 0.0 |
|    | 0.125 | 0.0 | 3.0 | 0.0 | 0.0 | 0.0 | 0.0 | 0.0 | 4.0 | 0.0 | 2.0 | 0.0 | 0.0 |
| 33 | 0.500 | 7.0 | 8.0 | 8.0 | 9.0 | 8.0 | 9.0 | 7.0 | 9.0 | 3.0 | 8.0 | 2.0 | 2.0 |
|    | 0.250 | 7.0 | 7.0 | 6.0 | 9.0 | 8.0 | 4.0 | 5.0 | 7.0 | 2.0 | 7.0 | 1.0 | 2.0 |
|    | 0.125 | 3.0 | 6.0 | 5.0 | 9.0 | 5.0 | 5.0 | 2.0 | 3.0 | 0.0 | 5.0 | 0.0 | 1.0 |
| 34 | 0.500 | 0.0 | 0.0 | 0.0 | 0.0 | 0.0 | 8.0 | 0.0 | 0.0 | 0.0 | 0.0 | 0.0 | 0.0 |
|    | 0.250 | 0.0 | 0.0 | 0.0 | 0.0 | 0.0 | 9.0 | 0.0 | 0.0 | 0.0 | 0.0 | 0.0 | 0.0 |
|    | 0.125 | 0.0 | 0.0 | 0.0 | 0.0 | 0.0 | 0.0 | 0.0 | 0.0 | 0.0 | 0.0 | 0.0 | 0.0 |
| 35 | 0.500 | 0.0 | 0.0 | 0.0 | 0.0 | 0.0 | 0.0 | 0.0 | 0.0 | 1.0 | 0.0 | 0.0 | 0.0 |
| 36 | 0.500 | 0.0 | 0.0 | 4.0 | 9.0 | 0.0 | 0.0 | 0.0 | 0.0 | 0.0 | 0.0 | 0.0 | 0.0 |
|    | 0.250 | 0.0 | 0.0 | 3.0 | 3.0 | 0.0 | 0.0 | 0.0 | 0.0 | 0.0 | 0.0 | 0.0 | 0.0 |
|    | 0.125 | 0.0 | 0.0 | 0.0 | 0.0 | 0.0 | 0.0 | 0.0 | 0.0 | 0.0 | 0.0 | 0.0 | 0.0 |
| 37 | 0.500 | 0.0 | 0.0 | 0.0 | 0.0 | 0.0 | 9.0 | 0.0 | 0.0 | 1.0 | 5.0 | 2.0 | 3.0 |
|    | 0.250 | 0.0 | 0.0 | 0.0 | 9.0 | 0.0 | 9.0 | 0.0 | 0.0 | 0.0 | 5.0 | 0.0 | 2.0 |
|    | 0.125 | 0.0 | 0.0 | 0.0 | 0.0 | 0.0 | 0.0 | 0.0 | 0.0 | 0.0 | 3.0 | 0.0 | 2.0 |
| 38 | 0.500 | 0.0 | 0.0 | 0.0 | 0.0 | 0.0 | 0.0 | 0.0 | 0.0 | 1.0 | 3.0 | 1.0 | 2.0 |
| 39 | 0.500 | 0.0 | 6.0 | 6.0 | 9.0 | 9.0 | 9.0 | 6.0 | 9.0 | 2.0 | 1.0 | 1.0 | 2.0 |
|    | 0.250 | 3.0 | 6.5 | 5.5 | 9.0 | 5.0 | 9.0 | 5.0 | 8.5 | 2.0 | 5.0 | 0.5 | 2.0 |
|    | 0.125 | 1.5 | 2.0 | 4.5 | 9.0 | 1.5 | 4.5 | 2.5 | 8.0 | 2.0 | 4.5 | 0.0 | 2.5 |
| 40 | 0.250 | 0.0 | 0.0 | 1.0 | 7.5 | 0.5 | 4.5 | 3.0 | 3.5 | 2.5 | 2.0 | 0.0 | 0.5 |
|    | 0.125 | 1.0 | 0.0 | 1.0 | 3.0 | 0.5 | 4.5 | 1.0 | 1.5 | 1.0 | 1.0 | 0.0 | 1.5 |
| 41 | 0.500 | 0.0 | 0.0 | 0.0 | 9.0 | 6.0 | 9.0 | 0.0 | 8.0 | 2.0 | 5.0 | 0.0 | 2.0 |
|    | 0.250 | 0.0 | 0.0 | 2.0 | 9.0 | 0.0 | 3.0 | 0.0 | 2.0 | 0.0 | 6.0 | 0.0 | 0.0 |
|    | 0.125 | 0.0 | 0.0 | 2.0 | 9.0 | 5.0 | 0.0 | 0.0 | 0.0 | 0.0 | 5.0 | 0.0 | 0.0 |
| 42 | 0.500 | 1.0 | 2.0 | 0.0 | 9.0 | 0.0 | — | 0.0 | 0.0 | 0.0 | 1.5 | 0.5 | 0.0 |
|    | 0.250 | 0.0 | 0.0 | 0.0 | 9.0 | 0.0 | — | 0.0 | 2.0 | 0.0 | 1.0 | 0.5 | 0.0 |
|    | 0.125 | 0.0 | 0.0 | 0.0 | 9.0 | 0.0 | — | 0.0 | 0.0 | 0.0 | 0.0 | 0.0 | 0.0 |
| 43 | 0.500 | 3.0 | 3.0 | 4.5 | 9.0 | 3.5 | — | 8.5 | 9.0 | 1.0 | 3.5 | 0.5 | 2.0 |
|    | 0.250 | 2.0 | 3.0 | 2.0 | 9.0 | 2.0 | — | 3.5 | 9.0 | 0.0 | 0.5 | 0.5 | 0.5 |
|    | 0.125 | 3.0 | 5.5 | 1.0 | 9.0 | 0.0 | — | 0.0 | 4.0 | 0.5 | 1.5 | 0.5 | 1.0 |
| 44 | 0.500 | 6.0 | 0.0 | 0.0 | 9.0 | 9.0 | — | 2.0 | 9.0 | 0.0 | 0.0 | 0.0 | 0.0 |
|    | 0.250 | 0.0 | 0.0 | — | 9.0 | 9.0 | — | 0.0 | 8.0 | 0.0 | 0.0 | 0.0 | 0.0 |
|    | 0.125 | 0.0 | 0.0 | — | 9.0 | 0.0 | — | 0.0 | 9.0 | 0.0 | 0.0 | 0.0 | 0.0 |
| 45 | 0.500 | 9.0 | 0.0 | 0.0 | 9.0 | 0.0 | — | 7.0 | 9.0 | 1.0 | 3.0 | 1.0 | 0.0 |
|    | 0.250 | 9.0 | 0.0 | 0.0 | 9.0 | 0.0 | — | 7.0 | 9.0 | 1.0 | 1.0 | 1.0 | 0.0 |
|    | 0.125 | 0.0 | 0.0 | 0.0 | 9.0 | 0.0 | — | 0.0 | 0.0 | 0.0 | 0.0 | 0.0 | 0.0 |
| 46 | 0.500 | 0.0 | 0.0 | 0.0 | 9.0 | 0.0 | 8.0 | 0.0 | 0.0 | 1.0 | 5.0 | 1.0 | 1.0 |
|    | 0.250 | 0.0 | 0.0 | 0.0 | 7.0 | 0.0 | 7.0 | 0.0 | 0.0 | 1.0 | 7.0 | 1.0 | 3.0 |
|    | 0.125 | 0.0 | 0.0 | 0.0 | 0.0 | 0.0 | 0.0 | 0.0 | 0.0 | 1.0 | 4.0 | 1.0 | 3.0 |

EXAMPLE 42

Rice tolerance to post-transplant applications and preemergence weed control under flooded paddy conditions The tolerance of transplanted rice to post-transplanted herbicide applications is determined as follows: two ten-day-old rice seedlings (CV. Tebonnet) are transplanted into a silt loam soil in 32 oz. plastic containers with a diameter of 10.5 cm and no drainage holes. After transplanting the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of about 0.5, 0.25, 0.125 and 0.063 kg/ha of active ingredient. The treated containers are placed on greenhouse benches, watered such that the water level is maintained as stated above, and cared for according to normal greenhouse procedures. Three to four weeks after treatment the test is terminated and each container is examined and herbicidal effect rated according to the rating system provided in Example 40. The data obtained are reported in Table III. The compounds evaluated are reported by compound number given in Example 40.

Preemergence herbicidal activity under flooded paddy conditions is determined as follows: plant seeds or propagating organs are planted in the top 0.5 cm of silt loam soil in 32 oz. plastic containers with a diameter of 10.5 cm and no drainage holes. Water is added to these containers and maintained at 1.5 to 3 cm above the soil surface for the duration of the experiment. The test compounds are applied as aqueous/acetone mixtures 50/50 v/v pipetted directly into the flood water to give the equivalent of about 0.5, 0.25, 0.125 and 0.063 kg/ha of active ingredient. The treated containers are placed on greenhouse benches and cared for according to normal greenhouse procedures. Three to four weeks after treatment the test is terminated and each container is examined and herbicidal effect rated according to the rating system provided in Example 40. The data obtained are reported in Table III. The compounds evaluated are reported by compound number given in Example 40.

Plant species employed in this example are reported by header abbreviation, common name and scientific name.

| Header Abb. | Common Name | Scientific Name |
|---|---|---|
| PLANT SPECIES EMPLOYED IN RICE TOLERANCE/ PREEMERGENCE WEED CONTROL EVALUATIONS | | |
| ECHORC | Watergrass (Calif.) | ECHINOCHLOA ORYZOIDES (ARD.) FRITSCH |
| CYPIR | Rice Flatsedge | CYPERUS IRIA |
| CYPSE | Flatsedge | CYPERUS SEROTINUS, ROTTB. |
| MOOVA | Monochoria | MONOCHORIA VAGINALIS, PRESL. |
| SAGPY | Arrowhead (Pygmaea) | SAGITTARIA PYGMAEA, L. |
| ORYSAT | Rice, Tebonnet | ORYZA SATIVA, L. TEBONNET |

TABLE III

PADDY CONDITIONS — POST-TRANSPLANT RICE PREEMERGENCE WEEDS

| Cpd. No. | Rate (kg/ha) | ECHORC | CYPIR | CYPSE | MOOVA | SAGPY | ORYSAT |
|---|---|---|---|---|---|---|---|
| 1 | 0.500 | 9.0 | 9.0 | 7.0 | 9.0 | 4.0 | 3.0 |
|   | 0.250 | 9.0 | 9.0 | 6.0 | 9.0 | 0.0 | 2.0 |
|   | 0.125 | 9.0 | 9.0 | 6.0 | 9.0 | 0.0 | 1.0 |
| 2 | 0.500 | 9.0 | 9.0 | 9.0 | 9.0 | 9.0 | 6.7 |
|   | 0.250 | 9.0 | 9.0 | 6.8 | 9.0 | 6.1 | 5.5 |
|   | 0.125 | 9.0 | 9.0 | 5.4 | 9.0 | 3.9 | 4.0 |
|   | 0.063 | 9.0 | 9.0 | 3.0 | 9.0 | 0.8 | 2.5 |
| 3 | 0.500 | 9.0 | 8.8 | 3.7 | 8.8 | 0.0 | 4.0 |
|   | 0.250 | 8.8 | 8.5 | 3.5 | 8.5 | 0.0 | 3.8 |
|   | 0.125 | 8.5 | 6.5 | 1.0 | 7.0 | 0.0 | 3.0 |
|   | 0.063 | 8.7 | 7.0 | 1.0 | 8.7 | 0.0 | 2.7 |
| 4 | 0.500 | 9.0 | 9.0 | 7.3 | 9.0 | 4.5 | 4.7 |
|   | 0.250 | 9.0 | 9.0 | 5.5 | 9.0 | 2.8 | 3.8 |
|   | 0.125 | 8.7 | 9.0 | 2.7 | 9.0 | 0.5 | 3.2 |
|   | 0.063 | 7.2 | 8.5 | 0.5 | 8.5 | 0.3 | 2.0 |
| 5 | 0.500 | 9.0 | 9.0 | 9.0 | 9.0 | 4.0 | 5.3 |
|   | 0.250 | 9.0 | 8.0 | 9.0 | 9.0 | 2.0 | 5.0 |
|   | 0.125 | 8.0 | 7.0 | 9.0 | 8.0 | 2.0 | 4.3 |
|   | 0.063 | 9.0 | — | — | — | — | 3.0 |
| 6 | 0.500 | 9.0 | 9.0 | 7.0 | 9.0 | 0.0 | 1.0 |
|   | 0.250 | 9.0 | 8.0 | 7.0 | 8.0 | 0.0 | 1.0 |
|   | 0.125 | 7.0 | 7.0 | 5.0 | 7.0 | 0.0 | 1.0 |
| 7 | 0.500 | 9.0 | 8.0 | — | 8.0 | 0.0 | 1.0 |
|   | 0.250 | 8.0 | 7.0 | 0.0 | 7.0 | 0.0 | 0.0 |
|   | 0.125 | 7.0 | 4.0 | 0.0 | 6.0 | 0.0 | 0.0 |
| 8 | 0.500 | 6.0 | 8.0 | — | 8.0 | 1.0 | 2.0 |
|   | 0.250 | 4.0 | 8.0 | 0.0 | 8.0 | 0.0 | 1.0 |
|   | 0.125 | 0.0 | 7.0 | 0.0 | 6.0 | 0.0 | 0.0 |
|   | 0.063 | 0.0 | 7.0 | 0.0 | 4.0 | 0.0 | 0.0 |
| 9 | 0.500 | 9.0 | 9.0 | 9.0 | 9.0 | 1.0 | 6.0 |
|   | 0.250 | 9.0 | 9.0 | 9.0 | 9.0 | 1.0 | 5.7 |
|   | 0.125 | 9.0 | 9.0 | 9.0 | 9.0 | 0.0 | 3.7 |
|   | 0.063 | 9.0 | 9.0 | 4.0 | 9.0 | 0.0 | 3.3 |
| 10 | 0.500 | 5.5 | 9.0 | — | 9.0 | 0.0 | 1.0 |
|   | 0.250 | 2.0 | 9.0 | 0.0 | 9.0 | 0.0 | 1.0 |
|   | 0.125 | 1.0 | 9.0 | 0.0 | 9.0 | 0.0 | 1.0 |
|   | 0.063 | 0.0 | 9.0 | 0.0 | 9.0 | 0.0 | 0.0 |
| 11 | 0.500 | 9.0 | 9.0 | 6.0 | 9.0 | 0.0 | 1.0 |
|   | 0.250 | 9.0 | 8.0 | 0.0 | 9.0 | 0.0 | 1.0 |
|   | 0.125 | 9.0 | 7.0 | 0.0 | 8.0 | 0.0 | 0.0 |
|   | 0.063 | 9.0 | 4.0 | 0.0 | 6.0 | 0.0 | 0.0 |
| 12 | 0.500 | 9.0 | 6.5 | 2.0 | 9.0 | 0.0 | 1.0 |
|   | 0.250 | 8.0 | 4.0 | 0.0 | 7.0 | 0.0 | 0.0 |
|   | 0.125 | 6.0 | 2.0 | 0.0 | 6.0 | 0.0 | 0.0 |
|   | 0.063 | 2.0 | — | 0.0 | — | 0.0 | 0.0 |
| 13 | 0.500 | 9.0 | 9.0 | 0.0 | 9.0 | 0.0 | 3.0 |
|   | 0.250 | 9.0 | 9.0 | 0.0 | 9.0 | 0.0 | 3.0 |
|   | 0.125 | 9.0 | 9.0 | 0.0 | 9.0 | 0.0 | 2.0 |
|   | 0.063 | 9.0 | 9.0 | 0.0 | 9.0 | 0.0 | 2.0 |
| 14 | 0.500 | 0.0 | 1.0 | 0.0 | 8.0 | 0.0 | 0.0 |
|   | 0.250 | 0.0 | 0.0 | 0.0 | 6.0 | 0.0 | 0.0 |
|   | 0.125 | 0.0 | 0.0 | 0.0 | 2.0 | 0.0 | 0.0 |

TABLE III-continued

PADDY CONDITIONS — POST-TRANSPLANT RICE
PREEMERGENCE WEEDS

| Cpd. No. | Rate (kg/ha) | ECHORC | CYPIR | CYPSE | MOOVA | SAGPY | ORYSAT |
|---|---|---|---|---|---|---|---|
|  | 0.063 | 0.0 | 0.0 | 0.0 | 0.0 | 0.0 | 0.0 |
| 15 | 0.500 | 9.0 | 9.0 | 9.0 | 9.0 | 2.0 | 7.0 |
|  | 0.250 | 9.0 | 9.0 | 9.0 | 9.0 | 4.5 | 7.0 |
|  | 0.125 | 9.0 | 9.0 | 5.5 | 9.0 | 3.0 | 4.5 |
|  | 0.063 | 8.5 | 8.0 | 2.0 | 9.0 | 1.0 | 4.5 |
| 16 | 0.500 | 9.0 | 9.0 | 9.0 | 9.0 | 0.0 | 6.0 |
|  | 0.250 | 9.0 | 9.0 | 9.0 | 9.0 | 4.5 | 7.0 |
|  | 0.125 | 9.0 | 9.0 | 9.0 | 9.0 | 4.5 | 5.0 |
|  | 0.063 | 9.0 | 8.0 | 5.5 | 9.0 | 4.0 | 3.5 |
| 17 | 0.500 | 9.0 | 9.0 | 9.0 | 9.0 | 0.0 | 2.0 |
|  | 0.250 | 9.0 | 9.0 | 5.5 | 9.0 | 3.5 | 3.0 |
|  | 0.125 | 9.0 | 8.0 | 2.0 | 9.0 | 3.0 | 3.0 |
| 18 | 0.500 | 9.0 | 9.0 | 4.0 | 9.0 | 2.0 | 4.0 |
|  | 0.250 | 9.0 | 9.0 | 2.0 | 9.0 | 0.0 | 3.0 |
|  | 0.125 | 9.0 | 9.0 | 1.0 | 9.0 | 0.0 | 3.0 |
|  | 0.063 | 9.0 | 9.0 | 0.0 | 9.0 | 0.0 | 2.0 |
|  | 0.063 | 9.0 | 4.0 | 0.0 | 9.0 | 0.0 | 2.0 |
| 19 | 0.500 | 9.0 | 6.0 | 0.0 | 9.0 | 0.0 | 1.0 |
|  | 0.250 | 9.0 | 4.0 | 0.0 | 9.0 | 0.0 | 1.0 |
|  | 0.125 | 9.0 | 2.0 | 0.0 | 9.0 | 0.0 | 1.0 |
|  | 0.063 | 8.0 | 2.0 | 0.0 | 9.0 | 0.0 | 1.0 |
| 20 | 0.500 | 9.0 | 9.0 | — | 9.0 | 0.0 | 4.0 |
|  | 0.250 | 9.0 | 7.0 | 2.0 | 9.0 | 0.0 | 3.0 |
|  | 0.125 | 9.0 | 4.0 | 0.0 | 9.0 | 0.0 | 3.0 |
|  | 0.063 | 7.0 | 2.0 | 0.0 | 8.0 | 0.0 | 2.0 |
| 21 | 0.500 | 4.0 | 1.0 | 0.0 | 4.5 | 0.0 | 0.5 |
|  | 0.250 | 6.0 | 2.0 | 0.0 | 8.0 | 0.0 | 0.0 |
|  | 0.125 | 4.0 | 1.0 | 0.0 | 8.0 | 0.0 | 0.0 |
|  | 0.063 | 2.0 | 0.0 | 0.0 | 4.0 | 0.0 | 0.0 |
| 22 | 0.500 | 8.5 | 8.0 | 0.0 | 8.0 | 0.0 | 2.0 |
|  | 0.250 | 6.0 | 2.0 | 0.0 | 7.0 | 0.0 | 0.0 |
|  | 0.125 | 4.0 | 0.0 | 0.0 | 2.0 | 0.0 | 0.0 |
|  | 0.063 | 2.0 | 0.0 | 0.0 | 2.0 | 0.0 | 0.0 |
| 23 | 0.500 | 9.0 | 6.0 | 2.0 | 9.0 | 0.0 | 3.0 |
|  | 0.250 | 7.0 | 2.0 | 1.0 | 9.0 | 0.0 | 3.0 |
|  | 0.125 | 4.0 | 0.0 | 0.0 | 8.0 | 0.0 | 2.0 |
|  | 0.063 | 4.0 | 0.0 | 0.0 | 6.0 | 0.0 | 2.0 |
| 24 | 0.500 | 0.0 | 0.0 | 0.0 | 0.0 | 0.0 | 0.0 |
| 25 | 0.500 | 0.0 | 0.0 | 0.0 | 0.0 | 0.0 | 0.0 |
| 26 | 0.500 | 9.0 | 9.0 | 9.0 | 9.0 | 0.0 | 3.0 |
|  | 0.250 | 9.0 | 9.0 | 6.0 | 9.0 | 0.0 | 3.0 |
|  | 0.125 | 9.0 | 9.0 | 0.0 | 9.0 | 0.0 | 2.0 |
|  | 0.063 | 8.0 | 4.0 | 0.0 | 7.0 | 0.0 | 2.0 |
| 27 | 0.500 | 3.0 | 2.0 | 0.0 | 2.0 | 0.0 | 1.5 |
|  | 0.250 | 1.0 | 2.0 | 0.0 | 2.0 | 0.0 | 2.0 |
|  | 0.125 | 0.0 | 2.0 | 0.0 | 0.0 | 0.0 | 1.0 |
|  | 0.063 | 0.0 | 0.0 | 0.0 | 0.0 | 0.0 | 0.0 |
| 28 | 0.500 | 8.0 | 4.0 | 0.0 | 9.0 | 0.0 | 2.0 |
|  | 0.250 | 2.0 | 0.0 | 0.0 | 2.0 | 0.0 | 2.0 |
|  | 0.125 | 0.0 | 0.0 | 0.0 | 0.0 | 0.0 | 1.0 |
|  | 0.063 | 0.0 | 0.0 | 0.0 | 0.0 | 0.0 | 0.0 |
| 29 | 0.500 | 0.0 | 0.0 | 0.0 | 0.0 | 0.0 | 0.0 |
| 30 | 0.500 | 0.0 | 0.0 | 0.0 | 0.0 | 0.0 | 1.0 |
| 31 | 0.500 | 2.0 | 6.0 | 0.0 | — | 0.0 | 2.0 |
|  | 0.250 | 0.0 | 4.0 | 0.0 | — | 0.0 | 1.0 |
|  | 0.125 | 0.0 | 0.0 | 0.0 | 0.0 | 0.0 | 0.0 |
|  | 0.063 | 0.0 | 0.0 | 0.0 | 0.0 | 0.0 | 0.0 |
| 32 | 0.500 | 0.0 | 0.0 | 0.0 | 0.0 | 0.0 | 0.0 |
| 33 | 0.500 | 9.0 | 9.0 | 0.0 | 9.0 | 0.0 | 4.0 |
|  | 0.250 | 9.0 | 9.0 | 0.0 | 9.0 | 0.0 | 3.0 |
|  | 0.125 | 9.0 | 9.0 | 0.0 | 9.0 | 0.0 | 3.0 |
|  | 0.063 | 8.0 | 9.0 | 0.0 | 9.0 | 0.0 | 3.0 |
| 34 | 0.500 | 0.0 | 0.0 | 0.0 | 0.0 | 0.0 | 0.0 |
| 35 | 0.500 | 0.0 | 0.0 | 0.0 | 0.0 | 0.0 | 0.0 |
| 36 | 0.500 | 4.0 | 1.0 | 0.0 | 1.0 | 0.0 | 0.0 |
|  | 0.250 | 4.0 | 0.0 | 0.0 | 0.0 | 0.0 | 0.0 |
|  | 0.125 | 2.0 | 0.0 | 0.0 | 0.0 | 0.0 | 0.0 |
|  | 0.063 | 0.0 | 0.0 | 0.0 | 0.0 | 0.0 | 0.0 |
| 37 | 0.500 | 2.0 | 0.0 | 0.0 | 1.0 | 0.0 | 2.0 |
|  | 0.250 | 0.0 | 0.0 | 0.0 | 1.0 | 0.0 | 1.0 |
|  | 0.125 | 0.0 | 0.0 | 0.0 | 0.0 | 0.0 | 1.0 |
|  | 0.063 | 0.0 | 0.0 | 0.0 | 0.0 | 0.0 | 0.0 |
| 38 | 0.500 | 0.0 | 0.0 | 0.0 | 0.0 | 0.0 | 0.0 |

TABLE III-continued

| | | PADDY CONDITIONS — POST-TRANSPLANT RICE PREEMERGENCE WEEDS | | | | | |
|---|---|---|---|---|---|---|---|
| Cpd. No. | Rate (kg/ha) | ECHORC | CYPIR | CYPSE | MOOVA | SAGPY | ORYSAT |
| 39 | 0.500 | 9.0 | 9.0 | 8.0 | 9.0 | 3.0 | 5.3 |
| | 0.250 | 9.0 | 9.0 | 5.0 | 9.0 | 1.0 | 5.0 |
| | 0.125 | 8.8 | 9.0 | 7.0 | 9.0 | 0.0 | 3.5 |
| | 0.063 | 8.0 | 9.0 | 1.0 | 9.0 | 0.0 | 2.5 |
| 40 | 0.500 | 9.0 | 8.0 | 0.0 | 9.0 | 0.0 | 1.5 |
| | 0.250 | 5.5 | 6.5 | 0.0 | 8.5 | 0.0 | 1.5 |
| | 0.125 | 3.0 | 5.0 | 0.0 | 5.5 | 0.0 | 0.5 |
| | 0.063 | 1.5 | 3.5 | 0.0 | 4.5 | 0.0 | 0.5 |
| 41 | 0.500 | 9.0 | 9.0 | 1.0 | 9.0 | 0.0 | 0.0 |
| | 0.250 | 9.0 | 8.0 | 0.0 | 9.0 | 0.0 | 0.0 |
| | 0.125 | 4.0 | 6.0 | 0.0 | 9.0 | 0.0 | 0.0 |
| | 0.063 | 1.0 | 0.0 | 0.0 | 8.0 | 0.0 | 0.0 |
| 42 | 0.500 | 0.0 | 2.0 | 0.0 | 0.0 | 0.0 | 2.0 |
| | 0.250 | 0.0 | 0.0 | 0.0 | 0.0 | 0.0 | 1.0 |
| 43 | 0.500 | 9.0 | 9.0 | 2.0 | 9.0 | 2.0 | 4.0 |
| | 0.250 | 9.0 | 9.0 | 0.0 | 9.0 | 0.0 | 4.0 |
| | 0.125 | 9.0 | 9.0 | 0.0 | 9.0 | 0.0 | 3.0 |
| | 0.063 | 9.0 | 6.0 | 0.0 | 8.0 | 0.0 | 2.0 |
| 44 | 0.500 | 9.0 | 9.0 | 9.0 | 9.0 | 2.0 | 3.0 |
| | 0.250 | 9.0 | 9.0 | 1.0 | 9.0 | 1.0 | 2.0 |
| | 0.125 | 9.0 | 9.0 | 0.0 | 8.0 | 0.0 | 1.0 |
| | 0.063 | 7.0 | 7.0 | 0.0 | 6.0 | 0.0 | 1.0 |
| 45 | 0.500 | 9.0 | 9.0 | 9.0 | 9.0 | 9.0 | 6.0 |
| | 0.250 | 8.0 | 9.0 | 9.0 | 6.0 | 2.0 | 4.0 |
| | 0.125 | 8.0 | 9.0 | 9.0 | 6.0 | 0.0 | 2.0 |
| | 0.063 | 5.0 | 8.0 | 0.0 | 2.0 | 0.0 | 2.0 |
| 46 | 0.500 | 0.0 | 0.0 | 0.0 | 0.0 | 0.0 | 0.0 |

EXAMPLE 43

Preemergence herbicidal evaluation of test compounds in the presence of transplanted rice under flooded paddy conditions In this example, Deluvian paddy soil (Toyokawa paddy soil) is placed in plastic pots, 100 cm²×9 cm in depth. Water is added to the level of the soil surface in the pot and the mixture is paddled 3 cm in depth.

Pots are then variously sown with monocotyledenous weed seeds and tubers at 0–2 cm in soil depth, as well as transplanted rice plants at the 2.5 leaf stage. The rice plants are transplanted at about 3 cm soil depth. Water is then added to all of the pots to 3 cm deep and kept at a depth of 3 cm for the duration of the test. Test compounds are applied in the manner described in Example 42 three days after transplanting the rice plants and sowing the weed seeds and tubers. The pots are then placed on greenhouse benches and cared for in the conventional manner. Tests are examined at 25 to 30 days after treatment and rated according to the rating system provided in Example 40. The data obtained are recorded in Table IV below. The compounds evaluated are reported by compound number given in Example 40.

| | PLANT SPECIES USED | |
|---|---|---|
| Abb. | Common Name | Scientific Name |
| ECHCG | Barnyard Grass | ECHINOCHLOA CRUS-GALLI |
| SAGPY | Arrowhead (Pygmaea) | SAGITTARIA PYGMAEA |
| CYPSE | Flatsedge, perennial | CYPERUS SEROTINUS |
| MOOVA | Monochoria | MONOCHORIA VAGINALIS |
| CYPDI | Flatsedge, smallflower | CYPERUS DIFFORMIS |
| SCPJU | Bulrush, Japanese | SCIRPUS JUNCOIDES |
| ORYSAK | Rice, Koshihikari | ORYZA SATIVA, L. CV. KOSHIHIKARI |

TABLE IV

| | | PREEMERGENCE/POST-TRANSPLANT EVALUATION | | | | | | |
|---|---|---|---|---|---|---|---|---|
| Cpd. No. | Rate (kg/ha) | ECHCG | SAGPY | CYPSE | MOOVA | CYPDI | SCPJU | ORYSAK |
| 2 | 0.250 | 9.0 | 9.0 | 9.0 | 9.0 | 9.0 | 9.0 | 9.0 |
| | 0.100 | 9.0 | 9.0 | 9.0 | 9.0 | 9.0 | 9.0 | 5.0 |
| | 0.050 | 9.0 | 7.0 | 7.0 | 9.0 | 9.0 | 9.0 | 3.0 |
| | 0.025 | 9.0 | 3.0 | 4.0 | 9.0 | 9.0 | 8.0 | 1.0 |
| 3 | 0.250 | 9.0 | 3.0 | 9.0 | 9.0 | 9.0 | 9.0 | 8.0 |

TABLE IV-continued

PREEMERGENCE/POST-TRANSPLANT EVALUATION

| Cpd. No. | Rate (kg/ha) | ECHCG | SAGPY | CYPSE | MOOVA | CYPDI | SCPJU | ORYSAK |
|---|---|---|---|---|---|---|---|---|
|  | 0.100 | 9.0 | 1.0 | 8.0 | 7.0 | 9.0 | 9.0 | 5.0 |
|  | 0.050 | 9.0 | 0.0 | 5.0 | 5.0 | 8.0 | 7.0 | 1.0 |
|  | 0.025 | 8.0 | 0.0 | 0.0 | 3.0 | 5.0 | 5.0 | 0.0 |
| 4 | 0.250 | 9.0 | 9.0 | — | 9.0 | 9.0 | 9.0 | 9.0 |
|  | 0.125 | 9.0 | 6.0 | — | 9.0 | 9.0 | 9.0 | 7.0 |
|  | 0.063 | 9.0 | 2.0 | — | 9.0 | 9.0 | 9.0 | 4.0 |
|  | 0.032 | 9.0 | 0.0 | — | 9.0 | 9.0 | 7.0 | 1.0 |
| 5 | 0.250 | 9.0 | 8.0 | — | 9.0 | 9.0 | 9.0 | 2.0 |
|  | 0.125 | 8.0 | 9.0 | — | 9.0 | 9.0 | 9.0 | 2.0 |
|  | 0.063 | 8.0 | 3.0 | — | 9.0 | 9.0 | 6.0 | 0.0 |
|  | 0.032 | 8.0 | 1.0 | — | 9.0 | 8.0 | 4.0 | 0.0 |
| 8 | 0.250 | 9.0 | 8.0 | — | 9.0 | 9.0 | 8.0 | 6.0 |
|  | 0.125 | 9.0 | 6.0 | — | 9.0 | 9.0 | 7.0 | 2.0 |
|  | 0.063 | 8.0 | 3.0 | — | 9.0 | 9.0 | 5.0 | 3.0 |
|  | 0.032 | 8.0 | 1.0 | — | 7.0 | 7.0 | 1.0 | 2.0 |
| 9 | 0.250 | 9.0 | 9.0 | — | 9.0 | 9.0 | 9.0 | 9.0 |
|  | 0.125 | 9.0 | 9.0 | — | 9.0 | 9.0 | 9.0 | 9.0 |
|  | 0.063 | 9.0 | 9.0 | — | 6.0 | 9.0 | 9.0 | 9.0 |
|  | 0.032 | 9.0 | 2.0 | — | 6.0 | 9.0 | 6.0 | 6.0 |
| 10 | 0.250 | 9.0 | 9.0 | — | 9.0 | 9.0 | 8.0 | 2.0 |
|  | 0.125 | 9.0 | 5.0 | — | 9.0 | 9.0 | 6.0 | 1.0 |
|  | 0.063 | 9.0 | 2.0 | — | 6.0 | 7.0 | 0.0 | 1.0 |
|  | 0.032 | 4.0 | 0.0 | — | 2.0 | 5.0 | 0.0 | 0.0 |

EXAMPLE 44

Comparative herbicidal evaluations

The postemergence, preemergence and pre-weed/post-transplanted rice herbicidal properties of certain compounds of the present invention are compared with certain 1,3,5-triazinone compounds described in U.S. Pat. No. 4,512,797. The evaluations are performed as described in Examples 40, 41 and 42. The results are reported in Tables V, VI and VII. Data in Tables V, VI and VII are reported by compound number given in Example 40 for the compounds of the present invention or by comparative compound letter for the compounds described in U.S. Pat. No. 4,512,797.

As can be seen from the data in Tables V-VII, the compounds of the present invention are more effective herbicidal agents, in general, than the compounds described in U.S. Pat. No. 4,512,797.

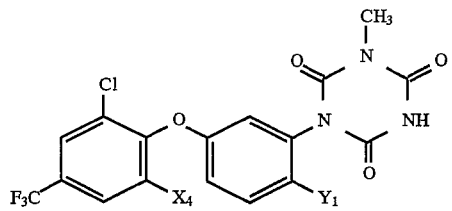

| Comparative Compound Letter | $X_4$ | $Y_1$ |
|---|---|---|
| A | F | Br |
| B | H | $NO_2$ |
| C | F | F |
| D | F | $NO_2$ |
| E | H | H |
| F | H | Cl |

TABLE V

Postemergence Comparative Evaluations

| Compound | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| 2 | 0.500 | 9.0 | 8.0 | 9.0 | 8.5 | 9.0 | 9.0 | 9.0 | 9.0 | 8.3 | 7.5 | 8.5 | 8.3 |
|  | 0.250 | 9.0 | 7.5 | 9.0 | 8.5 | 9.0 | 9.0 | 9.0 | 9.0 | 8.0 | 7.0 | 8.0 | 8.3 |
|  | 0.125 | 9.0 | 7.3 | 9.0 | 8.7 | 8.7 | 9.0 | 6.7 | 9.0 | 7.2 | 6.3 | 7.5 | 8.4 |
|  | 0.063 | 8.8 | 8.0 | 9.0 | 8.8 | 8.3 | 9.0 | 5.0 | 7.5 | 6.9 | 6.3 | 7.0 | 7.7 |
| A | 0.500 | 9.0 | 5.0 | — | 9.0 | 9.0 | — | 2.0 | 5.0 | 5.0 | — | — | 2.0 |
|  | 0.250 | 6.0 | — | — | 9.0 | 9.0 | — | 2.0 | 2.0 | 3.0 | — | — | 0.0 |
|  | 0.125 | 6.0 | 2.0 | — | 9.0 | 7.0 | — | 0.0 | 2.0 | 3.0 | — | — | 0.0 |
|  | 0.063 | 5.0 | 1.0 | — | 9.0 | 6.0 | — | 0.0 | 0.0 | 2.0 | — | — | 0.0 |
| 3 | 0.250 | 8.9 | 9.0 | 8.4 | 7.4 | 8.9 | 8.4 | 7.9 | 7.9 | 6.3 | 6.6 | 7.6 | 6.9 |
|  | 0.125 | 8.8 | 8.8 | 8.8 | 7.2 | 8.9 | 8.7 | 6.7 | 6.8 | 5.9 | 5.7 | 7.1 | 5.8 |
|  | 0.063 | 8.1 | 8.6 | 8.4 | 6.0 | 8.3 | 8.3 | 5.1 | 5.1 | 5.3 | 5.1 | 6.8 | 4.8 |
|  | 0.031 | 7.3 | 8.3 | 7.7 | 5.1 | 7.6 | 8.2 | 4.3 | 3.9 | 4.8 | 4.9 | 6.1 | 4.6 |
| B | 0.250 | 9.0 | 7.0 | 5.5 | 4.5 | 9.0 | 4.5 | 3.5 | 2.0 | 4.3 | 5.0 | 4.3 | 4.3 |
|  | 0.125 | 7.0 | 8.0 | 8.0 | 7.0 | 8.0 | 7.0 | 3.0 | 0.0 | 4.0 | 5.5 | 4.0 | 4.5 |
|  | 0.063 | 7.0 | 4.5 | 4.0 | 2.5 | 9.0 | 2.5 | 2.0 | 1.0 | 4.0 | 4.5 | 3.0 | 3.3 |

TABLE V-continued

Postemergence Comparative Evaluations

| Compound | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| | 0.031 | 4.5 | 3.0 | 3.5 | 2.0 | 8.0 | 2.0 | 1.0 | 0.5 | 3.3 | 4.0 | 3.0 | 3.3 |
| 4 | 0.250 | 9.0 | 8.9 | 8.4 | 9.0 | 9.0 | 8.1 | 8.9 | 9.0 | 7.3 | 6.4 | 8.2 | 8.9 |
| | 0.125 | 9.0 | 8.5 | 9.0 | 8.9 | 9.0 | 8.8 | 8.2 | 9.0 | 6.4 | 5.7 | 8.1 | 8.9 |
| | 0.063 | 8.9 | 8.0 | 8.4 | 8.8 | 8.9 | 8.4 | 6.0 | 8.6 | 5.7 | 5.0 | 7.3 | 8.7 |
| | 0.031 | 8.9 | 7.2 | 8.6 | 7.9 | 8.9 | 7.3 | 3.8 | 6.9 | 5.1 | 4.6 | 6.3 | 8.1 |
| C | 0.250 | 7.0 | 6.0 | 6.0 | 7.0 | 9.0 | 7.0 | 2.0 | 1.0 | 5.0 | 3.5 | 4.5 | 4.5 |
| | 0.125 | 7.0 | 4.0 | 4.0 | 7.0 | 6.0 | 7.0 | 0.0 | 0.0 | 4.5 | 3.5 | 4.5 | 4.0 |
| | 0.063 | 4.0 | 3.0 | 4.0 | 4.0 | 5.0 | 6.0 | 0.0 | 0.0 | 4.5 | 3.5 | 4.0 | 3.5 |
| | 0.031 | 2.0 | 1.0 | 2.0 | 3.0 | 4.0 | 2.0 | 0.0 | 0.0 | 3.5 | 3.0 | 3.5 | 3.0 |
| 16 | 0.125 | 9.0 | 9.0 | 9.0 | 6.5 | 9.0 | 9.0 | 3.7 | 1.3 | 5.6 | 5.8 | 8.4 | 4.2 |
| | 0.063 | 8.3 | 9.0 | 8.3 | 3.7 | 8.3 | 9.0 | 1.7 | 0.8 | 5.1 | 5.3 | 7.4 | 3.4 |
| | 0.031 | 8.0 | 9.0 | 9.0 | 3.0 | 7.0 | 8.0 | 0.7 | 0.0 | 4.6 | 5.3 | 6.4 | 3.0 |
| | 0.016 | 8.3 | 9.0 | 8.7 | 1.5 | 7.0 | 6.0 | 0.5 | 0.0 | 3.8 | 6.0 | 4.7 | 2.4 |
| | 0.008 | 5.5 | 7.0 | 5.5 | 0.0 | 6.0 | 4.5 | 0.0 | 0.0 | 3.3 | 4.0 | 4.5 | 2.0 |
| D | 0.125 | 9.0 | 8.5 | 9.0 | 9.0 | 9.0 | 9.0 | 2.5 | 1.5 | 5.5 | 5.3 | 5.3 | 5.5 |
| | 0.063 | 9.0 | 8.0 | 6.0 | 7.0 | 7.3 | 8.5 | 2.0 | 1.3 | 4.7 | 4.8 | 5.3 | 4.2 |
| | 0.031 | 8.7 | 8.0 | 5.0 | 6.3 | 7.7 | 9.0 | 1.5 | 1.3 | 4.5 | 4.3 | 4.5 | 3.3 |
| | 0.016 | 8.3 | 7.3 | 4.3 | 7.3 | 7.3 | 8.0 | 3.0 | 1.0 | 4.2 | 3.8 | 3.5 | 3.3 |
| | 0.008 | 0.0 | 5.0 | 1.0 | 7.0 | — | 4.0 | — | 0.0 | 2.5 | — | — | 1.0 |
| 28 | 0.500 | 9.0 | 7.0 | 6.5 | 9.0 | 9.0 | 4.5 | 2.0 | 4.0 | 5.0 | 3.0 | 2.0 | 4.5 |
| | 0.250 | 7.0 | 6.0 | 6.0 | 8.0 | 8.0 | 5.0 | 0.0 | 2.0 | 4.5 | 2.5 | 2.0 | 4.0 |
| | 0.125 | 6.0 | 4.0 | 5.0 | 6.0 | 6.0 | 4.0 | 0.0 | 1.0 | 3.5 | 2.0 | 2.0 | 2.5 |
| | 0.063 | 4.0 | 3.0 | 3.0 | 6.0 | 6.0 | 6.0 | 0.0 | 1.0 | 2.5 | 1.5 | 1.5 | 1.5 |
| E | 0.500 | 6.0 | 5.0 | 2.0 | 8.0 | 6.0 | 2.5 | 3.0 | 2.0 | 3.5 | 3.0 | 1.5 | 2.5 |
| | 0.250 | 5.0 | 4.0 | 5.0 | 8.0 | 5.0 | 5.0 | 1.0 | 1.0 | 3.0 | 2.0 | 1.0 | 1.5 |
| | 0.125 | 5.0 | 2.0 | 3.0 | 7.0 | 5.0 | 4.0 | 0.0 | 0.0 | 2.5 | 2.0 | 1.0 | 1.5 |
| | 0.063 | 4.0 | 2.0 | 2.0 | 7.0 | 5.0 | 3.0 | 0.0 | 0.0 | 2.0 | 1.5 | 1.0 | 1.5 |
| 39 | 0.500 | 9.0 | 9.0 | 9.0 | 9.0 | 9.0 | 9.0 | 8.0 | 9.0 | 7.0 | 4.5 | 5.5 | 8.5 |
| | 0.250 | 9.0 | 9.0 | 9.0 | 9.0 | 9.0 | 9.0 | 7.5 | 8.0 | 6.3 | 4.8 | 6.0 | 8.0 |
| | 0.125 | 9.0 | 8.5 | 9.0 | 9.0 | 9.0 | 8.0 | 4.5 | 4.5 | 5.5 | 4.3 | 4.8 | 6.5 |
| | 0.063 | 9.0 | 7.5 | 9.0 | 9.0 | 9.0 | 7.0 | 1.0 | 3.5 | 5.3 | 4.8 | 4.5 | 4.8 |
| | 0.032 | 8.5 | 6.5 | 9.0 | 8.0 | 7.0 | 8.5 | 3.0 | 4.5 | 4.5 | 3.3 | 3.8 | 4.3 |
| | 0.016 | 7.0 | 4.5 | 6.0 | 6.0 | 5.5 | 7.5 | 1.5 | 2.5 | 3.8 | 2.3 | 2.8 | 3.3 |
| F | 0.500 | 9.0 | 7.0 | 6.5 | 9.0 | 7.0 | 6.0 | 2.0 | 3.0 | 5.5 | 3.0 | 3.5 | 4.0 |
| | 0.250 | 7.0 | 6.0 | 9.0 | 9.0 | 6.0 | 8.0 | 2.0 | 3.0 | 5.5 | 3.0 | 3.5 | 4.0 |
| | 0.125 | 5.0 | 6.0 | 8.0 | 8.0 | 5.0 | 6.0 | 1.0 | 2.0 | 4.0 | 3.0 | 3.0 | 3.0 |
| | 0.063 | 5.0 | 6.0 | 5.0 | 6.0 | 6.0 | 6.0 | 0.0 | 3.0 | 4.5 | 2.5 | 2.5 | 2.5 |
| | 0.032 | 4.0 | 3.0 | 4.0 | 5.0 | 4.0 | 6.0 | 0.0 | 1.0 | 3.5 | 1.5 | 1.5 | 2.0 |
| | 0.016 | 4.0 | 2.0 | 2.0 | 4.0 | 3.0 | 5.0 | 0.0 | 0.0 | 3.5 | 1.5 | 1.5 | 1.5 |

TABLE VI

Preemergence Comparative Evaluatuions

| Compound | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| 2 | 0.500 | 9.0 | 8.5 | 9.0 | 9.0 | 9.0 | 9.0 | 8.5 | 9.0 | 8.5 | 8.0 | 5.0 | 6.5 |
| | 0.250 | 9.0 | 7.0 | 9.0 | 90 | 9.0 | 9.0 | 5.5 | 9.0 | 6.5 | 8.0 | 5.0 | 5.5 |
| | 0.125 | 6.0 | 3.7 | 9.0 | 9.0 | 8.0 | 9.0 | 5.0 | 8.3 | 3.7 | 4.5 | 4.0 | 4.0 |
| | 0.063 | 3.3 | 1.0 | 7.0 | 9.0 | 5.7 | 8.5 | 2.7 | 8.0 | 3.0 | 5.0 | 4.0 | 3.0 |
| A | 0.500 | 5.0 | 6.0 | — | 9.0 | 8.0 | — | 7.0 | 8.0 | 2.0 | — | — | 1.0 |
| | 0.250 | 2.0 | 3.0 | — | 9.0 | 3.0 | — | 3.0 | 2.0 | 2.0 | — | — | 0.0 |
| | 0.125 | 1.0 | 2.0 | — | 9.0 | 2.0 | — | 2.0 | 1.0 | 0.0 | — | — | 0.0 |
| | 0.063 | 0.0 | 0.0 | — | 9.0 | 0.0 | — | 0.0 | 0.0 | 0.0 | — | — | 0.0 |
| 3 | 0.250 | 3.8 | 8.7 | 7.2 | 9.0 | 6.1 | 8.5 | 4.6 | 7.8 | 3.5 | 6.1 | 2.3 | 2.8 |
| | 0.125 | 2.6 | 6.6 | 5.4 | 9.0 | 5.2 | 7.6 | 3.0 | 7.0 | 2.3 | 5.3 | 2.0 | 1.4 |
| | 0.063 | 1.4 | 5.4 | 4.0 | 9.0 | 4.3 | 7.2 | 2.8 | 6.4 | 0.8 | 4.8 | 1.2 | 0.8 |
| | 0.031 | 0.0 | 2.8 | 4.6 | 8.2 | 2.2 | 8.2 | 1.5 | 4.0 | 1.0 | 3.5 | 0.4 | 0.8 |
| B | 0.250 | 9.0 | 3.5 | 9.0 | 4.5 | 9.0 | 9.0 | 3.5 | 0.5 | 1.0 | 6.0 | 4.0 | 2.5 |
| | 0.125 | 8.5 | 4.0 | 8.5 | 4.5 | 7.0 | 9.0 | 2.5 | 0.0 | 0.0 | 5.0 | 1.5 | 1.5 |
| | 0.063 | 4.5 | 0.0 | 6.5 | 4.5 | 6.0 | 4.5 | 1.5 | 0.0 | 0.0 | 3.0 | 0.0 | 0.0 |
| | 0.031 | 4.5 | 0.0 | 1.5 | 4.5 | 3.0 | 3.5 | 1.5 | 1.5 | 0.0 | 4.0 | 1.5 | 1.5 |
| 4 | 0.250 | 8.2 | 5.8 | 6.6 | 9.0 | 7.3 | 9.0 | 5.7 | 8.7 | 2.2 | 2.9 | 1.7 | 2.7 |
| | 0.125 | 6.2 | 2.2 | 1.8 | 9.0 | 5.7 | 7.3 | 4.6 | 7.8 | 1.2 | 2.1 | 0.7 | 1.7 |
| | 0.063 | 3.7 | 0.7 | 0.8 | 9.0 | 3.3 | 3.7 | 3.1 | 6.5 | 0.7 | 1.7 | 0.7 | 1.0 |
| | 0.031 | 1.3 | 0.3 | 1.5 | 8.3 | 1.6 | 3.0 | 1.3 | 4.2 | 0.5 | 1.3 | 0.2 | 0.2 |
| C | 0.250 | 4.0 | 0.0 | 2.0 | 9.0 | 3.0 | 9.0 | 4.0 | 2.0 | 0.0 | 2.0 | 2.0 | 0.0 |
| | 0.125 | 7.0 | 0.0 | 5.0 | 9.0 | 0.0 | 9.0 | 2.0 | 2.0 | 0.0 | 2.0 | 0.0 | 0.0 |
| | 0.063 | 2.0 | 0.0 | 3.0 | 7.0 | 2.0 | 8.0 | 0.0 | 4.0 | 0.0 | 0.0 | 0.0 | 0.0 |
| | 0.031 | 0.0 | 0.0 | 0.0 | 6.0 | 0.0 | 7.0 | 0.0 | 2.0 | 0.0 | 0.0 | 0.0 | 0.0 |

TABLE VI-continued

Preemergence Comparative Evaluatuions

| Compound | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| 16 | 0.250 | 3.0 | 9.0 | 3.0 | 9.0 | 4.0 | 9.0 | 3.0 | 2.0 | 1.0 | 6.0 | 5.0 | 2.0 |
|  | 0.125 | 0.0 | 8.0 | 2.0 | 9.0 | 0.0 | 9.0 | 0.0 | 0.0 | 0.0 | 5.0 | 5.0 | 1.0 |
|  | 0.063 | 0.0 | 6.0 | 0.0 | 9.0 | 0.0 | 9.0 | 0.0 | 0.0 | 0.0 | 3.0 | 3.0 | 0.0 |
|  | 0.031 | 0.0 | 2.0 | 0.0 | 9.0 | 0.0 | 9.0 | 0.0 | 0.0 | 1.0 | 3.0 | 1.0 | 0.0 |
| D | 0.250 | 9.0 | 9.0 | 5.0 | 9.0 | 5.0 | 9.0 | 4.0 | 3.0 | 1.0 | 7.0 | 2.0 | 0.0 |
|  | 0.125 | 6.0 | 9.0 | 2.0 | 9.0 | 5.0 | 9.0 | 2.0 | 2.0 | 0.0 | 7.0 | 2.0 | 0.0 |
|  | 0.063 | 6.0 | 7.0 | 3.0 | 9.0 | 3.0 | 8.0 | 0.0 | 0.0 | 0.0 | 7.0 | 2.0 | 0.0 |
|  | 0.031 | 2.0 | 4.0 | 0.0 | 9.0 | 0.0 | 5.0 | 0.0 | 0.0 | 0.0 | 3.0 | 0.0 | 0.0 |
| 28 | 1.000 | 7.0 | 5.0 | 3.0 | 9.0 | 7.0 | 5.0 | 6.0 | 6.0 | 0.0 | 4.0 | 1.0 | 1.0 |
|  | 0.500 | 4.0 | 7.0 | 1.5 | 7.0 | 6.0 | 5.5 | 3.0 | 3.0 | — | 4.0 | 1.0 | 1.0 |
|  | 0.250 | 3.0 | 5.0 | 2.0 | 6.0 | 3.0 | 4.0 | 2.0 | 2.0 | 1.0 | 2.0 | 0.0 | 0.0 |
|  | 0.125 | 0.0 | 5.0 | 0.0 | 3.0 | 2.0 | 3.0 | 0.0 | 0.0 | 0.0 | 1.0 | 0.0 | 0.0 |
| E | 1.000 | 4.0 | 3.0 | 0.0 | 5.0 | 3.0 | 7.0 | 4.0 | 3.0 | 2.0 | 7.0 | 1.0 | 1.0 |
|  | 0.500 | 4.0 | 0.0 | 0.0 | 9.0 | 3.0 | 6.0 | 5.0 | 4.0 | 2.0 | 5.0 | 1.0 | 0.0 |
|  | 0.250 | 3.0 | 0.0 | 0.0 | 7.0 | 4.0 | 5.0 | 2.0 | 3.0 | 0.0 | 5.0 | 1.0 | 0.0 |
|  | 0.125 | 0.0 | 0.0 | 0.0 | 0.0 | 0.0 | 4.0 | 0.0 | 0.0 | 0.0 | 0.0 | 0.0 | 0.0 |
| 39 | 0.500 | 0.0 | 6.0 | 6.0 | 9.0 | 9.0 | 9.0 | 6.0 | 9.0 | 2.0 | 1.0 | 1.0 | 2.0 |
|  | 0.250 | 3.0 | 6.5 | 5.5 | 9.0 | 5.0 | 9.0 | 5.0 | 8.5 | 2.0 | 5.0 | 0.5 | 2.0 |
|  | 0.125 | 1.5 | 2.0 | 4.5 | 9.0 | 1.5 | 4.5 | 2.5 | 8.0 | 2.0 | 4.5 | 0.0 | 2.5 |
|  | 0.063 | 0.0 | 0.0 | 6.0 | 9.0 | 1.0 | 4.5 | 0.0 | 2.5 | 1.5 | 2.0 | 0.0 | 1.0 |
| F | 0.500 | 4.0 | 4.0 | 1.0 | 9.0 | 5.0 | 2.0 | 2.0 | 2.0 | 1.0 | 6.0 | 1.0 | 1.0 |
|  | 0.250 | 5.0 | — | — | 9.0 | 4.0 | 3.0 | 3.0 | 4.0 | 0.0 | 5.0 | 1.0 | 1.0 |
|  | 0.125 | 3.0 | — | 0.0 | 9.0 | 8.0 | 0.0 | 3.0 | 3.0 | 0.0 | 5.0 | 0.0 | 0.0 |
|  | 0.063 | 5.0 | 5.0 | 0.0 | 9.0 | 3.0 | 0.0 | 0.0 | 0.0 | 1.0 | 6.0 | 1.0 | 1.0 |

TABLE VII

Pre-Weed/Post-Transplanted Rice Comparative Evaluations

| Cpd. | Rate (kg/ha) | ECHORC | CYPIR | CYPSE | MOOVA | SAGPY | ORYSAT |
|---|---|---|---|---|---|---|---|
| 3 | 0.250 | 8.8 | 8.5 | 3.5 | 8.5 | 0.0 | 3.8 |
|  | 0.125 | 8.5 | 6.5 | 1.0 | 7.0 | 0.0 | 3.0 |
|  | 0.063 | 8.7 | 7.0 | 1.0 | 8.7 | 0.0 | 2.7 |
|  | 0.031 | 7.5 | 3.0 | 0.0 | 7.0 | 0.0 | 1.0 |
| B | 0.250 | 8.0 | 8.0 | 3.0 | 8.0 | 4.0 | 4.5 |
|  | 0.125 | 6.5 | 7.0 | 3.0 | 6.5 | 3.0 | 2.5 |
|  | 0.063 | 4.0 | 7.0 | 0.0 | 9.0 | 2.0 | 3.0 |
|  | 0.031 | 0.0 | 0.0 | 0.0 | 9.0 | 2.0 | 2.0 |
| 4 | 0.250 | 9.0 | 9.0 | 4.8 | 9.0 | 2.6 | 3.7 |
|  | 0.125 | 8.8 | 9.0 | 2.0 | 9.0 | 0.4 | 3.6 |
|  | 0.063 | 7.4 | 8.6 | 0.4 | 8.6 | 0.2 | 2.1 |
|  | 0.031 | 6.0 | 7.4 | 0.0 | 8.4 | 0.0 | 1.6 |
| C | 0.250 | 2.0 | 8.0 | 0.0 | 9.0 | 0.0 | 5.0 |
|  | 0.125 | 0.0 | 8.0 | 0.0 | 9.0 | 0.0 | 3.0 |
|  | 0.063 | 0.0 | 6.0 | 0.0 | 9.0 | 0.0 | 1.0 |
|  | 0.031 | 0.0 | 4.0 | 0.0 | 9.0 | 0.0 | 1.0 |
| 16 | 0.250 | 9.0 | 9.0 | 9.0 | 9.0 | 4.5 | 7.0 |
|  | 0.125 | 9.0 | 9.0 | 9.0 | 9.0 | 4.5 | 5.0 |
|  | 0.063 | 9.0 | 8.0 | 5.5 | 9.0 | 4.0 | 3.5 |
|  | 0.031 | 9.0 | 7.5 | 4.5 | 9.0 | 3.5 | 3.0 |
| D | 0.250 | 9.0 | 9.0 | 4.0 | 9.0 | 9.0 | 6.0 |
|  | 0.125 | 9.0 | 9.0 | — | 9.0 | 9.0 | 3.0 |
|  | 0.063 | 9.0 | 9.0 | 0.0 | 7.0 | 7.0 | 3.0 |
|  | 0.031 | 9.0 | 7.0 | 0.0 | 4.0 | 4.0 | 3.0 |
| 28 | 1.000 | 7.0 | 7.0 | 0.0 | 9.0 | 0.0 | 3.0 |
|  | 0.500 | 8.5 | 6.5 | 0.0 | 9.0 | 0.0 | 2.0 |
|  | 0.250 | 2.0 | 0.0 | 0.0 | 2.0 | 0.0 | 2.0 |
| E | 1.000 | 0.0 | 0.0 | 0.0 | 0.0 | 0.0 | 0.0 |
|  | 0.500 | 0.0 | 0.0 | 0.0 | 0.0 | 0.0 | 0.0 |
|  | 0.250 | 0.0 | 0.0 | 0.0 | 0.0 | 0.0 | 0.0 |
| 39 | 0.250 | 9.0 | 9.0 | 5.0 | 9.0 | 1.0 | 5.0 |
|  | 0.125 | 8.8 | 9.0 | 7.0 | 9.0 | 0.0 | 3.5 |
|  | 0.063 | 8.0 | 9.0 | 1.0 | 9.0 | 0.0 | 2.5 |
|  | 0.031 | 7.8 | 9.0 | 0.0 | 9.0 | 0.0 | 1.8 |
| F | 0.250 | 0.0 | 4.0 | 0.0 | 8.0 | 0.0 | 2.0 |
|  | 0.125 | 0.0 | 2.0 | 0.0 | 8.0 | 0.0 | 1.0 |
|  | 0.063 | 0.0 | 2.0 | 0.0 | 6.0 | 0.0 | 0.0 |
|  | 0.031 | 0.0 | 0.0 | 0.0 | 4.0 | 0.0 | 0.0 |

What is claimed is:

1. Ethyl 3-{5-[(2-chloro-α,α,α,6-tetrafluoro-p-tolyl)oxy]-2-cyanophenyl}tetrahydro-2,4,6-trioxo-s-triazine-1(2H)-acetate.

2. A method for controlling undesirable plant species which comprises applying to the foliage of said plants or to the soil or water containing seeds or other propagating organs thereof, a herbicidally effective amount of ethyl 3-{5-[(2-chloro-α,α,α,6-tetrafluoro-p-tolyl)oxy]-2-cyanophenyl}tetrahydro-2,4,6-trioxo-s-triazine-1(2H)-acetate.

3. A method for the control of undesirable plant species in transplanted rice which comprises applying to the soil or water containing seeds or other propagating organs of said undesirable plant species, after the rice has been transplanted, a herbicidally effective amount of ethyl 3-{5-[(2-chloro-α,α,α,6-tetrafluoro-p-tolyl)oxy]-2-cyanophenyl}tetrahydro-2,4,6-trioxo-s-triazine-1(2H)-acetate.

4. A herbicidal composition which comprises an inert solid or liquid carrier and a herbicidally effective amount of ethyl 3-{5-[(2-chloro-α,α,α,6-tetrafluoro-p-tolyl)oxy]-2-cyanophenyl}tetrahydro-2,4,6-trioxo-s-triazine-1(2H)-acetate.

* * * * *